US00RE45685E

(19) United States
(12) Reissued Patent
Man et al.

(10) Patent Number: US RE45,685 E
(45) Date of Reissued Patent: Sep. 29, 2015

(54) PHARMACEUTICALLY ACTIVE ISOINDOLINE DERIVATIVES

(71) Applicant: Celgene Corporation, Summit, NJ (US)

(72) Inventors: Hon-Wah Man, Princeton, NJ (US); George W. Muller, Rancho Santa Fe, CA (US)

(73) Assignee: Celgene Corporation, Summit, NJ (US)

(21) Appl. No.: 14/046,779

(22) Filed: Oct. 4, 2013

Related U.S. Patent Documents

Reissue of:
(64) Patent No.: 8,030,343
Issued: Oct. 4, 2011
Appl. No.: 10/685,942
Filed: Oct. 14, 2003

U.S. Applications:
(63) Continuation of application No. 09/708,199, filed on Nov. 8, 2000, now Pat. No. 6,667,316, which is a continuation-in-part of application No. 09/590,344, filed on Jun. 8, 2000, now abandoned.

(51) Int. Cl.

| | |
|---|---|
| ***C07D 209/46*** | (2006.01) |
| ***C07D 209/48*** | (2006.01) |
| ***C07D 413/04*** | (2006.01) |
| ***C07D 471/04*** | (2006.01) |
| ***C07D 487/04*** | (2006.01) |
| ***A61K 31/407*** | (2006.01) |
| ***A61K 31/4178*** | (2006.01) |
| ***A61K 31/4184*** | (2006.01) |
| ***A61K 31/4035*** | (2006.01) |
| ***A61K 31/4245*** | (2006.01) |

(52) U.S. Cl.
CPC ..... *C07D 209/46* (2013.01); *C07D 209/48* (2013.01); *C07D 413/04* (2013.01); *C07D 471/04* (2013.01); *C07D 487/04* (2013.01); *A61K 31/407* (2013.01); *A61K 31/4035* (2013.01); *A61K 31/4178* (2013.01); *A61K 31/4184* (2013.01); *A61K 31/4245* (2013.01)

(58) Field of Classification Search
None
See application file for complete search history.

(56) References Cited

U.S. PATENT DOCUMENTS

| | | | | |
|---|---|---|---|---|
| 4,173,652 | A | 11/1979 | Bruins et al. | |
| 4,556,673 | A | 12/1985 | Anderson et al. | |
| 4,820,828 | A | 4/1989 | Demers et al. | |
| 5,463,063 | A | 10/1995 | Muller | |
| 5,605,914 | A | 2/1997 | Muller | |
| 5,658,940 | A | 8/1997 | Muller et al. | |
| 5,698,579 | A | 12/1997 | Muller | |
| 5,703,098 | A | 12/1997 | Muller et al. | |
| 5,728,844 | A | 3/1998 | Muller et al. | |
| 5,728,845 | A | 3/1998 | Muller et al. | |
| 5,736,570 | A | 4/1998 | Muller et al. | |
| 5,801,195 | A | 9/1998 | Muller et al. | |
| 5,874,448 | A * | 2/1999 | Muller et al. | 514/323 |
| 5,877,200 | A | 3/1999 | Muller et al. | |
| 5,929,117 | A | 7/1999 | Muller et al. | |
| 5,968,945 | A | 10/1999 | Muller et al. | |
| 6,011,050 | A | 1/2000 | Muller et al. | |
| 6,020,358 | A | 2/2000 | Muller et al. | |
| 6,046,221 | A | 4/2000 | Muller et al. | |
| 6,075,041 | A | 6/2000 | Muller | |
| 6,214,857 | B1 | 4/2001 | Muller et al. | |
| 6,403,613 | B1 * | 6/2002 | Man et al. | 514/323 |
| 6,429,221 | B1 | 8/2002 | Muller et al. | |
| 6,458,810 | B1 * | 10/2002 | Muller et al. | 514/323 |
| 6,667,316 | B1 * | 12/2003 | Man et al. | 514/323 |
| 6,699,899 | B1 * | 3/2004 | Man et al. | 514/417 |
| 6,762,195 | B2 * | 7/2004 | Muller et al. | 514/319 |
| 6,911,464 | B2 * | 6/2005 | Man et al. | 514/416 |
| 6,962,940 | B2 * | 11/2005 | Muller et al. | 514/417 |
| 7,005,438 | B2 * | 2/2006 | Muller et al. | 514/323 |

FOREIGN PATENT DOCUMENTS

| | | |
|---|---|---|
| WO | WO 97/05105 | 2/1997 |
| WO | WO 97/23457 | 3/1997 |
| WO | WO 97/24117 | 7/1997 |
| WO | WO 98/24763 | 6/1998 |

OTHER PUBLICATIONS

Burnouf et al., "Recent Advances in PDE4 Inhibitors as Immunoregulators and Anti-Inflammatory Drugs", Current Pharm. Design, 8, pp. 1255-1296 (2002).*
Harrison's Principles of Internal Medicine (1994), pp. 1543-1566.*
Lavoie et al. Lack of clinical efficacy of a phosphodiesterase-4 inhibitor for treatment of heaves in horses. Journal of veterinary internal medicine. 2006;20(1): 175-181, abstract only.*
Clinical Trails.gov. Safety study of clinical and immune effects of PDE-4 inhibitor in cutaneous lupus patients. Jun. 22, 2008, pp. 1-4.*
Anonymous. Ariflo (Cilomilast)—Oral PDE-IV Inhibitor for Chronic Obstructive Pulmonary Disease (COPD). www.drugdevelopment-technology.com/projects/ariflo. Electronic pp. 1-2.*
Bielekova et al., The Journal of Immunology, 164(2), pp. 1117-1124 (2000).*
Burnouf et al., Current Pharmaceutical Design, 8, pp. 1255-1296 (2002).*
Haack et al., Bioorganic & Medicinal Chemistry, 13, pp. 4425-4433 (2005).*
Shire et al., Exp. Opin. Ther. Patents, 8: 531-544 (1998).
He et al., J. Med. Chem., 41: 4216-4223 (1998).

(Continued)

*Primary Examiner* — Bethany Barham
*Assistant Examiner* — Barbara Frazier
(74) *Attorney, Agent, or Firm* — Jones Day

(57) ABSTRACT

Isoindolin-1-one and Isoindoline-1,3-dione substituted in the 2-position with an α-(3,4-disubstituted phenyl)alkyl group and in the 4- and/or 5-position with a nitrogen-containing group are inhibitors of, and thus useful in the treatment of disease states mediated by, TNFα and phosphodiesterase. A typical embodiment is 2-[1-(3-ethoxy-4-methoxyphenyl)-2-methylsulfonylethyl]-4,5-diaminoisoindoline-1,3-dione.

12 Claims, No Drawings

(56) References Cited

OTHER PUBLICATIONS

Draetta et al., in "Annual Reports in Medicinal Chemistry vol. 31," Academic Press, San Diego, 241-246 (1996).
Salmon et al., in "Cecil Textbook of Medicine, 20th Ed.," W.B. Saunders, Philadelphia, 1036-1049 (1996).
Balasubramanian et al., in "Annual Reports in Medicinal Chemistry vol. 33," Academic Press, San Diego, 151-159 (1998).
Miller, in "Cecil Textbook of Medicine, 20th Ed.," W.B. Saunders, Philadelphia, 1071-1077 (1996).
De et al., J. Pharm. Sci., 64(2): 262-266 (1975).
Barnes, Eur. Respir. J., 8: 457-462 (1995).
Bazzoni et al., "Seminars in Medicine of the Beth Israel Hospital, Flier Ed.," Boston, 331(26): 1717-1725 (1996).
Burnouf et al., in "Annual Reports in Medicinal Chemistry vol. 33," Academic Press, San Diego, 91-109 (1998).
Buu-Ho et al., JMC, 13(2): 211-213 (1970).
Badger et al., DDT, 2(10): 427-435 (1997).
Beutler et al., Critical Care Medicine, 21(10): S423-S435 (1993).
Corral et al., Molecular Medicine, 2(4): 1076-1551 (1996).
deBrito et al., Emerging Drugs, 2: 249-268 (1997).
Denis et al., Investigational New Drugs, 15: 175-185 (1997).
Eger et al., Arzneim-Forsch/Drug Res., 40(II): 1073-1075.0 (1990).
Friderichs, Arzneim-Forsch/Drug Res., 32(1), 6: 613-620 (1982).
Hart et al., J. Org. Chem., 48: 289-294 (1983).
Hughes et al., DDT, 2(3): 89-101 (1997).
Kleinman et al., J. Med. Chem., 41: 266-270 (1998).
Lombardo, Current Pharmaceutical Design, 1(2): 255-268 (1995).
Lee et al., Circulatory Shock, 44: 97-103 (1995).
Levy et al., J. Med. Chem., 41: 199-223 (1998).
Müller et al., TIPS, 17: 294-298 (1997).
Marriott, Exp. Opin. Ivest. Drugs, 6(8): 1105-1108 (1997).
Muller et al., Bioorganic & Medicinal Chemistry Letters, 8: 2669-2674 (1998).
Muller et al., J. Med. Chem., 39(17): 3238-3240 (1996).
Natchus et al., Bioorganic & Medicinal Chemistry Letters, 8: 2077-2080 (1998).
Naafs et al., International Journal of Dermatology, 24(2): 131-134 (1985).
Palfreyman, Drugs of the Future, 30(8): 793-804 (1995).
Palacios et al., Il Farmaco, 50(12): 819-827 (1995).
Summers et al., Annual Reports in Medicinal Chemistry, 33: 131-140 (1998).
Steinman et al., Bioorganic & Medicinal Chemistry Letters, 8: 2087-2092 (1998).
Strieter et al., Critical Care Medicine, 21(10): S447-S463 (1993).
Torphy et al., DN&P, 6(4): 203-214 (1993).
Torphy et al., Am J. Resp. Crit. Care Med., 157: 351-370 (1998).
Torphy, Asthma, 1755-1773 (1997).
Teixeira et al., TIPS, 18: 164-170 (1997).
Tracey et al., Annu. Rev. Cell Biol., 9: 317-343 (1993).
Tanaka et al., Chem. Pharm. Bull., 31(8): 2810-2819 (1983).
Wojtowicz-Praga et al., Investigational New Drugs, 16: 61-75 (1997).
Yu et al., Drugs & Aging, 11(3): 229-244 (1997).
Crocker et al, Drug of Today, 35(7): 519-535 (1999).
Norman, Exp. Opin. Ther. Patents, 9(8): 1101-1118 (1999).

* cited by examiner

PHARMACEUTICALLY ACTIVE ISOINDOLINE DERIVATIVES

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

This is a continuation of U.S. patent application Ser. No. 09/708,199, filed Nov. 8, 2000, now U.S. Pat. No. 6,667,316, which is a continuation-in-part of U.S. patent application Ser. No. 09/590,344, filed Jun. 8, 2000, now abandoned, both of which are incorporated herein by reference in their entireties.

The present invention pertains to non-polypeptide isoindoline derivatives that decrease the levels of tumor necrosis factor alpha (TNFα) and inhibit phosphodiesterases (PDEs), particularly PDE 4 and PDE 3, and to the treatment of disease states mediated thereby. The compounds inhibit angiogenesis and are useful in the treatment of cancer, inflammatory, and autoimmune diseases. For example, compounds that selectively PDE 4 are useful in treating inflammation and effecting relaxation of airway smooth muscle with a minimum of unwanted side effects, e.g., cardiovascular or anti-platelet effects. The present invention also relates to methods of treatment and pharmaceutical compositions utilizing such compounds.

BACKGROUND OF THE INVENTION

Tumor necrosis factor α, or TNFα, is a cytokine which is released primarily by mononuclear phagocytes in response to a number immunostimulators. When administered to animals or humans, it causes inflammation, fever, cardiovascular effects, hemorrhage, coagulation, and acute phase responses similar to those seen during acute infections and shock states. Excessive or unregulated TNFα production thus has been implicated in a number of disease conditions. These include endotoxemia and/or toxic shock syndrome {Tracey et al., Nature 330, 662-664 (1987) and Hinshaw et al., Circ. Shock 30, 279-292 (1990)}; rheumatoid arthritis, Crohn's disease, IBD, cachexia {Dezube et al., Lancet, 335 (8690), 662 (1990)} and Adult Respiratory Distress Syndrome where TNFα concentration in excess of 12,000 pg/mL have been detected in pulmonary aspirates from ARDS patients {Millar et al., Lancet 2(8665), 712-714 (1989)}. Systemic infusion of recombinant TNFα also resulted in changes typically seen in ARDS {Ferrai-Baliviera et al., Arch. Surg. 124(12), 1400-1405 (1989)}.

TNFα appears to be involved in bone resorption diseases, including arthritis. When activated, leukocytes will produce bone-resorption, an activity to which the data suggest TNFα contributes. {Bertolini et al., Nature 319, 516-518 (1986) and Johnson et al., Endocrinology 124(3), 1424-1427 (1989)}. TNFα also has been shown to stimulate bone resorption and inhibit bone formation in vitro and in vivo through stimulation of osteoblast formation and activation combined with inhibition of osteoblast function. Although TNFα may be involved in many bone resorption diseases, including arthritis, a most compelling link with disease is the association between production of TNFα by tumor or host tissues and malignancy associated hypercalcemia {Calci. Tissue Int (US) 46(Suppl.), S3-10 (1990)}. In Graft versus Host Reaction, increased serum TNFα levels have been associated with major complication following acute allogenic bone marrow transplants {Holler et al., Blood, 75(4), 1011-1016 (1990)}.

Cerebral malaria is a lethal hyperacute neurological syndrome associated with high blood levels of TNFα and the most severe complication occurring in malaria patients. Levels of serum TNFα correlated directly with the severity of disease and the prognosis in patients with acute malaria attacks {Grau et al., N. Engl. J. Med. 320(24), 1586-1591 (1989)}.

Unregulated angiogenesis is pathologic and sustains progression of many neoplastic and non-neoplastic diseases including solid tumor growth and metastases, arthritis, some types of eye disorders, and psoriasis. See, e.g., Moses et al., 1991, Biotech. 9:630-634; Folkman et al., 1995, N. Engl. J. Med., 333:1757-1763; Auerbach et al., 1985, J. Microvasc. Res. 29:401-411; Folkman, 1985, Advances in Cancer Research, eds. Klein and Weinhouse, Academic Press, New York, pp. 175-203; Patz, 1982, Am. J. Opthahnol. 94:715-743; Folkman et al., 1983, Science 221:719-725; and Folkman and Klagsbrun, 1987, Science 235:442-447. In addition, maintenance of the avascularity of the cornea, lens, and trabecular meshwork is crucial for vision as well as to ocular physiology. See, e.g., reviews by Waltman et al., 1978, Am. J. Ophthal. 85:704-710 and Gartner et al., 1978, Surv. Ophthal. 22:291-312.

Angiogenesis thus is encountered in various disease states, tumor metastasis, and abnormal growth by endothelial cells. Pathological states created by unregulated angiogenesis have been grouped together as angiogenic dependent or angiogenic associated diseases. Control of the angiogenic processes could lead to the mitigation of these conditions.

The components of angiogenesis relating to vascular endothelial cell proliferation, migration and invasion, have been found to be regulated in part by polypeptide growth factors. Endothelial cells exposed to a medium containing suitable growth factors can be induced to evoke some or all of the angiogenic responses. Polypeptides with in vitro endothelial growth promoting activity nclude acidic and basic fibroblast growth factors, transforming growth factors α and β, platelet-derived endothelial cell growth factor, granulocyte colony-stimulating factor, interleukin-8, hepatocyte growth factor, proliferin, vascular endothelial growth factor and placental growth factor. Folkman et al., 1995, N. Engl. J. Med., 333:1757-1763.

Inhibitory influences predominate in the naturally occurring balance between endogenous stimulators and inhibitors of angiogenesis. Rastinejad et al., 1989, Cell 56:345-355. In those instances in which neovascularization occurs under normal physiological conditions, such as wound healing, organ regeneration, embryonic development, and female reproductive processes, angiogenesis is stringently regulated and spatially and temporally delimited. Under conditions of pathological angiogenesis such as that characterizing solid tumor growth, these regulatory controls fail.

Macrophage-induced angiogenesis is known to be mediated by TNFα. Leibovich et al. {Nature, 329, 630-632 (1987)} showed TNFα induces in vivo capillary blood vessel formation in the rat cornea and the developing chick chorioallantoic membranes at very low doses and suggest TNFα is a candidate for inducing angiogenesis in inflammation, wound repair, and tumor growth.

TNFα production also has been independently associated with cancerous conditions, particularly induced tumors {Ching et al., Brit. J. Cancer, (1955) 72, 339-343, and Koch, Progress in Medicinal Chemistry, 22, 166-242 (1985)}. Whether or not involved with TNFα production, angiogenesis is prominent in solid tumor formation and metastasis and angiogenic factors have been found associated with several solid tumors such as rhabdomyosarcomas, retinoblastoma, Ewing sarcoma, neuroblastoma, and osteosarcoma. Tumors in which angiogenesis is important include solid tumors, and benign tumors such as acoustic neuroma, neurofibroma, trachoma and pyogenic granulomas. Independent of its action on TNFα production, the prevention of angiogenesis could halt the growth of these tumors and the resultant damage to the animal due to the presence of the tumor. Angiogenesis has been associated with blood-born tumors such as leukemias and various acute or chronic neoplastic diseases of the bone marrow. In such conditions, unrestrained proliferation of white blood cells occurs, usually accompanied by anemia, impaired blood clotting, and enlargement of the lymph nodes, and spleen.

Angiogenesis also is involved in tumor metastasis. Thus angiogenesis stimulation occurs in vascularization of the tumor, allowing tumor cells to enter the blood stream and circulate throughout the body. After the tumor cells have left the primary site, and have settled into the secondary, metastasis site, angiogenesis must occur before the new tumor can grow and expand.

All of the various cell types of the body can be transformed into benign or malignant tumor cells. The most frequent tumor site is lung, followed by colorectal, breast, prostate, bladder, pancreas, and then ovary. Other prevalent types of cancer include leukemia, central nervous system cancers, including brain cancer, melanoma, lymphoma, erythroleukemia, uterine cancer, and head and neck cancer.

TNFα also plays a role in the area of chronic pulmonary inflammatory diseases. The deposition of silica particles leads to silicosis, a disease of progressive respiratory failure caused by a fibrotic reaction. Antibody to TNFα completely blocked the silica-induced lung fibrosis in mice {Pignet et al., Nature, 344:245-247 (1990)}. High levels of TNFα production (in the serum and in isolated macrophages) have been demonstrated in animal models of silica and asbestos induced fibrosis {Bissonnette et al., Inflammation 13(3), 329-339 (1989)}. Alveolar macrophages from pulmonary sarcoidosis patients have also been found to spontaneously release massive quantities of TNFα as compared with macrophages from normal donors {Baughman et al., J. Lab. Clin. Med. 115(1), 36-42 (1990)}.

TNFα is also implicated in the inflammatory response which follows reperfusion, called reperfusion injury, and is a major cause of tissue damage after loss of blood flow {Vedder et al., PNAS 87, 2643-2646 (1990)}. TNFα also alters the properties of endothelial cells and has various pro-coagulant activities, such as producing an increase in tissue factor procoagulant activity and suppression of the anticoagulant protein C pathway as well as down-regulating the expression of thrombomodulin {Sherry et al., J. Cell Biol. 107, 1269-1277 (1988)}. TNFα has pro-inflammatory activities which together with its early production (during the initial stage of an inflammatory event) make it a likely mediator of tissue injury in several important disorders including but not limited to, myocardial infarction, stroke and circulatory shock. Of specific importance may be TNFα-induced expression of adhesion molecules, such as intercellular adhesion molecule (ICAM) or endothelial leukocyte adhesion molecule (ELAM) on endothelial cells {Munro et al., Am. J. Path. 135(I), 121-132 (1989)}.

TNFα blockage with monoclonal anti-TNFα antibodies has been shown to be beneficial in rheumatoid arthritis {Elliot et al., Int. J. Pharmac. 1995 17(2), 141-145} and Crohn's disease {von Dullemen et al., Gastroenterology, 1995 109(I), 129-135}

Moreover, it now is known that TNFα is a potent activator of retrovirus replication including activation of HIV-1. {Duh et al., Proc. Nat. Acad. Sci. 86, 5974-5978 (1989); Poll et al., Proc. Nat. Acad. Sci. 87, 782-785 (1990); Monto et al., Blood 79, 2670 (1990); Clouse et al., J. Immunol. 142, 431-438 (1989); Poll et al., AIDS Res. Hum. Retrovirus, 191-197 (1992)}. AIDS results from the infection of T lymphocytes with Human immunodeficiency Virus (HIV). At least three types or strains of HIV have been identified; i.e., HIV-1, HIV-2 and HIV-3. As a consequence of HIV infection, T-cell mediated immunity is impaired and infected individuals manifest severe opportunistic infections and/or unusual neoplasms. HIV entry into the T lymphocyte requires T lymphocyte activation. Other viruses, such as HIV-1, HIV-2 infect T lymphocytes after T cell activation and such virus protein expression and/or replication is mediated or maintained by such T cell activation. Once an activated T lymphocyte is infected with HIV, the T lymphocyte must continue to be maintained in an activated state to permit HIV gene expression and/or HIV replication. Cytokines, specifically TNFα, are implicated in activated T-cell mediated HIV protein expression and/or virus replication by playing a role in maintaining T lymphocyte activation. Therefore, interference with cytokine activity such as by prevention or inhibition of cytokine production, notably TNFα, in an HIV-infected individual assists in limiting the maintenance of T lymphocyte caused by HIV infection.

Monocytes, macrophages, and related cells, such as kupffer and glial cells, also have been implicated in maintenance of the HIV infection. These cells, like T cells, are targets for viral replication and the level of viral replication is dependent upon the activation state of the cells. {Rosenberg et al., The Immunopathogenesis of HIV Infection, Advances in Immunology, 57 (1989)}. Cytokines, such as TNFα, have been shown to activate HIV replication in monocytes and/or macrophages {Poli et al., Proc. Natl. Acad. Sci., 87, 782-784 (1990)}; therefore, prevention or inhibition of cytokine production or activity aids in limiting HIV progression for T cells. Additional studies have identified TNFα as a common factor in the activation of HIV in vitro and has provided a clear mechanism of action via a nuclear regulatory protein found in the cytoplasm of cells (Osborn, et al., PNAS 86 2336-2340). This evidence suggests that a reduction of TNFα synthesis may have an antiviral effect in HIV infections, by reducing the transcription and thus virus production.

AIDS viral replication of latent HIV in T cell and macrophage lines can be induced by TNFα {Folks et al., PNAS 86, 2365-2368 (1989)}. A molecular mechanism for the virus inducing activity is suggested by TNFα's ability to activate a gene regulatory protein (NFκB) found in the cytoplasm of cells, which promotes HIV replication through binding to a viral regulatory gene sequence (LTR) {Osborn et al., PNAS 86, 2336-2340 (1989)}. TNFα in AIDS associated cachexia is suggested by elevated serum TNFα and high levels of spontaneous TNFα production in peripheral blood monocytes from patients {Wright et al., J. Immunol. 141(1), 99-104 (1988)}. TNFα has been implicated in various roles with other viral infections, such as the cytomegalia virus (CMV), influenza virus, adenovirus, and the herpes family of viruses for similar reasons as those noted.

The nuclear factor κB (NFκB) is a pleiotropic transcriptional activator (Lenardo, et al., Cell 1989, 58, 227-29). NFκB has been implicated as a transcriptional activator in a variety of disease and inflammatory states and is thought to regulate cytokine levels including but not limited to TNFα and also to be an activator of HIV transcription (Dbaibo, et al., J. Biol. Chem. 1993, 17762-66; Duh et al., Proc. Natl. Acad.

Sci. 1989, 86, 5974-78; Bachelerie et al., Nature 1991, 350, 709-12; Boswas et al., J Acquired Immune Deficiency Syndrome 1993, 6, 778-786; Suzuki et al., Biochem. And Biophys. Res. Comm. 1993, 193, 277-83; Suzuki et al., Biochem. And Biophys. Res. Comm. 1992, 189, 1709-15; Suzuki et al., Biochem. Mol. Bio. Int. 1993, 31(4), 693-700; Shakhov et al., Proc. Natl. Acad. Sci. USA 1990, 171, 35-47; and Staal et al., Proc. Natl. Acad. Sci. USA 1990, 87, 9943-47). Thus, inhibition of NFκB binding can regulate transcription of cytokine gene(s) and through this modulation and other mechanisms be useful in the inhibition of a multitude of disease states. The compounds described herein can inhibit the action of NFκB in the nucleus and thus are useful in the treatment of a variety of diseases including but not limited to rheumatoid arthritis, rheumatoid spondylitis, osteoarthritis, other arthritic conditions, cancer, septic shock, sepsis, endotoxic shock, graft versus host disease, wasting, Crohn's disease, inflammatory bowel disease, ulcerative colitis, multiple sclerosis, systemic lupus erythrematosis, ENL in leprosy, HIV, AIDS, and opportunistic infections in AIDS. TNFα and NFκB levels are influenced by a reciprocal feedback loop. As noted above, the compounds of the present invention affect the levels of both TNFα and NFκB.

Many cellular functions are mediated by levels of adenosine 3',5'-cyclic monophosphate (cAMP). Such cellular functions can contribute to inflammatory conditions and diseases including asthma, inflammation, and other conditions (Lowe and Cheng, Drugs of the Future, 17(9), 799-807, 1992). It has been shown that the elevation of cAMP in inflammatory leukocytes inhibits their activation and the subsequent release of inflammatory mediators, including TNFα and NFκB. Increased levels of cAMP also leads to the relaxation of airway smooth muscle.

The primary cellular mechanism for the inactivation of cAMP is the breakdown of cAMP by a family of isoenzymes referred to as cyclic nucleotide phosphodiesterases (PDE) (Beavo and Reitsnyder, Trends in Pharm., 11, 150-155, 1990). There are seven known members of the family of PDEs. It is recognized, for example, that the inhibition of PDE type IV is particularly effective in both the inhibition of inflammatory mediator release and the relaxation of airway smooth muscle (Verghese, et al., Journal of Pharmacology and Experimental Therapeutics, 272(3), 1313-1320, 1995). Thus, compounds that inhibit PDE IV specifically, would exhibit the desirable inhibition of inflammation and relaxation of airway smooth muscle with a minimum of unwanted side effects, such as cardiovascular or anti-platelet effects. Currently used PDE IV inhibitors lack the selective action at acceptable therapeutic doses. The compounds of the present invention are useful in the inhibition of phosphodiesterases, particularly PDE III and PDE IV, and in the treatment of disease states mediated thereby.

Decreasing TNFα levels, increasing cAMP levels, and inhibiting PDE IV thus constitute valuable therapeutic strategies for the treatment of many inflammatory, infectious, immunological or malignant diseases. These include but are not restricted to septic shock, sepsis, endotoxic shock, hemodynamic shock and sepsis syndrome, post ischemic reperfusion injury, malaria, mycobacterial infection, meningitis, psoriasis, congestive heart failure, fibrotic disease, cachexia, graft rejection, cancer, autoimmune disease, opportunistic infections in AIDS, rheumatoid arthritis, rheumatoid spondylitis, osteoarthritis, other arthritic conditions, Crohn's disease, ulcerative colitis, multiple sclerosis, systemic lupus erythrematosis, ENL in leprosy, radiation damage, and hyperoxic alveolar injury.

DETAILED DESCRIPTION

The present invention pertains to compounds of Formula I in which the carbon atom designated * constitutes a center of chirality:

I

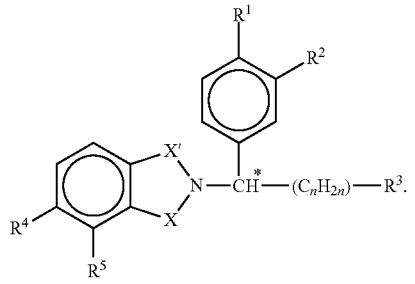

In Formula I, each of $R^1$ and $R^2$, independently of the other, is alkyl of 1 to 4 carbon atoms, alkoxy of 1 to 4 carbon atoms, cyano, cycloalkoxy of 3 to 18 carbon atoms, cycloalkyl of 3 to 18 carbon atoms, or cycloalkylmethoxy in which cycloalkyl has from 3 to 18 carbon atoms, one of X and X' is ═C═O or ═$SO_2$ and the other of X and X' is a divalent group selected from ═C═O, ═$CH_2$, ═$SO_2$ or ═$CH_2$C═O, n has a value of 1, 2, or 3;

$R^3$ is —$SO_2$—Y, —COZ, —CN, or hydroxyalkyl of 1 to 6 carbon atoms in which

Y is alkyl of 1 to 6 carbon atoms, phenyl, or benzyl,

Z is —$NR^{6''}R^{7''}$, alkyl of 1 to 6 carbon atoms, phenyl, or benzyl, $R^{6''}$ is hydrogen, alkyl of 1 to 4 carbon atoms, cycloalkyl of 3 to 18 carbon atoms; phenyl, benzyl, or alkanoyl of 2 to 5 carbon atoms, each of which is unsubstituted or substituted with halo, amino, or alkylamino of 1 to 4 carbon atoms, and $R^{7''}$ is hydrogen or alkyl of 1 to 4 carbon atoms, $R^4$ and $R^5$, when taken together, are —NH—$CH_2$—$R^8$—, —NH—CO—$R^8$— or —N═CH—$R^8$— in which —$R^8$— is —$CH_2$—, —O—, —NH—, —CH═CH—, —CH═N—, or —N═CH—.

Alternatively, when taken independently of each other, one of $R^4$ and $R^5$ is hydrogen and the other of $R^4$ and $R^5$ is imidazolyl, pyrrolyl; oxadiazolyl, triazolyl, or

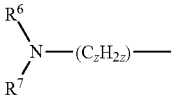

in which z is 0 or 1, $R^6$, when taken independently of $R^7$, is hydrogen; alkyl of 1 to 4 carbon atoms, cycloalkyl of 3 to 18 carbon atoms, alkanoyl of 2 to 5 carbon atoms, or cycloalkanoyl of 2 to 6 carbon atoms, each of which is unsubstituted or substituted with halo, amino, monoalkylamino or dialkylamino in which each alkyl group contains 1 to 4 carbon atoms; phenyl; benzyl; benzoyl; alkoxycarbonyl of 2 to 5 carbon atoms; N-morpholinocarbonyl; carbamoyl; alkoxyalkylcarbonyl of 2 to 5 carbon atoms; N-substituted carbamoyl in which the substituent is alkyl of 1 to 4 carbon atoms, cycloalkyl of 3 to 18 carbon atoms, or alkanoyl of 2 to 5 carbon atoms, each of which is unsubstituted or substituted with halo, amino, monoalkylamino or dialkylamino in which each alkyl group contains 1 to 4 carbon atoms; phenyl; benzyl; or methylsulfonyl; and $R^7$ is hydrogen, alkyl of 1 to 4 carbon atoms, or methylsulfonyl, or alkoxyalkylcarbonyl of 2 to 5 carbon atoms.

Preferably z is not 0 when (i) $R^3$ is —$SO_2$—Y—COZ, or —CN and (ii) $R^4$ or $R^5$ is hydrogen.

When taken together, $R^6$ and $R^7$ can be —CH═CH—CH═CH—, —CH═CH—N═CH—, or alkylidene of 1 or 2 carbon atoms substituted by amino, alkylamino, or dialkylamino in which each alkyl group has from 1 to 4 carbon atoms.

In addition, one of $R^4$ and $R^5$ is:

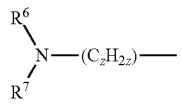

in which each of $R^6$, $R^7$, and z is as just define and the other of $R^4$ and $R^5$ is:

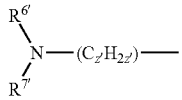

in which z' is 0 or 1; $R^{6'}$ has the same meaning as, but is selected independently of, $R^6$; and $R^{7'}$ has the same meaning as, but is selected independently of, $R^7$.

The present invention also pertains to the acid addition salts of these isoindoline derivatives which are susceptible of protonation. Such salts include those derived from organic and inorganic acids such as, without limitation, hydrochloric acid, hydrobromic acid, phosphoric acid, sulfuric acid, methanesulfonic acid, acetic acid, tartaric acid, lactic acid, succinic acid, citric acid, malic acid, maleic acid, sorbic acid, aconitic acid, salicylic acid, phthalic acid, embonic acid, enanthic acid, and the like.

The compounds preferrably are administered as a substantially chirally pure isomer, (S)- or (R)-, but can also be administered as a mixture of the (S)-isomer and the (R)-isomer.

The compounds can be prepared through a number of methods. Often it is advantageous to utilized protected groups including but not limited to functional groups convertible to the desired group. For example, the reactions described herein can be performed with intermediates in which either or both of $R^4$ and $R^5$ are nitro groups with the nitro group(s) then being catalytically reduced (hydrogenated) to an amine or diamine, as the case may be. Similarly, one can employ an intermediate in which either or both of $R^4$ and $R^5$ is a cyano group and the final compound can then be reduced to yield the corresponding aminomethyl compound. Likewise, the carbonyl comprised by $R^3$ can be processed in the form of a secondary alcohol which is thereafter is oxidized to the carbonyl compound, utilizing for example pyridinium chlorochromate.

Protecting groups utilized herein denote groups which generally are not found in the final therapeutic compounds but which are intentionally introduced at some stage of the synthesis in order to protect groups which otherwise might be altered in the course of chemical manipulations. Such protecting groups are removed or converted to the desired group at a later stage of the synthesis and compounds bearing such protecting groups thus are of importance primarily as chemical intermediates (although some derivatives also exhibit biological activity). Accordingly the precise structure of the protecting group is not critical. Numerous reactions for the formation and removal of such protecting groups are described in a number of standard works including, for example, "Protective Groups in Organic Chemistry", Plenum Press, London and New York, 1973; Greene, Th. W. "Protective Groups in Organic Synthesis", Wiley, New York, 1981; "The Peptides", Vol. I, Schröder and Lubke, Academic Press, London and New York, 1965; "Methoden der organischen Chemie", Houben-Weyl, 4th Edition, Vol. 15/I, Georg Thieme Verlag, Stuttgart 1974, the disclosures of which are incorporated herein by reference.

An amino group thus can be protected as an amide utilizing an acyl group which is selectively removable under mild conditions, especially formyl, a lower alkanoyl group which is branched in 1- or α position to the carbonyl group, particularly tertiary alkanoyl such as pivaloyl, or a lower alkanoyl group which is substituted in the position α to the carbonyl group, as for example trifluoroacetyl.

Should a carboxy group require protection, it can be converted to an ester which is selectively removable under sufficiently mild conditions not to disrupt the desired structure of the molecule, especially a lower alkyl ester of 1 to 12 carbon atoms such as methyl or ethyl and particularly one which is branched at the 1- or α position such as t-butyl; and such lower alkyl ester substituted in the 1- or 2-position with (i) lower alkoxy, such as for example, methoxymethyl, 1-methoxyethyl, and ethoxymethyl, (ii) lower alkylthio, such as for example methylthiomethyl and 1-ethylthioethyl; (iii) halogen, such as 2,2,2-trichlomethyl, 2-bromoethyl, and 2-iodoethoxycarbonyl; (iv) one or two phenyl groups each of which can be unsubstituted or mono-, di- or tri-substituted with, for example lower alkyl such as tert.-butyl, lower alkoxy such as methoxy, hydroxy, halo such as chloro, and nitro, such as for example, benzyl, 4-nitrobenzyl, diphenylmethyl, di-(4-methoxyphenyl)methyl; or (v) aroyl, such as phenacyl. A carboxy group also can be protected in the form of an organic silyl group such as trimethylsilylethyl or tri-lower alkylsilyl, as for example trimethylsilyloxycarbonyl.

Many, but not all, of the compounds described herein proceed through compounds in which either or both of $R^4$ and $R^5$ are amino or a protected amino group. The amino group is then further processed as hereinafter described. One can also employ a starting material in which $R^4$ and/or $R^5$ is an amide; e.g., 4-acetamidophthalic acid or 2-chloroacetamide. The product of the latter reaction then can be allowed to react with sodium azide followed by triphenylphosphine to yield a 2-amino-N-substituted acetamide.

In one embodiment, an anhydride or lactone is allowed to react with an α,3,4-trisubstituted benzylamine:

I

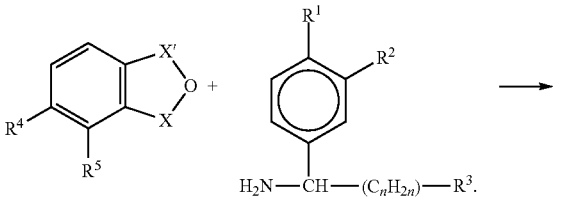

In the above, at least one of X and X' is ═C═O. One also can employ the diacid, e.g., an $R^{4'}$ $R^5$ disubstituted phthallic acid, and remove the water formed. Activated derivative thereof also can be employed.

The compounds in which X is ═$CH_2$ can be prepared from the same trisubstituted benzylamine and a formyl or bromomethyl benzoate derivative:

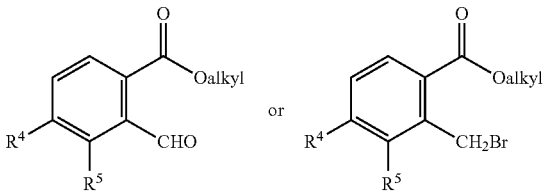

Analogously, an $R^4$,$R^5$ benzene ortho dialdehyde can be allowed to react with the above α,3,4-trisubstituted benzylamine in the form of the ammonium chloride salt.

The foregoing reactions also can be performed with compound in which $R^4$ and $R^5$ form a heterocylic ring. For example, using furano[3,4-h]quinoline-1,3-dione in place of phthallic acid anhydride, the corresponding, 2-substituted pyrrolino[3,4-h]quinoline-1,3-dione is obtained.

When in formula I $R^4$ and $R^5$ are both amino, the compound can be further reacted. Using dimethylformamide dimethyl acetal, for example, yields a pyrrolino[3,4-e]benzimidazole; i.e., $R^4$ and $R^5$ together are —N═CH—NH—. The corresponding hydropyrrolino[3,4-e]benzimidazole can be obtained from the diamine and triphosgene whereas if one instead employs the diamine and glyoxal, the product is the corresponding 3-pyrrolino[3,4-f]quinoxaline.

In the case of only one of $R^4$ and $R^5$ in formula I being amine, the same can be reacted with an appropriate acid halide or anhydride to yield the corresponding amide. The same reaction can be conducted using chloroformate to yield the methoxycarboxamide derivative.

If the amide is formed from the amine and chloroacetyl chloride, i.e., producing a chloroacetamide derivative, this can be followed by treatment with ammonia or a primary or secondary amine to yield the corresponding aminoacetamide; e.g., treatment with dimethylamine produces the corresponding dimethylaminoacetamide. A compound in which either or both of $R^4$ and $R^5$ is amino also can be subjected to reductive formylation to form the corresponding N,N-dimethylamino compound.

A compound in which either or both of $R^4$ and $R^5$ is amino also can be reacted with dimethylformamide dimethyl acetal to yield the corresponding 1-aza-2-(dimethylamino)vinyl compound.

Compounds in which one of $R^4$ and $R^5$ is a heterocyclic group can be prepared in number of ways. An isoindoline 4- or 5-carboxylic acid can be reacted with carbonyldiimidazole followed by acetic hydrazide to yield the corresponding 4-(5-methyl-1,3,4-oxadiazol-2-yl)isoindoline or 5-(5-methyl-1,3,4-oxadiazol-2-yl)isoindoline. Alternatively, a mono amine and 2,5-dimethoxytetrahydrofuran are allowed to react to yield 4- or 5-pyrrolylisoindoline. Similarly a 4-aminomethyl or 5-aminomethyl (prepared as described above) and dimethoxytetrahydrofuran are allowed to react to yield the corresponding pyrrolylmethyl compound.

A first preferred subgroup are those compounds of Formula I in which $R^4$ and $R^5$ together are —NH—$CH_2$—$R^8$—, —NH—CO—$R^8$— or —N═CH—$R^8$— in which —$R^8$— is —$CH_2$—, —O—, —NH—, —CH═CH—, —CH═N—, or —N═CH—. It will be appreciated that each of the chains that is not symmetrical can be arranged in either of two orientations, each of which is within the scope of this invention.

A second preferred subgroup are those compounds of Formula I in which one of $R^4$ and $R^5$ is hydrogen and the other of $R^4$ and $R^5$ is imidazolyl, oxadiazolyl, pyrrolyl, or triazolyl.

A third preferred subgroup are those compounds of Formula I in which one of $R^4$ and $R^5$ is:

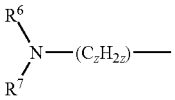

in which z is 0 or 1; $R^6$ when taken independently of $R^7$ is hydrogen, alkyl of 1 to 4 carbon atoms, haloalkyl of 1 to 4 carbon atoms, cycloalkyl of 3 to 18 carbon atoms; phenyl, benzyl, alkanoyl of 2 to 5 carbon atoms, haloalkanoyl of 2 to 5 carbon atoms, aminoalkanoyl of 2 to 5 carbon atoms, N-alkylaminoalkanoyl of 2 to 5 carbon atoms, benzoyl, alkoxycarbonyl of 2 to 5 carbon atoms, N-morpholinocarbonyl, carbamoyl, and N-substituted carbamoyl in which the substituent is alkyl of 1 to 4 carbon atoms, haloalkyl of 1 to 4 carbon atoms, cycloalkyl of 3 to 18 carbon atoms; aminoalkanoyl of 2 to 5 carbon atoms, N-alkylaminoalkanoyl of 2 to 5 carbon atoms, phenyl, benzyl, or methylsulfonyl; and $R^7$ is hydrogen or alkyl of 1 to 4 carbon atoms, or $R^6$ and $R^7$ taken together are —CH═CH—CH—CH—, —CH═CH—N═CH—, or alkylidene of 1 or 2 carbon atoms substituted by amino, alkylamino, or dialkylamino in which each alkyl group has from 1 to 4 carbon atoms.

Within this third preferred subgroup, a first further preferred subgroup are compounds in which $R^6$ is hydrogen, alkyl of 1 to 4 carbon atoms, haloalkyl of 1 to 4 carbon atoms, cycloalkyl of 3 to 18 carbon atoms; phenyl, or benzyl. A second further preferred subgroup are compounds in which $R^6$ is alkanoyl of 2 to 5 carbon atoms, haloalkanoyl of 2 to 5 carbon atoms, aminoalkanoyl of 2 to 5 carbon atoms, benzoyl, alkoxycarbonyl of 2 to 5 carbon atoms, N-morpholinocarbonyl, carbamoyl, and N-substituted carbamoyl in which the substituent is methyl, ethyl, or trifluoromethyl; and $R^7$ is hydrogen.

A fourth preferred subgroup are those compounds of Formula I in which one of $R^4$ and $R^5$ is:

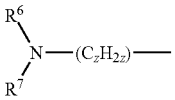

and the other of $R^4$ and $R^5$ is

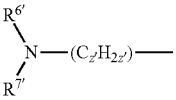

in which each of z and z' independently is 0 or 1; $R^6$ has the meaning given above, $R^{6'}$ has the same meaning as, but is selected independently of, $R^6$; $R^7$ has the meaning given above, and $R^{7'}$ has the same meaning as, but is selected independently of, $R^7$.

Within this fourth preferred subgroup, a first further preferred subgroup are compounds in which each of $R^6$ and $R^{6'}$, independently of the other, is hydrogen, alkyl of 1 to 4 carbon atoms, haloalkyl of 1 to 4 carbon atoms, cycloalkyl of 3 to 18 carbon atoms; phenyl, or benzyl. A second further preferred subgroup are compounds in which each of $R^6$ and $R^{6'}$, independently of the other, is alkanoyl of 2 to 5 carbon atoms, haloalkanoyl of 2 to 5 carbon atoms, aminoalkanoyl of 2 to 5 carbon atoms, benzoyl, alkoxycarbonyl of 2 to 5 carbon atoms, N-morpholinocarbonyl, carbamoyl, and N-substituted carbamoyl in which the substituent is methyl, ethyl, or trifluoromethyl; and each of $R^7$ and $R^{7'}$ is hydrogen.

A third further preferred subgroup are compounds in which one of $R^6$ and $R^{6'}$ is alkanoyl of 2 to 5 carbon atoms, haloalkanoyl of 2 to 5 carbon atoms, aminoalkanoyl of 2 to 5 carbon atoms, benzoyl, alkoxycarbonyl of 2 to 5 carbon atoms, N-morpholinocarbonyl, carbamoyl, and N-substituted carbamoyl in which the substituent is methyl, ethyl, or trifluoromethyl; and the other of $R^6$ and $R^{6'}$ is hydrogen, alkyl of 1 to 4 carbon atoms, haloalkyl of 1 to 4 carbon atoms, cycloalkyl of 3 to 18 carbon atoms; phenyl, or benzyl; and each of $R^7$ and $R^{7'}$ is hydrogen.

Additional preferred subgroups for all of the above are compounds in which one of X and X' is =C=O, and the other is =C=O, $=CH_2$, or $=SO_2$. and compounds in which each of $R^1$ and $R^2$, independently of the other, is methyl, ethyl, n-propyl, i-propyl, methoxy, ethoxy, n-propoxy, i-propoxy, cyclopentoxy, cyclohexoxy, cycloheptoxy, cyclopentyl, cyclohexyl, cycloheptyl, or cyclopropylmethoxy.

The compounds possess a center of chirality and thus can exist as optical isomers. Both the chirally pure (R)- and (S)-isomers as well as mixtures (including but not limited to racemic mixtures) of these isomers, as well as diastereomers when there are two chiral centers, are within the scope of the present invention. Mixtures can be used as such or can be separated into their individual isomers mechanically as by chromatography using a chiral absorbent. Alternatively, the individual isomers can be prepared in chiral form or separated chemically from a mixture by forming salts with a chiral acid, or have such as the individual enantiomers of 10-camphorsulfonic acid, camphoric acid, bromocamphoric acid, methoxyacetic acid, tartaric acid, diacetyltartaric acid, malic acid, pyrrolidone-5-carboxylic acid, and the like, and then freeing one or both of the resolved bases, optionally repeating the process, so as obtain either or both substantially free of the other; i.e., in a form having an optical purity of >95%.

Inhibition of PDE III, PDE IV, TNFα and NFκB by these compounds can be conveniently assayed using methods known in the art, e.g., enzyme immunoassay, radioimmunoassay, immunoelectrophoresis, affinity labeling, etc., of which the following are typical.

PBMC from normal donors are obtained by Ficoll-Hypaque density centrifugation. Cells are cultured in RPMI supplemented with 10% AB+ serum, 2 mM L-glutamine, 100 U/mL penicillin and 100 mg/mL streptomycin.

The test compounds are dissolved in dimethylsulfoxide (Sigma Chemical), further dilutions are done in supplemented RPMI. The final dimethylsulfoxide concentration in the presence or absence of drug in the PBMC suspensions is 0.25 wt %. The test compounds are assayed at half-log dilutions starting at 50 mg/mL. The test compounds are added to PBMC ($10^6$ cells/mL) in 96 wells plates one hour before the addition of LPS.

PBMC ($10^6$ cells/mL) in the presence or absence of test compound are stimulated by treatment with 1 mg/mL of LPS from Salmonella minnesota R595 (List Biological Labs, Campbell, Calif.). Cells are then incubated at 37° C. for 18-20 hours. Supernatants are harvested and assayed immediately for TNFα levels or kept frozen at −70° C. (for not more than 4 days) until assayed.

The concentration of TNFα in the supernatant is determined by human TNFα ELISA kits (ENDOGEN, Boston, Mass.) according to the manufacturer's directions.

Phosphodiesterase can be determined in conventional models. For example, using the method of Hill and Mitchell, U937 cells of the human promonocytic cell line are grown to $1\times10^6$ cells/mL and collected by centrifugation. A cell pellet of $1\times10^9$ cells is washed in phosphate buffered saline and then frozen at −70° C. for later purification or immediately lysed in cold homogenization buffer (20 mM Tris-HCl, pH 7.1, 3 mM 2-mercaptoethanol, 1 mM magnesium chloride, 0.1 mM ethylene glycol-bis-(β-aminoethyl ether)-N,N,N',N'-tetraacetic acid (EGTA), 1 μM phenylmethylsulfonyl fluoride (PMSF), and 1 μg/mL leupeptin). Cells are homogenized with 20 strokes in a Dounce homogenizer and supernatant containing the cytosolic fraction are obtained by centrifugation. The supernatant then is loaded onto a Sephacryl S-200 column equilibrated in homogenization buffer. Phosphodiesterase is eluted in homogenization buffer at a rate of approximately 0.5 mL/min and fractions are assayed for phosphodiesterase activity−/+rolipram. Fractions containing phosphodiesterase activity (rolipram sensitive) are pooled and aliquoted for later use.

The phosphodiesterase assay is carried out in a total volume of 100 μl containing various concentration of test compounds, 50 mM Tris-HCl, pH 7.5, 5 mM magnesium chloride, and 1 μM cAMP of which 1% was $^3$H cAMP. Reactions are incubated at 30° C. for 30 minutes and terminated by boiling for 2 minutes. The amount of phosphodiesterase IV containing extract used for these experiments is predetermined such that reactions are within the linear range and consumed less than 15% of the total substrate. Following termination of reaction, samples are chilled at 4° C. and then treated with 100 μl 10 mg/mL snake venom for 15 min at 30° C. Unused substrate then is removed by adding 200 μl of a quaternary ammonium ion exchange resin (AG1-X8, Bio-Rad) for 15 minutes. Samples then are spun at 3000 rpm, 5 min and 50 μl of the aqueous phase are taken for counting. Each data point is carried out in duplicate and activity is expressed as percentage of control. The $IC_{50}$ of the compound then is determined from dose response curves of a minimum of three independent experiments.

The compounds can be used, under the supervision of qualified professionals, to inhibit the undesirable effects of TNFα, NFκB, and phosphodiesterase. The compounds can be administered orally, rectally, or parenterally, alone or in combination with other therapeutic agents including antibiotics, steroids, etc., to a mammal in need of treatment. Oral dosage forms include tablets, capsules, dragees, and similar shaped, compressed pharmaceutical forms. Isotonic saline solutions containing 20-100 milligrams/milliliter can be used for parenteral administration which includes intramuscular, intrathecal, intravenous and intra-arterial routes of administration. Rectal administration can be effected through the use of suppositories formulated from conventional carriers such as cocoa butter.

Dosage regimens must be titrated to the particular indication, the age, weight, and general physical condition of the patient, and the response desired but generally doses will be from about 1 to about 1000 milligrams/day as needed in single or multiple daily administration. In general, an initial treatment regimen can be copied from that known to be effective in interfering with TNFα activity for other TNFα mediated disease states by the compounds of the present invention.

Treated individuals will be regularly checked for T cell numbers and T4/T8 ratios and/or measures of viremia such as levels of reverse transcriptase or viral proteins, and/or for progression of cytokine-mediated disease associated problems such as cachexia or muscle degeneration. If no effect is observed following the normal treatment regimen, then the amount of cytokine activity interfering agent administered is increased, e.g., by fifty percent a week.

The compounds of the present invention can also be used topically in the treatment or prophylaxis of topical disease states mediated or exacerbated by excessive TNFα production, such as viral infections, for example those caused by the herpes viruses or viral conjunctivitis, psoriasis, other skin disorders and diseases, etc.

The compounds can also be used in the veterinary treatment of mammals other than humans in need of prevention or inhibition of TNFα production. TNFα mediated diseases for treatment, therapeutically or prophylactically, in animals include disease states such as those noted above, but in particular viral infections. Examples include feline immunodeficiency virus, equine infectious anaemia virus, caprine arthritis virus, visna virus, and maedi virus, as well as other lentiviruses.

The invention thus includes various methods of treatment including the method of inhibiting PDE IV, the method of reducing or inhibiting undesirable levels of TNFα, method of reducing or inhibiting undesirable levels of matrix metalloproteinases, the method of treating undesirable angiogenesis, the method of treating cancer, the method of treating inflammatory disease, the method of treating autoimmune disease, the method of treating arthritis, the method of treating rheumatoid arthritis, the method of treating inflammatory bowel disease, the method of treating Crohn's disease, the method of treating aphthous ulcers, the method of treating cachexia, the method of treating graft versus host disease, the method of treating asthma, the method of treating adult respiratory distress syndrome, and the method of treating acquired immune deficiency syndrome, by administering to a mammalan an effective amount of a substantially chirally pure (R)- or (S)-isomer of a compound of Formula I or a mixture of those isomers. While these methods may overlap, they also may differ in terms of method of administration, dose level, dosage regimen (such as single or multiple doses), and concurrently administered therapeutic agents.

The invention also includes pharmaceutical compositions in which (i) a quantity of a substantially chirally pure (R)- or (S)-isomer of a compound of Formula I or a mixture of those isomers, that upon administration in a single or multiple dose regimen is pharmaceutically effective is combined with (ii) a pharmaceutically acceptable carrier.

Pharmaceutical compositions can be typified by oral dosage forms that include tablets, capsules, dragees, and similar shaped, compressed pharmaceutical forms containing from 1 to 100 mg of drug per unit dosage. Mixtures containing from 20 to 100 mg/mL can be formulated for parenteral administration which includes intramuscular, intrathecal, intravenous and intra-arterial routes of administration. Rectal administration can be effected through the use of suppositories formulated from conventional carriers such as cocoa butter.

Pharmaceutical compositions will comprise one or more compounds of the present invention associated with at least one pharmaceutically acceptable carrier, diluent or excipient. In preparing such compositions, the active ingredients are usually mixed with or diluted by an excipient or enclosed within such a carrier which can be in the form of a capsule or sachet. When the excipient serves as a diluent, it may be a solid, semi-solid, or liquid material which acts as a vehicle, carrier, or medium for the active ingredient. Thus, the compositions can be in the form of tablets, pills, powders, elixirs, suspensions, emulsions, solutions, syrups, soft and hard gelatin capsules, suppositories, sterile injectable solutions and sterile packaged powders. Examples of suitable excipients include lactose, dextrose, sucrose, sorbitol, mannitol, starch, gum acacia, calcium silicate, microcrystalline cellulose, polyvinylpyrrolidinone polyvinylpyrrolidone, cellulose, water, syrup, and methyl cellulose, the formulations can additionally include lubricating agents such as talc, magnesium stearate and mineral oil, wetting agents, emulsifying and suspending agents, preserving agents such as methyl- and propylhydroxybenzoates, sweetening agents or flavoring agents.

The compositions preferably are formulated in unit dosage form, meaning physically discrete units suitable as a unitary dosage, or a predetermined fraction of a unitary dose to be administered in a single or multiple dosage regimen to human subjects and other mammals, each unit containing a predetermined quantity of active material calculated to produce the desired therapeutic effect in association with a suitable pharmaceutical excipient. The compositions can be formulated so as to provide an immediate, sustained or delayed release of active ingredient after administration to the patient by employing procedures well known in the art.

The following examples will serve to further typify the nature of this invention but should not be construed as a limitation in the scope thereof, which scope is defined solely by the appended claims.

Example 1

2-[1-(3-Ethoxy-4-methoxyphenyl)-2-methylsulfonylethyl]-4,5-dinitroisoindoline-1,3-dione A mixture of 3,4-dinitrophthalic acid (4.63 g, 18.1 mmol) and 2-(3-ethoxy-4-methoxyphenyl)-1-(methylsulfonyl)eth-2-ylamine (4.94 g, 18.1 g) in toluene (70 mL) was heated to reflux for 15 hours. The water was removed by a Dean-Stark trap. To the reaction mixture was added ethyl acetate (150 mL). The organic layer was extracted with water, sodium hydrogen carbonate (sat), brine (100 mL each), and dried over magnesium sulfate. The solvent was removed in vacuo to give a solid. The solid was recrystallized from ethanol (300 mL) to give 2-[1-(3-ethoxy-4-methoxyphenyl)-2-methylsulfonylethyl]-4,5-dinitroisoindoline-1,3-dione as an orange solid (4.35 g, 49% yield): mp, 122.0-124.0° C.; $^1$H NMR ($CDCl_3$) δ 1.47 (t, J=6.9 Hz, 3H, $CH_3$), 2.93 (s, 3H, $CH_3$), 3.65 (dd, J=3.9, 14.3 Hz, 1H, CHH), 3:86 (s, 3H, $CH_3$), 4.10 (q, J=6.9 Hz, 2H, $CH_2$), 4.56 (dd, J=11.4, 14.1 Hz, 1H, CHH), 5.90 (dd, J=3.9, 11.1 Hz, 1H, NCH), 6.84 (d, J=8.0 Hz, 1H, Ar), 7.07-7.11 (m, 2H, Ar), 8.16 (d, J=8.2 Hz, 1H, Ar), 8.60 (d, J=7.9 Hz, 1H, Ar); $^{13}$C NMR ($CDCl_3$ ) δ 14.66, 41.66, 49.57, 53.38, 55.98, 64.61, 111.61, 112.42, 120.64, 123.93, 126.18, 127.85, 131.93, 136.74, 138.10, 142.45, 148.77, 150.17, 161.57, 163.47; Anal Calcd for $C_{20}H_{19}N_3O_{10}S$+0.1 ethyl acetate: C, 48.78; H, 3.97; N, 8.37. Found: C, 48.50; H, 3.77; N, 8.07. (HNMR showed the sample contained ~10% eq of ethyl acetate).

Example 2

2-[1-(3-Ethoxy-4-methoxyphenyl)-2-methylsulfonylethyl]-4,5-diaminoisoindoline-1,3-dione A mixture of 2-[1-(3-ethoxy-4-methoxyphenyl)-2-methylsulfonylethyl]-4,5-dinitroisoindoline-1,3-dione (4.35 g, 8.81 mmol) and Pd/C (800 mg) in ethyl acetate (200 mL) was shaken under hydrogen (50-60 psi) in a Parr bottle for 16 hours. The suspension was filtered through a pad of Celite filter material. The Celite filter material was washed with acetone (200 mL). The solvent was removed in vacuo to give a solid. The solid was stirred in ethyl acetate (10 mL) for 2 hours. The suspension was filtered to give 2-[1-(3-ethoxy-4-methoxyphenyl)-2-methylsulfonylethyl]-4,5-diaminoisoindoline-1,3-dione as a yellow solid (2.79 g, 73% yield): mp, 205-207° C.; $^1$H NMR (DMSO-d6) δ 1.32 (t, J=6.9 Hz, 3H, $CH_3$), 2.99 (s, 3H, $CH_3$), 3.73 (s, 3H, $CH_3$), 3.95-4.07 (m, 3H, CHH), 4.37 (dd, J=10.4, 14.0 Hz, 1H, CHH), 5.67 (dd, J=3.9, 10.2 Hz, 1H, NCH), 5.90-6.00 (m, 4H, $2NH_2$), 6.64 (d, J=7.7 Hz, 1H, Ar), 6.88-6.92 (m, 3H, Ar), 7.06 (s, 1H, Ar); $^{13}$C NMR ($CDCl_3$) δ 14.64, 40.94, 46.65, 53.53, 55.46, 63.79, 109.36, 111.74, 112.29, 114.42, 117.04, 119.55, 130.68, 133.98, 134.06, 142.38, 147.74, 148.63, 167.16, 169.38; Anal Calcd for $C_{20}H_{23}N_3O_6S$: C, 55.42; H, 5.35; N, 9.69. Found: C, 55.71; H, 5.30; N, 9.29. MS: 434 ($M^+$+1), 456 ($M^+$+23 Na).

Example 3

7-[1-(3-Ethoxy-4-methoxyphenyl)-2-methylsulfonylethyl]-3-pyrrolino[3,4-e]benzimidazole-6,8-dione To a solution of 2-[1-(3-ethoxy-4-methoxyphenyl)-2-methylsulfonylethyl]-4,5-diaminoisoindoline-1,3-dione (310 mg, 0.72 mmol) in acetic acid (5 mL) was added dimethylformamide dimethyl acetal (3 mL). The solution was heated to reflux for 17 hours. The solvent was removed in vacuo to give an oil. The oil was stirred in sodium hydrogen carbonate (50 mL, sat.) and ethyl acetate (100 mL). The organic layer was separated, washed with brine (50 mL), and dried over magnesium sulfate. The solvent was removed in vacuo to give an oil. The oil was separated by chromatography (silica gel, 7:13:0.5 methylene chloride:ethyl acetate:MeOH) to give 7-[1-(3-ethoxy-4-methoxyphenyl)-2-methylsulfonylethyl]-3-pyrrolino[3,4-e]benzimidazole-6,8-dione as a white solid (220 mg, 69% yield): mp, 143-145° C.; $^1$H NMR (DMSO-d6) δ 1.32 (t, J=6.9 Hz, 3H, $CH_3$), 3.02 (s, 3H, $CH_3$), 3.73 (s, 3H, $CH_3$), 4.02 (q, J=6.9 Hz, 2H, $CH_2$), 4.15 (dd, J=4.3, 14.3 Hz, 1H, CHH), 4.40 (dd, J=10.5, 14.3 Hz, 1H, CHH), 5.81 (dd, J=4.3, 10.4 Hz, 1H, NCH), 6.92-7.01 (m, 2H, Ar), 7.12 (s, 1H, Ar), 7.67 (d, J=8.2 Hz, 1H, Ar), 8.02 (d, J=8.0 Hz, 1H, Ar), 8.62 (s, 1H, CH), 13.49 (s, 1H, NH); $^{13}$C NMR (DMSO-d6) δ 14.64, 41.02, 47.17, 53.24, 55.46, 63.81, 111.78, 112.33, 116.34, 119.67, 125.84, 129.98, 147.64, 147.85, 148.79, 166.63, 168.23; Anal Calcd for $C_{21}H_{21}N_3O_6S$: C, 54.23; H, 5.07; N, 9.03. Found: C, 54.13; H, 4.65; N, 8.76; MS: 444 ($M^+$+1), 466 ($M^+$+23 Na).

Example 4

7-[1-(3-Ethoxy-4-methoxyphenyl)-2-methylsulfonylethy]hydro-3-pyrrolino[3,4-e]benzimidazole-2,6,8-trione To a solution of 2-[1-(3-ethoxy-4-methoxyphenyl)-2-methylsulfonylethyl]-4,5-diaminoisoindoline-1,3-dione (600 mg, 1.38 mmol) in methylene chloride (1 mL) was added triphosgene (0.43 g, 1.4 mmol) at room temperature and kept for 30 minutes. To the mixture was added sodium hydrogen carbonate (50 mL, sat.) and ethyl acetate (80 mL). The organic layer was washed with brine (50 mL) and dried over magnesium sulfate. The solvent was removed in vacuo to give a solid. The solid was then recrystallized from ethanol to give 7-[1-(3-ethoxy-4-methoxyphenyl)-2-methylsulfonylethyl] hydro-3-pyrrolino[3,4-e]-benzimidazole-2,6,8-trione as a brown solid (390 mg, 62% yield). mp, 242-244° C.; $^1$H NMR (DMSO-d6) δ 1.32 (t, J=6.9 Hz, 3H, $CH_3$), 3.01 (s, 3H, $CH_3$), 3.73 (s, 3H, $CH_3$), 4.01 (q, J=6.9 Hz, 2H, $CH_2$), 4.11 (dd, J=4.3, 14.3 Hz, 1H, CHH), 4.37 (dd, J=10.7, 14.3 Hz, 1H, CHH), 5.76 (dd, J=4.1, 10.3 Hz, 1H, NCH), 6.91-6.92 (m, 2H, Ar), 7.08 (s, 1H, Ar), 7.23 (d, J=7.7 Hz, 1H, Ar), 7.45 (d, J=7.8 Hz, 1H, Ar), 11.47 (s, 1H, NH), 11.87 (s, 1H, NH); $^{13}$C NMR (DMSO-d6) δ 14.64, 41.01, 47.07, 53.14, 55.46, 63.83, 110.41, 111.78, 112.00, 112.37 116.72, 119.67, 122.79, 125.76, 129.96, 136.29, 147.81, 148.80, 155.86, 166.11, 167.59; Anal Calcd for $C_{21}H_{21}N_3O_7S$+1.1$H_2O$: C, 52.63; H, 4.88; N, 8.77; $H_2O$, 4.13. Found: C, 52.48; H, 4.73; N, 8.53; $H_2O$, 4.07.

Example 5

2-[1-(3-Ethoxy-4-methoxyphenyl)-2-methylsulfonylethyl]-3-pyrrolino[3,4-h]quinoline-1,3-dione A mixture of 2-(3-ethoxy-4-methoxyphenyl)-1-(methylsulfonyl)eth-2-ylamine (0.69 g, 2.5 mmol), furano[3,4-h]quinoline-1,3-dione (0.50 g, 2.5 mmol) and sodium acetate (0.25 g, 3.1 mmol) in acetic acid (10 mL) was heated to reflux for 18 hours. The solvent was removed in vacuo to give an oil. The resulting oil was stirred in ether/hexane/water (30/5/30 mL) for 18 hours. The suspension was filtered to give a solid. The solid was stirred in hot methanol. The suspension was filtered to give 2-[1-(3-ethoxy-4-methoxyphenyl)-2-methylsulfonylethyl]-3-pyrrolino[3,4-h]quinoline-1,3-dione as an off-white solid (0.8 g, 70% yield): mp, 223-225° C.; $^1$H NMR ($CDCl_3$); δ 1.47 (t, J=6.8 Hz, 3H, $CH_3$), 2.89 (s, 3H, $CH_3$), 3.79-3.86 (m, 1H, CHH), 3.84 (s, 3H, $CH_3$), 4.12 (q, J=6.9 Hz, 2H, $CH_2$), 4.63 (dd, J=10.4, 14.3 Hz, 1H, CHH), 5.98 (dd, J=4.5, 10.3 Hz, 1H, NCH), 6.82-6.85 (m, 1H, Ar), 7.19-7.22 (m, 2H, Ar), 7.57 (dd, J=4.2, 8.4 Hz, 1H, Ar), 7.95 (t, J=8.2 Hz, 1H, Ar), 8.17 (d, J=8.3 Hz, 1H, Ar), 8.27 (dd, J=1.4, 8.4 Hz, 1H, Ar), 9.24 (dd, J=1.7, 4.2 Hz, 1H, Ar); $^{13}$C NMR ($CDCl_3$) δ 14.61, 41.36, 48.90, 54.73, 55.88, 64.47, 11.41, 112.57, 119.55, 120.55, 123.20, 126.89, 129.48, 132.19, 134.43, 135.69, 136.68, 142.79, 148.55, 149.59, 154.30, 167.11, 167.62; Anal Calcd for $C_{23}H_{22}N_2O_6S$: C, 60.78; H, 4.88; N, 6.16. Found: C, 60.57; H, 4.79; N, 5.95.

Example 6

2-[1-(3-Ethoxy-4-methoxyphenyl)-2-methylsulfonylethyl]-3-pyrrolino[3,4-f]quinoxaline-1,3-dione To a solution of 2-[1-(3-ethoxy-4-methoxyphenyl)-2-methylsulfonylethyl]-4,5-diaminoisoindoline-1,3-dione (433 mg, 1.0 mmol) in tetrahydrofuran (2 mL) was added glyoxal (0.15 mL, 1.3 mmol). The solution was heated to reflux for 7 hours. To the suspension was added ether (10 mL). The suspension was filtered and washed with ether to give an orange solid. The solid was stirred in ethanol (20 mL) for 18 hours. The suspension was filtered and washed with ethanol to give 2-[1-(3-ethoxy-4-methoxyphenyl)-2-methylsulfonylethyl]-3-pyrrolino[3,4-]quinoxaline-1,3-dione as an orange solid (200 mg, 44% yield): mp, 122.0-124.0° C.; $^1$H NMR (DMSO-d6) δ 1.32 (t, J=6.9 Hz, 3H, $CH_3$), 3.03 (s, 3H, $CH_3$), 3.73 (s, 3H, $CH_3$), 4.03 (q, J=6.9 Hz, 2H, $CH_2$), 4.20 (dd, J=4.5, 14.4 Hz, 1H, CHH) 4.39 (dd, J=10.5, 14.1 Hz, 1H, CHH), 5.87 (dd, J=4.5, 10.2 Hz, 1H, NCH), 6.92-6.96 (m, 1H, Ar), 7.03-7.07 (m, 1H, Ar), 7.15 (d, J=1.7 Hz, 1H, Ar), 8.23 (d, J=8.4 Hz, 1H, Ar), 8.53 (d, J=8.4 Hz, 1H, Ar), 9.14 (d, J=1.7 Hz, 1H, Ar), 9.22 (d, J=1.7 Hz, 1H, Ar); $^{13}$C NMR (DMSO-d6) δ 14.63, 41.05, 47.49, 53.07, 55.47, 63.81, 111.73, 112.41, 119.80, 122.66, 126.93, 129.48, 134.08, 137.06, 137.25, 145.02, 147.87, 147.93, 148.87, 148.96, 165.37, 167.05; Anal Calcd for $C_{22}H_{21}N_3O_6S$+0.2$H_2O$: C, 57.56; H, 4.70; N, 9.15; $H_2O$, 0.78. Found: C, 57.34; H, 4.70; N, 9.15; $H_2O$, 0.41.

Example 7

Cyclopropyl-N-{2-[1-(3-ethoxy-4-methoxyphenyl)-2-methylsulfonylethyl]-1,3-dioxoisoindolin-4-yl}carboxamide A mixture of 2-[1-(3-ethoxy-4-methoxyphenyl)-2-methylsulfonylethyl]-4-aminoisoindoline-1,3-dione (570 mg, 1.4 mmol) and cyclopropane carbonyl chloride (2 mL) was heated to reflux for 15 minutes. To the mixture was added methanol (20 mL) and water (5 mL) at room temperature and kept for 30 minutes. The solvent was removed in vacuo to give an oil. The oil was stirred in ether/hexane (15 mL each) for 1 hour to give a suspension. The suspension was filtered and washed with ether to give a yellow solid. The solid was then stirred in ethanol (10 mL) overnight. The suspension was filtered and washed with ethanol to give cyclopropyl-N-{2-[1-(3-ethoxy-4-methoxyphenyl)-2-methylsulfonylethyl]-1,3-dioxoisoindolin-4-yl}carboxamide as a yellow solid (380 mg, 57.4% yield); mp, 153-155° C.; $^1$H NMR ($CDCl_3$) δ 0.92-0.99 (m, 2H, 2CHH), 1.11-1.17 (m, 2H, 2CHH), 1.48 (t, J=6.9 Hz, 3H, $CH_3$), 1.61-1.71 (m, 1H, CH), 2.88 (s, 3H, $CH_3$), 3.75 (dd, J=4.4, 14.3 Hz, 1H, CHH), 3.86 (s, 3H, $CH_3$), 4.12 (q, J=7.1 Hz, 2H, $CH_2$), 4.57 (dd, J=10.4, 14.3 Hz, 1H, CHH), 5.89 (dd, J=4.4, 10.3 Hz, 1H, NCH), 6.84-6.88 (m, 1H, Ar), 7.11-7.15 (m, 2H, Ar), 7.48 (d, J=7.2 Hz, 1H, Ar), 7.65 (t, J=7.4 Hz, 1H, Ar), 8.76 (d, J=8.5 Hz, 1H, Ar), 9.69 (s, 1H, NH); $^{13}$C NMR ($CDCl_3$) δ 8.71, 14.62, 16.16, 41.58, 48.59, 54.60, 55.89, 64.50, 111.49, 112.44, 114.83, 117.91, 120.26, 124.99, 129.27, 130.99, 136.02, 137.77, 148.63, 149.76, 167.49, 169.52, 172.79; Anal Calcd for $C_{24}H_{26}N_2O_7S$: C, 59.25; H, 5.39; N, 5.76. Found: C, 59.06; H, 5.30; N, 5.69.

Example 8

2-Chloro-N-{2-[1-(3-ethoxy-4-methoxyphenyl)-2-methylsulfonylethyl]-1,3-dioxoisoindolin-4-yl}acetamide A mixture of 2-[1-(3-ethoxy-4-methoxyphenyl)-2-methylsulfonylethyl]-4-aminoisoindoline-1,3-dione (2.0 g, 4.8 mmol) and chloroacetyl chloride (2 mL, 25 mmol) was heated to reflux for 30 minutes. The solvent was removed in vacuo to give a solid. The solid was stirred in ether (40 mL) for 1 hour to give a suspension. The suspension was filtered and washed with ether to give 2-chloro-N-{2-[1-(3-ethoxy-4-methoxyphenyl)-2-methylsulfonylethyl]-1,3-dioxoisoindolin-4-yl}acetamide as a white solid (2.28 g, 96% yield); mp, 166-168° C.; $^1$H NMR ($CDCl_3$) δ 1.48 (t, J=6.9 Hz, 3H, $CH_3$), 2.88 (s, 3H, $CH_3$), 3.75 (dd, J=4.4, 14.3 Hz, 1H, CHH), 3.86 (s, 3H, $CH_3$), 4.13 (q, J=7.0 Hz, 2H, $CH_2$), 4.24 (s, 2H, $CH_2$), 4.57 (dd, J=10.5, 14.3 Hz, 1H, CHH), 5.89 (dd, J=4.5, 10.3 Hz, 1H, NCH), 6.84-6.88 (m, 1H, Ar), 7.11-7.15 (m, 2H, Ar), 7.57 (d, J=7.2 Hz, 1H, Ar), 7.70 (t, J=7.6 Hz, 1H, Ar), 8.77 (d, J=8.3 Hz, 1H, Ar), 10.53 (s, 1H, NH); $^{13}$C NMR ($CDCl_3$) δ 14.60, 41.52, 42.67, 48.72, 54.51, 55.88, 64.48, 111.46, 112.44, 116.37, 119.06, 120.38, 124.74, 129.17, 131.22, 136.04, 136.29, 148.58, 149.75, 165.21, 167.25, 169.01; Anal Calcd for $C_{22}H_{23}N_2O_7ClS$+0.1$H_2O$: C, 53.19; H, 4.71; N, 5.50; $H_2O$, 0.36. Found: C, 52.89; H, 4.52; N, 5.50; $H_2O$, 0.17.

Example 9

2-Amino-N-{2-[1-(3-ethoxy-4-methoxyphenyl)-2-methylsulfonylethyl]-1,3-dioxoisoindolin-4-yl}acetamide A mixture of 2-chloro-N-{2-[1-(3-ethoxy-4-methoxyphenyl)-2-methylsulfonylethyl]-1,3-dioxoisoindolin-4-yl}acetamide (0.30 g, 0.61 mmol) and sodium azide (90 mg, 1.38 mmol) in acetone (10 mL) was heated to reflux for 8 hours. To the solution was added triphenylphosphine (0.30 g, 1.1 mmol) and water (0.4 mL). The solution was heated to reflux for 5 more h. The solvent was removed in vacuo to give an oil. The oil was stirred in ether (10 mL) and water (10 mL) overnight to give a suspension. The suspension was filtered and washed with ether and water to give 2-amino-N-{2-[1-(3-ethoxy-4-methoxyphenyl)-2-methylsulfonylethyl]-1,3-dioxoisoindolin-4-yl}acetamide as a yellow solid (250 mg, 86% yield); mp, 111-112° C.; $^1$H NMR ($CDCl_3$) δ 1.48 (t, J=6.9 Hz, 3H, $CH_3$), 1.74 (brs, 2H, $NH_2$), 2.86 (s, 3H, $CH_3$), 3.57 (s, 2H, $CH_2$), 3.77 (dd, J=4.6, 14.5 Hz, 1H, CHH), 3.86 (s, 3H, $CH_3$), 4.11 (q, J=7.0 Hz, 2H, $CH_2$), 4.56 (dd, J=10.2, 14.2 Hz, 1H, CHH), 5.89 (dd, J=4.6, 10.2 Hz, 1H, NCH), 6.82-6.85 (m, 1H, Ar), 7.12-7.15 (m, 2H, Ar), 7.52 (d, J=7.2 Hz, 1H, Ar), 7.67 (t, J=7.5 Hz, 1H, Ar), 8.86 (d, J=8.3 Hz, 1H, Ar), 11.21 (s, 1H, NH); $^{13}$C NMR ($CDCl_3$) δ 14.68, 41.51, 48.65, 54.69, 55.88, 64.49, 111.45, 112.50, 115.81, 118.24, 120.37, 124.94, 129.38, 131.29, 135.90, 136.88, 148.55, 149.68, 167.64, 168.83, 172.41; Anal Calcd for $C_{22}H_{25}N_3O_7S$: C, 55.57; H, 5.30; N, 8.84. Found: C, 55.46; H, 5.33; N, 8.35.

Example 10

2-N,N-Dimethylamino-N-{2-[1-(3-ethoxy-4-methoxyphenyl)-2-methylsulfonylethyl]-1,3-dioxoisoindolin-4-yl}acetamide HCl A mixture of 2-azido-N-{2-[1-(3-ethoxy-4-methoxyphenyl)-2-methylsulfonylethyl]-1,3-dioxoisoindolin-4-yl}acetamide (0.80 g, 1.59 mmol), Pd/C (0.2 g) and formaldehyde (10 mL, 37% wt in water) in ethanol (90 mL) was shaken under hydrogen (50-60 psi) in a Parr flask for 3 days. The suspension was filtered through a pad of Celite and washed with acetone (50 mL). The solvent was removed in vacuo to give an oil. The oil was stirred in methanol (10 mL). The suspension was filtered and washed with methanol to give a white solid. To the solid in ethyl acetate (20 mL) was added hydrogen chloride in ether (1.5 mL, 1N) to give a suspension. The suspension was filtered and washed with ether to give 2-N,N-dimethylamino-N-{2-[1-(3-ethoxy-4-methoxyphenyl)-2-methylsulfonylethyl]-1,3-dioxoisoindolin-4-yl}acetamide hydrogen chloride as a yellow solid (300 mg, 35% yield); mp, 105-107° C.; $^1$H NMR (DMSO-d6) δ 1.33 (t, J=6.9 Hz, 3H, $CH_3$), 2.87 (s, 6H, 2$CH_3$), 3.03 (s, 3H, $CH_3$), 3.74 (s, 3H, $CH_3$), 4.02 (q, J=7.0 Hz, 2H, $CH_2$), 4.16 (dd, J=4.2, 14.3 Hz, 1H, CHH) 4.25 (brs, 2H, $CH_2$), 4.34 (dd, J=10.8, 14.4 Hz, 1H, CHH), 5.79 (dd, J=4.2, 10.4 Hz, 1H, NCH), 6.92-6.99 (m, 2H, Ar), 7.08 (s, 1H, Ar), 7.69 (d, J=7.3 Hz, 1H, Ar), 7.88 (t, J=7.7 Hz, 1H, Ar), 8.21-8.27 (m, 1H, Ar), 10.29 (s, 1H, HCl), 10.64 (s, 1H, NH); $^{13}$C NMR (DMSO-d6) δ 14.65, 41.04, 43.36, 47.23, 52.86, 55.51, 58.09, 63.86, 111.79, 112.39, 119.22, 119.68, 127.78, 127.99, 129.42, 131.76, 134.25, 134.34, 135.95, 147.87, 148.92, 164.60, 166.79; Anal Calcd for $C_{24}H_{29}N_3O_7S$+1.1HCl+0.3$H_2O$: C, 52.50; H, 5.64; N, 7.65; Cl, 7.10. Found: C, 52.16; H, 5.75; N, 7.37; Cl, 7.20.

Example 11

N-{2-[1-(3-ethoxy-4-methoxyphenyl)-2-methylsulfonylethyl]-1,3-dioxoisoindolin-4-yl}-2,2,2-trifluoroacetamide A mixture of 2-[1-(3-ethoxy-4-methoxyphenyl)-2-methylsulfonylethyl]-4-aminoisoindoline-1,3-dione (1.0 g, 2.4 mmol) and trifluoroacetic anhydride (3 mL) was heated to reflux for 30 minutes. The solvent was removed in vacuo to give an oil. The oil was stirred in ether (5 mL) and hexane (40 mL) for 3 days. The suspension was filtered and washed with ether to give a yellow solid. The solid was then recrystallized from ethanol (10 mL) to give N-{2-[1-(3-ethoxy-4-methoxyphenyl)-2-methylsulfonylethyl]-1,3-dioxoisoindolin-4-yl}-2,2,2-trifluoroacetamide as a yellow solid (280 mg, 23% yield): mp, 130-132° C.; $^1$H NMR ($CDCl_3$) δ 1.48 (t, J=6.9 Hz, 3H, $CH_3$), 2.92 (s, 3H, $CH_3$), 3.70 (dd, J=4.2, 14.3 Hz, 1H, CHH), 3.87 (s, 3H, $CH_3$), 4.13 (q, J=6.9 Hz, 2H, $CH_2$), 4.59 (dd, J=10.9, 14.3 Hz, 1H, CHH), 5.90 (dd, J=4.2, 10.9 Hz, 1H, NCH), 6.86 (d, J=8.3 Hz, 1H, Ar), 7.11-7.15 (m, 2H, Ar), 7.66 (d, J=7.2 Hz, 1H, Ar), 7.77 (t, J=7.5 Hz, 1H, Ar), 8.70 (d, J=8.4 Hz, 1H, Ar), 10.39 (s, 1H, NH); $^{13}$C NMR ($CDCl_3$) δ 14.59, 41.57, 48.68, 54.10, 55.89, 64.50, 111.48, 112.38, 115.16 (q, $J_{CF}$=286 Hz), 117.19, 120.28, 120.31, 125.01, 128.85, 131.26, 134.63, 136.35, 148.63, 149.85, 155.36 (q, $J^2_{CF}$=38 Hz), 166.78, 169.14; Anal Calcd for $C_{22}H_{21}N_2O_7F_3S$: C, 51.36; H, 4.11; N, 5.44. Found: C, 51.20; H, 4.07; N, 5.20.

Example 12

N-{2-[1-(3-Ethoxy-4-methoxyphenyl)-2-methylsulfonylethyl]-1,3-dioxoisoindolin-4-yl}methoxycarboxamide A mixture of 2-[1-(3-ethoxy-4-methoxyphenyl)-2-methylsulfonylethyl]-4-aminoisoindoline-1,3-dione (0.70 g, 1.7 mmol) and methyl chloroformate (25 mL) was heated to reflux for 30 minutes. To the mixture was added ethanol (5 mL). The suspension was filtered and washed with ethanol to give N-{2-[1-(3-Ethoxy-4-methoxyphenyl)-2-methylsulfonylethyl]-1,3-dioxoisoindolin-4-yl}methoxycarboxamide as a white solid (0.48 g, 60% yield): mp, 178-180° C.; $^1$H NMR ($CDCl_3$); δ 1.48 (t, J=7.1 Hz, 3H, $CH_3$), 2.86 (s, 3H, $CH_3$), 3.76 (dd, J=4.4, 14.4 Hz, 1H, CHH), 3.84 (s, 3H, $CH_3$), 3.86 (s, 3H, $CH_3$), 4.12 (q, J=6.9 Hz, 2H, $CH_2$), 4.55 (dd, J=10.3, 14.4 Hz, 1H, CHH), 5.87 (dd, J=4.5, 10.3 Hz, 1H, NCH), 6.83-6.87 (m, 1H, Ar), 7.09-7.13 (m, 2H, Ar), 7.45 (d, J=7.0 Hz, 1H, Ar), 7.66 (t, J=8.3 Hz, 1H, Ar), 8.50 (d, J=8.5 Hz, 1H, Ar), 8.93 (brs, 1H, NH); $^{13}$C NMR ($CDCl_3$) δ 14.61, 41.52, 48.62, 52.70, 54.58, 55.88, 64.46, 111.40, 112.39, 114.78, 117.42, 120.29, 123.43, 129.27, 131.22, 135.97, 137.74, 148.59, 149.69, 153.42, 167.35, 169.23; Anal Calcd for $C_{22}H_{24}N_2O_8S$: C, 55.45; H, 5.08; N, 5.88. Found: C, 55.32; H, 5.00; N, 5.73.

Example 13

4-[1-Aza-2-(dimethylamino)vinyl]-2-[1-(3-ethoxy-4-methoxyphenyl)-2-methylsulfonylethyl]isoindoline-1,3-dione A mixture of 2-[1-(3-ethoxy-4-methoxyphenyl)-2-methylsulfonylethyl]-4-aminoisoindoline-1,3-dione (1.5 g, 3.6 mmol) and dimethylformamide dimethyl acetal (4 mL) was heated to reflux for 30 minutes. The solvent was removed in vacuo to give an oil. The oil was stirred in ether (20 mL). The suspension was filtered and washed with ether to give 4-[1-aza-2-(dimethylamino)vinyl]-2-[1-(3-ethoxy-4-methoxyphenyl)-2-methylsulfonylethyl]isoindoline-1,3-dione as a yellow solid (1.1 g, 65% yield): mp, 161-163° C.; $^1$H NMR ($CDCl_3$) δ 1.46 (t, J=6.9 Hz, 3H, $CH_3$), 2.79 (s, 3H, $CH_3$), 3.11-3.12 (2s, 6H, 2$CH_3$), 3.82 (dd, J=5.2, 14.5 Hz, 1H, CHH), 3.85 (s, 3H, $CH_3$), 4.10 (q, J=6.9 Hz, 2H, $CH_2$), 4.49 (dd, J=9.5, 14.6 Hz, 1H, CHH), 5.86 (dd, J=5.2, 9.4 Hz, 1H, NCH), 6.80-6.83 (m, 1H, Ar), 7.11-7.19 (m, 3H, Ar), 7.39-7.52 (m, 2H, Ar), 7.72 (s, 1H, CH); $^{13}$C NMR ($CDCl_3$) δ 14.68, 34.49, 40.41, 41.49, 48.78, 55.45, 55.93, 64.47, 111.41, 111.65, 116.99, 118.98, 120.54, 129.99, 130.58, 133.16, 134.49, 148.48, 149.50, 152.06, 156.64, 168.06, 168.19; Anal Calcd for $C_{23}H_{27}N_{13}O_6S$: C, 58.34; H, 5.75; N, 8.87. Found: C, 58.17; H, 5.71; N, 8.69.

Example 14

4-[1-Aza-2-(dimethylamino)prop-1-enyl]-2-[1-(3-ethoxy-4-methoxyphenyl)-2-methylsulfonylethyl]isoindoline-1,3-dione A mixture of 2-[1-(3-ethoxy-4-methoxyphenyl)-2-methylsulfonylethyl]-4-aminoisoindoline-1,3-dione (1.5 g, 3.6 mmol) and dimethylacetamide dimethyl acetal (4 mL) was heated to reflux for 30 minutes. The solvent was removed in vacuo to give an oil. The oil was stirred in ether/hexane/ethyl acetate (10/10/1 mL) overnight. The suspension was filtered to give an orange solid. The solid was separated by chromatography (Silica gel, 1% methanol in methylene chloride) to give 4-[1-aza-2-(dimethylamino)prop-1-enyl]-2-[1-(3-ethoxy-4-methoxyphenyl)-2-methylsulfonylethyl]isoindoline-1,3-dione as a yellow solid (140 mg, 8% yield): mp, 111-113° C.; $^1$H NMR ($CDCl_3$) δ 1.46 (t, J=6.9 Hz, 3H, $CH_3$), 1.87 (s, 3H, $CH_3$), 2.79 (s, 3H, $CH_3$), 3.12 (s, 3H, $CH_3$), 3.79 (dd, J=4.9, 14.6 Hz, 1H, CHH), 3.87 (s, 3H, $CH_3$), 4.10 (q, J=6.9 Hz, 2H, $CH_2$), 4.50 (dd, J=9.8, 14.6 Hz, 1H, CHH), 5.84 (dd, J=4.9, 9.7 Hz, 1H, NCH), 6.80-6.83 (m, 2H, Ar), 7.20 (d, J=8.3 Hz, 1H, Ar), 7.10-7.12 (m, 2H, Ar), 7.36 (d, J=7.1 Hz, 1H, Ar), 7.49 (t, J=7.6 Hz, 1H, Ar); $^{13}$C NMR ($CDCl_3$) δ 14.61, 15.59, 38.06, 41.36, 48.51, 55.25, 55.86, 64.41, 111.36, 112.56, 116.20, 118.78, 120.36, 129.98. 131.24, 132.67, 134.36, 148.41, 149.42, 150.80, 158.65, 167.78, 168.27; Anal Calcd for $C_{24}H_{29}N_3O_6S$: C, 59.12; H, 6.00; N, 8.62, Found: C, 58.84; H, 6.01; N, 8.36.

Example 15

2-[1-(3-Ethoxy-4-methoxyphenyl)-2-methylsulfonylethyl]-4-(5-methyl-1,3,4-oxadiazol-2-yl)isoindoline-1,3-dione A mixture of 2-[1-(3-ethoxy-4-methoxyphenyl)-2-methylsulfonylethyl]-1,3-dioxoisoindoline-4-carboxylic acid (1.5 g, 3.4 mmol) and carbonyldiimidazole (600 mg, 3.7 mmol) in tetrahydrofuran (10 mL) was stirred at room temperature for 2 hours. To the mixture was added acetic hydrazide (411 mg, 5.54 mmol) and kept for 16 h. The mixture was extracted with ethyl acetate (125 mL) and water (40 mL). The organic layer was washed with sodium hydrogen carbonate (50 mL, sat), and dried over magnesium sulfate. The solvent was removed in vacuo to give a yellow solid (0.8 g). The solid and phosphoryl trichloride (2 mL) in acetonitrile (20 mL) was heated to reflux for 15 hours. To the mixture was added water (10 mL) then sodium hydrogen carbonate (60 mL, sat) until pH ~8. The aqueous layer was extracted with ethyl acetate (150 mL). The organic layer was washed with sodium hydrogen carbonate (50 mL, sat), brine (50 mL) and dried over magnesium sulfate. The solvent was removed in vacuo to give a yellow solid. The solid was separated by chromatography (silica gel, 50:50 ethyl acetate/methylene chloride) to give 2-[1-(3-ethoxy-4-methoxyphenyl)-2-methylsulfonylethyl]-4-(5-methyl-1,3,4-oxadiazol-2-yl)isoindoline-1,3-dione as a yellow solid (450 mg, 28% yield): mp, 99-101° C.; $^1$H NMR ($CDCl_3$) δ 1.48 (t, J=6.9 Hz, 3H, $CH_3$), 2.71 (s, 3H, $CH_3$), 2.88 (s, 3H, $CH_3$), 3.78 (dd, J=4.6, 14.5 Hz, 1H, CHH), 3.86 (s, 3H, $CH_3$), 4.11 (q, J=6.9 Hz, 2H, $CH_3$), 4.57 (dd, J=10.3, 14.3 Hz, 1H, CHH), 5.94 (dd, J=4.6, 10.2 Hz, 1H, NCH), 6.83-6.86 (m, 1H, Ar), 7.12-7.16 (m, 2H, Ar), 7.86 (t, J=7.8 Hz, 1H, Ar), 8.04 (dd, J=0.8, 7.2 Hz, 1H, Ar), 8.28 (dd, J=1.0, 7.9 Hz, 1H, Ar); $^{13}$C NMR ($CDCl_3$) δ 11.14, 14.60, 41.49, 48.95, 54.51, 55.8, 64.48, 111.43, 112.49, 120.49, 121.49, 125.95, 128.43, 129.09, 133.11, 134.36, 135.26, 148.58, 149.74, 161.94, 164.99, 165.07, 166.69; Anal Calcd for $C_{23}H_{23}N_3O_7S$+0.6 ethyl acetate: C, 56.67; H, 5.20; N, 7.80. Found: C, 56.29; H, 4.82; N, 7.97.

Example 16

2-[1-(3-Ethoxy-4-methoxyphenyl)-2-methylsulfonylethyl]-4-pyrrolylisoindoline-1,3-dione A mixture of 2-[1-(3-ethoxy-4-methoxyphenyl)-2-methylsulfonylethyl]-4-aminoisoindoline-1,3-dione (1.0 g, 2.4 mmol) and 2,5-dimethoxytetrahydrofuran (0.33 mL, 2.5 mmol) in acetic acid (1 mL) was heated to reflux for 2 hours. The solvent was removed in vacuo to give a yellow solid. The solid was stirred in ethanol (25 mL) for 1 hour. The suspension was filtered and washed with ethanol to give 2-[1-(3-ethoxy-4-methoxyphenyl)-2-methylsulfonylethyl]-4-pyrrolylisoindoline-1,3-dione as a brown solid (1.12 g, 100% yield): mp, 95-97° C.; $^1$H NMR ($CDCl_3$) δ 1.47 (t, J=6.9 Hz, 3H, $CH_3$), 2.87 (s, 3H, $CH_3$), 3.73 (dd, J=4.5, 14.4 Hz, 1H, CHH), 3.86 (s, 3H, $CH_3$), 4.11 (q, J=6.9 Hz, 2H, $CH_2$), 4.60 (dd, J=10.6, 14.4 Hz, 1H, CHH), 5.91 (dd, J=4.4, 10.4 Hz, 1H, NCH), 6.39-6.41 (m, 2H, Ar), 6.84 (d, J=8.0 Hz, 1H, Ar), 7.12-7.17 (m, 4H, Ar), 7.60-7.65 (m, 1H, Ar), 7.74-7.78 (m, 2H, Ar); $^{13}$C NMR ($CDCl_3$) δ 14.60, 41.44, 48.77, 54.32, 55.88, 64.48, 110.74, 111.41, 112.57, 120.52, 120.99, 122.00, 129.25, 130.09, 133.74, 135.36, 138.62, 148.52, 149.67, 165.77, 166.82; Anal Calcd for $C_{24}H_{24}N_2O_6S$: C, 61.53; H, 5.16; N, 5.98. Found: C, 61.34; H, 5.17; N, 5.83.

Example 17

4-(Aminomethyl)-2-[1-(3-ethoxy-4-methoxyphenyl)-2-methylsulfonylethyl]-isoindoline-1,3-dione hydrochloride A mixture of 4-cyano-2-[1-(3-ethoxy-4-methoxyphenyl)-2-methylsulfonylethyl]isoindoline-1,3-dione (0.5 g, 1.17 mmol) and 10% Pd/C (0.15 g) in 4 N hydrochloric acid (1 mL) and methanol (40 mL) was hydrogenated in Parr Shaker apparatus under 50 psi of hydrogen overnight. To the resulting slurry was added water (2 mL) to dissolve the product. The reaction mixture was then filtered through Celite and the filtrate was concentrated in vacuo. The residue was slurried in ethyl acetate (10 mL) to afford 0.52 g of the crude product. The product was reslurried in hot ethanol (15 mL) to afford 4-(aminomethyl)-2-[1-(3-ethoxy-4-methoxyphenyl)-2-methylsulfonylethyl]isoindoline-1,3-dione hydrochloride (0.44 g, 80% yield): mp 237-239° C.; $^1$H NMR (DMSO-$d_6$) δ 8.79 (s, 3H, Ar), 8.04-7.89 (m, 3H, Ar), 7.11-6.91 (m, 3H, Ar), 5.83-5.77 (dd, J=4.2, 10.1 Hz, 1H, NCH), 4.49-4.47 (m, 2H, $CH_2$), 4.41-4.31 (m, 1H, CHH), 4.21-4.13 (m, 1H, CHH), 4.04 (q, J=6.8 Hz, 2H, $CH_2$), 3.73 (s, 3H, $CH_3$), 3.64 (s, 3H, $CH_3$), 1.32 (t, J=6.8 Hz, 3H, $CH_3$); $^{13}$C NMR (DMSO-d6) δ 167.48, 166.93, 148.95, 147.87, 135.39, 134.71, 132.82, 131.32, 129.50, 128.30, 123.34, 119.89, 112.55, 111.79, 63.87, 55.52, 53.07, 47.46, 41.08, 36.84, 14.66; Anal. Calcd for $C_{21}H_{25}N_2O_6SCl$: C, 53.79; H, 5.37; N, 5.97; S, 6.84; Cl, 7.56. Found: C, 53.49, H, 5.47; N, 5.75; S, 6.61; Cl, 7.51.

Example 18

2-[1-(3-Ethoxy-4-methoxyphenyl)-2-methylsulfonylethyl]-4-(pyrrolylmethyl)isoindoline-1,3-dione A mixture of 4-(aminomethyl)-2-[1-(3-ethoxy-4-methoxyphenyl)-2-methylsulfonylethyl]isoindoline-1,3-dione (0.34 g, 0.79 mmol) and 2,5-dimethoxytetrahydrofuran (0.10 g, 0.79 mmol) in acetic acid (5 mL) was heated to reflux for 1 hour. The reaction mixture was then concentrated in vacuo and the residue was stirred with ethyl acetate (50 mL) and saturated sodium bicarbonate (25 mL). The organic layer was washed with water (25 mL), brine (25 mL), dried and concentrated. The residue was purified by flash chromatography (methylene chloride:ethyl acetate, 95:5) to afford 2-[1-(3-ethoxy-4-methoxyphenyl)-2-methylsulfonylethyl]-4-(pyrrolylmethyl)isoindoline-1,3-dione (0.23 g, 60% yield): mp 80-82° C.; $^1$H NMR ($CDCl_3$) δ 7.71 (d, J=7.3 Hz, 1H, Ar), 7.57 (t, J=7.7 Hz, 1H, Ar), 7.26 (m, 2H, Ar), 7.15 (d, J=7.0 Hz, 2H, Ar), 6.96 (d, J=7.8 Hz, 1H, Ar), 6.71 (d, J=1.7 Hz, 1H, Ar), 6.22 (d, J=1.8 Hz, 1H, Ar), 5.94-5.88 (dd, J=4.4 and 10.3 Hz, 1H, NCH), 5.57 (s, 2H, $CH_2$), 4.63-4.53 (dd, J=10.7, 14.4 Hz, 1H, CHH), 4.13 (q, J=7.0 Hz, 2H, $CH_2$), 3.85 (s, 3H, $CH_3$), 3.80-3.72 (dd, J=4.4, 14.4 Hz, 1H, CHH), 2.86 (s, 3H, $CH_3$), 1.47 (t, J=6.9 Hz, 3H, $CH_3$); $^{13}$C NMR ($CDCl_3$) δ 168.08, 167.69, 149.72, 148.63, 138.71, 134.74, 132.65, 131.86, 129.44, 126.92, 122.69, 121.46, 120.47, 112.49, 111.44, 109.15, 64.51, 55.95, 54.65, 48.73, 48.57, 41.58, 14.69; Anal. Calcd for $C_{25}H_{26}N_2O_6S$: C, 62.23; H, 5.43: N, 5.81; S, 6.64. Found: C, 62.25; H, 5.56; N, 5.63; S, 6.83.

Example 19

3-(tert-Butyloxycarbonylamino)-3-(3-ethoxy-4-methoxyphenyl)propionic Acid

A mixture of 3-amino-3-(ethoxy-4-methoxyphenyl)propionic acid (20 g, 83.5 mmol), 2N sodium hydroxide (50 mL), t-butanol (42 mL) and water (80 mL) was stirred at 10° C. Di-(tert-butyl)dicarbonate (20 g, 91.6 mmol) was added in portions over 25 minutes. The resulting mixture was stirred at room temperature for 2 hours (maintained at pH 10 by the addition of 2N sodium hydroxide). The mixture was washed with ether and the aqueous solution was acidified to pH 2 with 6N hydrochloric acid. The slurry was filtered and washed with water to yield 3-(tert-butyloxycarbonylamino)-3-(3-ethoxy-4-methoxyphenyl)propionic acid as a white solid (28.3 g, 100%); $^1$H NMR ($CDCl_3$/DMSO-$d_6$) δ 6.86-6.78 (m, 3H), 5.83 (d, J=8.3 Hz, 1H), 4.98 (b, 1H), 4.09 (q, J=7.0 Hz, 2H), 3.83 (s, 3H), 2.77 (m, 2H), 1.46-1.41 (m, 12H); $^{13}$C NMR ($CDCl_3$/DMSO-$d_6$) δ 173.22, 155.02, 148.15, 147.89, 134.31, 117.97, 111.22, 111.07, 79.12, 64.01, 55.09, 50.76, 40.78, 28.11, 14.55.

Example 20

3-(tert-Butyloxycarbonylamino)-3-(3-ethoxy-4-methoxyphenyl)-N-methoxy-N-methylpropanamide A mixture of carbonyldiimidazole (0.96 g, 5.9 mmol), 3-(tert-butoxycarbonylamino)-3-(3-ethoxy-4-methoxyphenyl)propionic acid (2.0 g, 5.9 mmol) and methylene chloride (25 mL) was stirred at room temperature for 1 hr and then cooled to 5° C. A solution of N,O-dimethylhydroxyamine hydrochloride (0.86 g, 8.85 mmol) and 1-methylpiperidine (0.87 g, 8.85 mmol) in methylene chloride (10 mL) was added slowly. The mixture was stirred at room temperature for 1 hr and then quenched with water (20 mL). The organic layer was separated and then was washed with 1N citric acid, water, and brine. The organic layer was dried and concentrated in vacuo to give an oil. This oil was purified by chromatography (silica gel, methylene chloride:ethyl acetate 8:2) to afford 3-(tert-butyloxycarbonylamino)-3-(3-ethoxy-4-methoxyphenyl)-N-methoxy-N-methylpropanamide as a white solid (1.76 g, 78%); $^1$H NMR ($CDCl_3$) δ 6.86-6.78 (m, 3H), 6.07 (b, 1H), 5.01 (m, 1H), 4.10 (q, J=6.9 Hz, 2H), 3.84 (s, 3H), 3.50 (s, 3H), 3.10 (s, 3H), 3.02 (m, 2H), 2.84-2.75 (dd, J=5.3 and 15.2 Hz, 1H), 1.45 (t, J=7.1 Hz, 3H), 1.41 (s, 9H); $^{13}$C NMR ($CDCl_3$) δ 171.81, 155.18, 148.39, 148.19, 134.82, 118.12, 111.41, 111.18, 79.27, 64.26, 61.19, 55.90, 51.25, 37.80, 31.87, 28.33, 14.73.

Example 21

(tert-Butoxy)-N-[1-(3-ethoxy-4-methoxyphenyl)-3-oxobutyl]carboxamide

Methyl magnesium bromide (3M, 19.6 mL, 58.8 mmol) was slowly added to a stirred solution of 3-(tert-butyloxycarbonylamino)-3-(3-ethoxy-4-methoxyphenyl)-N-methoxy-N-methylpropanamide (9.0 g, 23.5 mmol) in tetrahydrofuran (80 mL) at 5-12° C. After the addition was complete, the mixture was stirred at room temperature for 1.5 hours. The mixture was then cooled to 5° C., quenched with sat. ammonium chloride (40 mL) and extracted with ethyl acetate. The combined ethyl acetate extracts were washed with 1N citric acid, sat. sodium bicarbonate, $H_2O$, brine, dried, and then concentrated to yield an oil. The oil was purified by chromatography (silica gel, methylene chloride:ethyl acetate 9:1) to give (tert-bytoxy)-N-[1-(3-ethoxy-4-methoxyphenyl)-3-oxobutyl]carboxamide as a white solid (6.4 g, 81%); mp 118-120° C.; $^1$H NMR ($CDCl_3$) δ 6.83-6.80 (m, 3H), 5.30 (b, 1H), 5.01-4.99 (m, 1H), 4.10 (q, J=6.9 Hz, 2H), 3.84 (s, 3H), 2.99-2.85 (m, 2H), 2.09 (s, 3H), 1.48-1.41 (m, 12H); $^{13}$C NMR ($CDCl_3$) δ 206.98, 155.07, 148.61, 148.32, 118.15, 117.47, 111.36, 79.65, 64.34, 55.93, 50.99, 49.42, 30.58, 28.31, 14.25; Anal. Calcd. For $C_{18}H_{27}NO_5$: C, 64.07; H, 8.07; N, 4.15. Found: C, 63.90; H, 8.13; N, 3.97.

Example 22

(tert-Butoxy)-N-[1-(3-ethoxy-4-methoxyphenyl)-3-hydroxybutyl]carboxamide

A mixture of (tert-butoxy)-N-[1-(3-ethoxy-4methoxyphenyl)-3-oxobutyl]carboxamide (2.0 g, 5.92 mmol) and sodium borohydride (0.4 g, 12.0 mmol) in methanol (40 mL) and tetrahydrofuran (10 mL) was stirred at −10 to −20° C. for 4 hours. The mixture was quenched with water (10 mL) and then concentrated in vacuo to afford an oil. The oil was dissolved in ethyl acetate and washed with water, brine, dried, and concentrated in vacuo to afford an oil. The oil was purified by chromatography (silica gel, methylene chloride:ethyl acetate 8:2) to give the two diasteromers of (tert-butoxy-N-[1-(3-ethoxy-4-methoxyphenyl)-3-hydroxybutyl)carboxamide:

A; 0.98 g (49%); $^1$H NMR ($CDCl_3$) δ 6.83-6.81 (m, 3H), 4.99-4.96 (m, 1H), 4.85-4.83 (m, 1H), 4.11 (q, J=6.9 Hz, 2H), 3.85 (s, 3H), 3.78 (m, 1H), 1.80-1.75 (m, 2H), 1.49-1.45 (m, 12H), 1.24 (d, J=6.1 Hz, 3H).

B; 0.84 g (42%); $^1$H NMR ($CDCl_3$) δ 6.82 (m, 3H), 5.06-5.03 (m, 1H), 4.68 (m, 1H), 4.11 (q, J=7.0 Hz, 2H), 3.85 (s, 3H), 3.82-3.70 (m, 1H), 1.94-1.82 (m, 2H), 1.48-1.40 (m, 12H), 1.21 (d, J=6.2 Hz, 3H).

Example 23

4-Amino-4-(3-ethoxy-4-methoxyphenyl)butan-2-ol Hydrochloride

A mixture of (tert-butoxy)-N-[1-(3-ethoxy-4-methoxyphenyl)-3-hydroxybutyl]carboxamide (0.98 g, 2.89 mmol) and 4Nhydrochloric acid/dioxane (3 mL) in methylene chloride (10 mL) was stirred at room temperature for 16 hours. The resulting slurry was filtered and washed with ethyl acetate to give 4-amino-4-(3-ethoxy-4-methoxyphenyl)butan-2-ol hydrochloride as a white solid (0.68 g, 85%); $^1$H NMR ($D_2O$) δ 7.12 (m, 3H), 4.47 (t, J=7.0 Hz, 1H), 4.20 (q, J=7.4 Hz, 2H), 3.90 (s, 3H), 3.83-3.76 (m, 1H), 2.21-2.15 (m, 2H), 1.43 (t, J=6.9 Hz, 3H), 1.24 (d, J=6.1 Hz, 3H); $^{13}$C NMR ($D_2O$) δ 151.75, 150.48, 131.92, 123.09, 115.05, 114.54, 67.86, 66.98, 58.53, 55.35, 44.41, 24.49, 16.68.

Example 24

N-{2-[1-(3-ethoxy-4-methoxyphenyl)-3-hydroxybutyl]-1,3-dioxoisoindolin-4-yl}acetamide A mixture of 4-amino-4-(3-ethoxy-4-methoxyphenyl)butan-2-ol hydrochloride (0.5 g, 1.81 mmol), 3-acetamidophthalic anhydride (0.37 g, 1.81 mmol) and triethylamine (0.18 g, 1.81 mmol) in dimethylformamide (10 mL) was heated at 80-90° C. for 7 hours. The mixture was concentrated in vacuo to an oil. The oil was dissolved in ethyl acetate, washed with water, brine, dried, filtered and concentrated to an oil. This oil was purified by chromatography (silica gel, methylene chloride/ethyl acetate 8:2) to give N-{2-[1-(3-ethoxy-4-methoxyphenyl)-3-hydroxybutyl]-1,3-dioxoisoindolin-4-yl}acetamide as a white solid (0.5 g, 65%); mp 132-134° C.; $^1$H NMR ($CDCl_3$) δ 9.54 (s, 1H), 8.73 (d, J=8.4 Hz, 1H), 7.62 (t, J=7.4 Hz, 1H), 7.46 d, J=7.3 Hz, 1H), 7.12-7.08 (m, 2H), 6.83 (d, J=8.0 Hz, 1H), 5.46 (t, J=7.8 Hz, 1H), 4.12 (q, J=7.1 Hz, 2H), 3.84 (s, 3H), 3.80 (m, 1H), 2.59-2.42 (m, 2H), 2.25 (s 3H), 1.65 (s, 1 H), 1.45 (t, J=7.0 Hz, 3H), 1.27 (d, J=6.3 Hz, 3H); $^{13}$C NMR ($CDCl_3$) δ 170.36, 169.20, 167.96, 149.04, 148.26, 137.29, 135.70, 131.50, 131.35, 124.60, 120.61, 117.85, 113.10, 111.25, 66.00, 64.39, 55.89, 52.43, 40.19, 24.92, 24.33, 14.73; Anal. Calcd. For $C_{23}H_{26}N_2O_6$: C, 64.78; H, 6.15; N, 6.57. Found: C, 64.86; H, 6.10; N, 6.46.

Example 25

N-{2-[1-(3-Ethoxy-4-methoxyphenyl)-3-oxobutyl]-1,3-dioxoisoindolin-4-yl}acetamide A mixture of N-{2-[1-(3-ethoxy-4-methoxyphenyl)-3-hydroxybutyl]-1,3-dioxoisoindolin-4-yl}acetamide (1.2 g, 2.81 mmol), pyridium chlorochromate (1.21 g, 5.63 mmol) and celite (0.6 g) in methylene chloride (35 mL) was stirred at room temperature for 4 hours. The mixture was filtered through celite and the celite washed with methylene chloride. The filtrate was washed with water, brine, dried, and concentrated. The residue was purified by chromatography (silica gel, methylene chloride:ethyl acetate 9:1) to yield N-{2-[1-(3-ethoxy-4-methoxyphenyl)-3-oxobutyl]-1,3-dioxoisoindolin-4-yl}acetamide as a white solid (0.9 g, 76%); mp 128-129° C.; $^1$H NMR ($CDCl_3$) δ 9.52 (s, 1H), 8.71 (d, J=8.4 Hz, 1H), 7.62 (t, J=7.5 Hz, 1H), 7.46 (d, J=7.2 Hz, 1H), 7.06-7.03 (m, 2H), 6.82 (d, J=8.9 Hz, 1H), 5.73-5.07 (dd, J=5.2 and 10.0 Hz, 1H), 4.11 (q, J=7.0 Hz, 2H), 4.04-3.93 (dd, J=10.0 and 18.0 Hz, 1H), 3.83 (s, 3H), 3.28-3.19 (dd, J=5.2 and 18.0 Hz, 1H), 2.26 (s, 3H), 2.18 (s, 3H), 1.46 (t, J=7.1 Hz, 3H); $^{13}$C NMR ($CDCl_3$) δ 205.18, 170.62, 169.17, 167.10, 149.21, 148.40, 137.38, 135.81, 131.34, 131.24, 124.69, 120.02, 117.91, 115.30, 112.57, 111.37, 64.44, 55.93, 49.96, 44.82, 30.14, 24.93, 14.73; Anal. Calcd. For $C_{23}H_{24}N_2O_6$: C, 65.08; H, 5.70; N, 6.60. Found: C, 65.11; H, 5.64; N, 6.50.

Example 26

N-{2-[1R-(3-ethoxy-4-methoxyphenyl)-3-hydroxybutyl]-1,3-dioxoisoindolin-4-yl}acetamide A mixture of R-4-amino-4-(3-ethoxy-4-methoxyphenyl) butan-2-ol (1.5 g, 5.44 mmol), 3-acetamidophthalic anhydride (1.11 g, 5.44 mmol) and triethylamine (0.55 g, 5.44 mmol) was heated at 80-90° C. for 7 hours. The mixture was concentrated in vacuo to an oil. The oil was dissolved in ethyl acetate and washed with water, brine, dried and concentrated. The residue was purified by chromatography (silica gel, methylene chloride:ethyl acetate 8:2) to give N-{2-[1R-(3-ethoxy-4-methoxyphenyl)-3-hydroxybutyl]-1,3-dioxoisoindolin-4-yl}acetamide as a white solid (1.87 g, 80%); $^1$H NMR ($CDCl_3$) δ 9.61 (s, 1H), 8.75 (d, J=8.4 Hz, 1H), 7.63 (t, J=7.6 Hz, 1H), 7.47 (d, J=7.2 Hz, 1H), 7.06 (m, 2H), 6.83-6.80 (m, 1H), 5.58-5.51 (dd, J=4.2 and 11.7 Hz, 1H), 4.11 (q, J=7.0 Hz, 2H), 3.84 (s, 3H), 3.80-3.73 (m, 1H), 2.92-2.80 (m, 1H), 2.25 (s, 3H), 2.12-2.01 (m, 1H), 1.45 (t, J=7.0 Hz, 3H), 1.29 (d, J=6.1 Hz, 3H); $^{13}$C NMR ($CDCl_3$) δ 170.39, 169.21, 167.96, 149.01, 148.17, 137.36, 135.86, 131.61, 131.19, 124.75, 120.35, 117.95, 115.30, 112.90, 111.13, 64.88, 64.39, 55.88, 51.32, 39.92, 24.93, 23.77, 14.74.

Example 27

N-{2-[1R-(3-ethoxy-4-methoxyphenyl)-3-oxobutyl]-1,3-dioxoisoindolin-4-yl}acetamide A mixture of N-{2-[1R-(3-ethoxy-4-methoxyphenyl)-3-hydroxybutyl]-1,3-dioxoisoindolin-4-yl}acetamide (1.8 g, 4.2 mmol), pyridinium chlorochromate (1.44 g, 6.62 mmol) and Celite (0.7 g) in methylene chloride (40 mL) was stirred at room temperature for 4 hours. The mixture was filtered through celite and the filtrate was washed with water, brine, dried and concentrated. The crude product was purified by chromatography (silica gel, methylene chloride:ethyl acetate 9:1) to yield N-{2-[1R-(3-ethoxy-4-methoxyphenyl)-3-oxobutyl]-1,3-dioxoisoindolin-4-yl}acetamide as a white solid; mp 81-83° C.; $^1$H NMR ($CDCl_3$) δ 9.52 (s, 1H), 8.71 (d, J=8.4 Hz, 1H), 7.62 (t, 7.6 Hz, 1H), 7.45 (d, J=7.2 Hz, 1H), 7.06-7.03 (m, 2H), 6.83 (d, J=8.8 Hz, 1H), 5.73-5.67 (dd, J=5.2 and 9.9 Hz, 1H), 4.12 (q, J=7.0 Hz, 2H), 2.26 (s, 3H), 2.18 (s, 3H), 1.46 (t, J=7.0 Hz, 3H); $^{13}$C NMR ($CDCl_3$) δ 205.17, 170.02, 169.14, 167.84, 149.14, 148.35, 137.34, 135.79, 131.29, 131.20, 124.65, 119.97, 117.88, 115.25, 112.48, 111.29, 64.39, 55.89, 49.92, 44.78, 30.13, 24.92, 14.70; Anal. Calcd. For $C_{23}H_{24}N_2O_6$: C, 65.08; H, 5.70; N, 6.60. Found: C, 65.10; H, 5.68; N, 6.45.

Example 28

N-{2-[1S-(3-Ethoxy-4-methoxyphenyl)-3-hydroxybutyl]-1,3-dioxoisoindolin-4-yl}acetamide A mixture of S-4-amino-4-(3-ethoxy-4-methoxyphenyl) butan-2-ol (1.5 g, 5.44 mmol), 3-acetamidophthalic anhydride (1.11 g, 5.44 mmol) and triethylamine (0.55 g, 5.44 mmol) in dimethylformamide (20 mL) was heated at 80-90° C. for 7 hours. The mixture was concentrated in vacuo to an oil. The oil was dissolved in ethyl acetate and washed with water, brine, dried and concentrated. The crude product was purified by chromatography (silica gel, methylene chloride: ethyl acetate 8:2) to give N-{2-[1S-(3-ethoxy-4-methoxyphenyl)-3-hydroxybutyl]-1,3-dioxoisoindolin-4-yl}acetamide as a white solid (1.81 g, 78%); $^1$H NMR ($CDCl_3$) δ 9.54-9.52 (d, 1H), 8.76-8.70 (m, 1H), 7.66-7.58 (m, 1H), 7.49-7.43 (m, 1H), 7.12-7.05 (m, 2H), 6.85-6.80 (m, 1H), 5.58-5.43 (m, 1H), 4.16-4.04 (q, 2H), 3.84 (s, 3H), 3.80-3.74 (m, 1H), 2.95-2.82 (m, 1H), 2.57-2.44 (m, 1H), 2.26 (s, 3H), 1.47 (t, 3H), 1.25 (d, 3H).

Example 29

N-{2-[1S-(3-ethoxy-4-methoxyphenyl)-3-oxobutyl] 1,3-dioxoisoindolin-4-yl}acetamide A mixture of N-{2-[1S-(3-ethoxy-4-methoxyphenyl)-3-hydroxybutyl]-1,3-dioxoisoindolin-4-yl}acetamide (1.79 g, 4.2 mmol), pyridinium chlorochromate (1.43 g, 6.63 mmol) and celite (0.7 g) in methylene chloride (50 mL) was stirred at room temperature for 4 hours. The mixture was filtered through Celite and the filtrate was washed with water, brine, dried and concentrated. The crude product was purified by chromatography (silica gel, methylene chloride/ethyl acetate 9:1) to give N-{2-[1S-(3-ethoxy-4-methoxyphenyl)-3-oxobutyl]-1,3-dioxoisoindolin-4-yl}acetamide as a white solid (1.43 g, 79%); mp 80-82° C.; $^1$H NMR ($CDCl_3$) δ 9.52 (s, 1H), 8.71 (d, J=8.4 Hz, 1H), 7.62 (t, J=7.5 Hz, 1H), 7.46 (d, J=7.3 Hz, 1H), 7.06-7.03 (m, 2H), 6.83 (d, J=8.8 Hz, 1H), 5.73-5.67 (dd, J=5.2 and 9.9 Hz, 1H), 4.11 (q, J=7.0 Hz, 2H), 4.04-3.93 (dd, J=10.0 and 18.1 Hz, 1H), 3.83 (s, 3H), 3.28-3.19 (dd, J=5.3 and 18.1 Hz, 1H), 2.26 (s, 3H), 2.18 (s, 3H), 1.46 (t, J=7.1 Hz, 3H); $^{13}$C NMR ($CDCl_3$) δ 205.19, 170.04, 169.16, 167.86, 149.16, 148.36, 137.36, 135.80, 131.31, 131.22, 124.67, 119.99, 117.90, 115.27, 112.49, 111.30, 64.41, 55.90, 49.93, 44.80, 30.15, 24.94, 14.72; Anal. Calcd. For $C_{23}H_{24}N_2O_6$: C, 65.08; H, 5.70; N, 6.60. Found: C, 65.05; H, 5.77; N, 6.61.

Example 30

4-Amino-2-[1-(3-ethoxy-4-methoxyphenyl)-3-hydroxybutyl]isoindoline-1,3-dione

A mixture of 4-amino-4-(3-ethoxy-4-methoxyphenyl)butan-2-ol hydrochloride (1.0 g, 3.63 mmol), 3-amino-N-ethoxycarbonylphthalimide (0.85 g, 3.63 mmol) and triethylamine (2.37 g, 3.63 mmol) in dimethylformamide (15 mL) was heated at 80-90° C. for 16 hours. The mixture was concentrated in vacuo and the residue was stirred with methylene chloride (10 mL). The mixture was filtered and the filtrate was concentrated and purified by chromatography (silica gel, methylene chloride:ethyl acetate 8:2) to give 4-amino-2-[1-(ethoxy-4-methoxyphenyl)-3-hydroxybutyl]isoindoline-1,3-dione as a white solid (0.72 g, 52%); $^1$H NMR ($CDCl_3$) δ 7.41-7.35 (m, 1H), 7.11-7.05 (m, 3H), 6.83-6.80 (m, 2H), 5.54-5.48 (dd, J=4.1 and 11.8 Hz, 1H), 5.22 (s, 2H), 4.10 (q, 2H), 3.85 (s, 3H), 3.77 (m, 1H), 2.88-2.77 (m, 1H), 2.07-1.00 (m, 1H), 1.67 (s, 1H), 1.45 (t, 3H), 1.27 (d, 3H).

Example 31

4-Amino-2-[1-(3-ethoxy-4-methoxyphenyl)-3-oxobutyl]isoindoline-1,3-dione

A mixture of 4-amino-2-[1-(3-ethoxy-4-methoxyphenyl)-3-hydroxybutyl]isoindoline-1,3-dione (0.7 g, 1.82 mmol), pyridinium chlorochromate (0.79 g, 3.64 mmol) and Celite (0.6 g) in methylene chloride (40 mL) was stirred at room temperature for 4 hours. The mixture was filtered through celite and the filtrate was washed with water, brine, dried and concentrated. The residue was purified by chromatography (silica gel, methylene chloride:ethyl acetate 95:5) to give 4-amino-2-[1-(3-ethoxy-4-methoxyphenyl)-3-oxobutyl] isoindoline-1,3-dione as a white solid (0.49 g, 71%); $^1$H NMR ($CDCl_3$) δ 7.38-7.31 (t, J=7.3 Hz, 1H), 7.08-7.05 (m, 3H), 6.81-6.77 (m, 2H), 5.74-5.67 (dd, J=5.9 and 9.4 Hz, 1H), 5.20 (s, 2H), 4.11 (q, J=7.0 Hz, 2H), 3.98-3.87 (dd, J=9.5 and 17.8 Hz, 1H), 3.83 (s, 3H), 3.33-3.23 (dd, J=5.6 and 17.7 Hz, 1H), 2.18-(s, 3H), 1.44 (t, J=6.9 Hz, 3H).

Example 32

2-[1-(3-Ethoxy-4-methoxyphenyl)-3-oxobutyl]-4-pyrrolylisoindoline-1,3-dione

A mixture of 4-amino-2-[1-(3-ethoxy-4-methoxyphenyl)-3-oxobutyl]isoindoline-1,3-dione (0.35 g, 0.92 mmol) and 2,5-dimethoxytetrahydrofuran (0.12 g, 0.92 mmol) in glacial acetic acid (5 mL) was refluxed for 1 hr. The mixture was dissolved in ethyl acetate (50 mL) and washed with saturated sodium bicarbonate, water, brine, dried and concentrated. The residue was purified by chromatography (silica gel, methylene chloride:ethyl acetate 95:5) to 2-[1-(3-ethoxy-4-methoxyphenyl)-3-oxobutyl]-4-pyrrolylisoindoline-1,3-dione as a yellow solid (0.27 g, 69%); mp 93-95° C.; $^1$H NMR ($CDCl_3$) δ 7.77-7.55 (m, 3H), 7.14-7.08 (m, 4H), 6.80 (d, J=8.8 Hz, 1H), 6.39-6.37 (m, 2H), 5.77-5.71 (dd, J=5.5 and 9.8 Hz, 1H), 4.10 (q, J=7.0 Hz, 1H), 4.05-3.93 (dd, J=9.8 and 18.0 Hz, 1H), 3.82 (s, 3H), 3.31-3.22 (dd, J=5.4 and 18.0 Hz, 1H), 2.16 (s, 3H), 1.44 (t, J=7.0 Hz, 3H); $^{13}$C NMR ($CDCl_3$) δ 205.27, 167.27, 166.13, 149.09, 148.25, 138.39, 135.11, 133.99, 131.39, 129.92, 122.06, 121.28, 120.74, 120.29, 112.69, 111.28, 110.66, 64.38, 55.89, 50.16, 44.69, 30.13, 14.69; Anal. Calcd. For $C_{25}H_{24}N_2O_5$: C, 69.43; H, 5.59; N, 6.48. Found: C, 69.49; H, 5.65; N, 6.33.

Example 33

2-Chloro-N-{2-[1-(3-ethoxy-4-methoxyphenyl)-3-oxobutyl]-1,3-dioxoisoindol-4-yl}acetamide A mixture of 4-amino-2-[1-(3-ethoxy-4-methoxyphenyl)-3-oxobutyl]isoindoline-1,3-dione (0.9 g, 2.34 mmol) and chloroacetyl chloride (0.29 g, 2.57 mmol) in tetrahydrofuran (20 mL) was heated to reflux for 10 minutes. The mixture was concentrated in vacuo to give 2-chloro-N-{2-[1-(3-ethoxy-4-methoxyphenyl)-3-oxobutyl]-1,3-dioxoisoindolin-4-yl}acetamide (1.07 g, 100%); $^1$H NMR ($CDCl_3$) δ 10.56 (s, 1H), 8.71 (d, J=8.4 Hz, 1H), 7.66 (t, J=7.6 Hz, 1H), 7.53 (d, J=7.3 Hz, 1H), 7.09-7.05 (m, 2H), 6.82 (d, J=8.0 Hz, 1H), 5.75-5.69 (dd, J=5.3 and 9.8 Hz, 1H), 4.22 (s, 2H), 4.12 (q, J=7.1 Hz, 2H), 4.04-3.93 (m, 1H), 3.83 (s, 3H), 3.31-3.21 (dd, J=5.2 and 18.0 Hz, 1H), 2.18 (s, 3H), 1.45 (t, J=7.0 Hz, 3H).

Example 34

2-(Dimethylamino)-N-{2-[1-(3-ethoxy-4-methoxyphenyl)-3-oxobutyl]-1,3-dioxoisoindolin-4-yl}acetamide Hydrochloride A mixture of 2-chloro-N-{2-[1-(3-ethoxy-4-methoxyphenyl)-3-oxobutyl]-1,3-dioxoisoindolin-4-yl}acetamide (1.07 g, 2.34 mmol) and N,N-dimethylamine (2.0 M in methanol, 3.5 mL, 7.0 mmol) in tetrahydrofuran (15 mL) was stirred at room temperature for 16 hours. The solvent was removed in vacuo to give an oil. The oil was purified by chromatography (silica gel, methylene chloride:ethyl acetate 7:3) to give a white solid. To a solution of the solid in ethyl acetate (10 mL) was added hydrogen chloride in ether (1N, 4 mL). The slurry was filtered and washed with ether to give 2-(dimethylamino)-N-{2-[1-(3-ethoxy-4-methoxyphenyl)-3-oxobutyl]-1,3-dioxoisoindolin-4-yl}acetamide hydrochloride as a white solid (0.52 g, 44%); mp 100-102° C.; $^1$H NMR (DMSO-$d_6$) δ 10.63 (s, 1H), 10.27 (s, 1H), 8.21 (d, J=8.2 Hz, 1H), 7.84 (t, J=7.7 Hz, 1H), 7.67 (d, J=7.3 Hz, 1H), 6.98 (s, 1H), 6.89 (s, 2H), 5.63-5.57 (dd, J=6.0 and 8.8 Hz, 1H), 4.19 (b, 2H), 3.99 (q, J=6.9 Hz, 2H), 3.77-3.67 (m, 1H), 3.74 (s, 3H), 3.52-3.42 (dd, J=6.1 and 18.1 Hz, 1H), 2.84 (s, 6H), 2.12 (s, 3H), 1.30 (t, J=6.9 Hz, 3H); $^{13}$C NMR (DMSO-$d_6$) δ 205.81, 167.32, 167.14, 164.84, 148.49, 147.76, 135.85, 134.29, 131.74, 131.48, 127.70, 119.48, 119.27, 119.09, 112.19, 111.76, 63.76, 58.32, 55.48, 48.90, 44.27, 43.47, 29.87, 14.69; Anal. Calcd. For $C_{26}H_{30}N_3O_6Cl$: C, 59.58; H, 6.00; N, 8.34; Cl, 7.03. Found: C, 59.18; H, 6.03; N, 8.14; Cl, 6.68.

Example 35

4-Amino-2-[1R-(3-ethoxy-4-methoxyphenyl)-3-hydroxybutyl]isoindoline-1,3-dione

A mixture of 4R-amino-4R-(3-ethoxy-4-methoxyphenyl) butan-2-ol hydrochloride (4.0 g, 14.5 mmol), 3-amino-N-ethoxycarbonylphthalimide (3.57 g, 15.2 mmol) and triethylamine (1.47 g, 14.5 mmol) in dimethylformamide (60 mL) was heated at 80-90° C. for 16 hours. The mixture was concentrated in vacuo and the residue was dissolved in ethyl acetate, washed with water, brine, dried and concentrated. The crude product was purified by chromatography (silica gel, methylene chloride/ethyl acetate 8/2) to give 4-amino-2-[1R-(3-ethoxy-4-methoxyphenyl)-3-hydroxybutyl]isoindoline-1,3-dione (2.3 g, 41%) as a yellow solid;

Example 36

4-Amino-2-[1R-(3-ethoxy-4-methoxyphenyl)-3-oxobutyl]isoindoline-1,3-dione

A mixture of 4-amino-2-[1R-(3-ethoxy-4-methoxyphenyl)-3-hydroxybutyl]isoindoline-1,3-dione (2.2 g, 5.72 mmol), pyridinium chlorochromate (2.5 g, 11.44 mmol) and celite (2 g) in methylene chloride (110 mL) was stirred at room temperature for 4 hours. The mixture was filtered through celite and the filtrate was washed with water, brine, dried, and concentrated. The residue was purified by chromatography (silica gel, methylene chloride:ethyl acetate 95:5) to give 4-amino-2-[1R-(3-ethoxy-4-methoxyphenyl)-3-oxobutyl]isoindoline-1,3-dione (1.23 g, 56%) as a yellow solid: $^1$H NMR ($CDCl_3$) 7.38-7.32 (m, 1H), 7.08-7.05 (m, 3H), 6.81-6.78 (m, 2H), 5.74-5.68 (dd, J=5.8 and 9.3 Hz, 1H), 5.20 (b, 2H), 4.11 (q, J=6.9 Hz, 2H), 3.98-3.87 (dd, J=9.5 and 17.8 Hz, 1H), 3.82 (s, 3H), 3.33-3.23 (dd, J=5.6 and 17.8 Hz, 1H), 2.17-(s, 3H), 1.45 (t, J=6.9 Hz, 3H); $^{13}$C NMR ($CDCl_3$) δ 205.37, 169.98, 168.58, 148.89, 148.22, 145.19, 135.04, 132.48, 131.96, 120.94, 119.98, 112.62, 112.54, 112.20, 111.06, 64.31, 60.36, 55.88, 49.54, 45.08, 30.18, 14.70.

Example 37

2-[1R-(3-ethoxy-4-methoxyphenyl)-3-oxobutyl]-4-pyrrolylisoindoline-1,3-dione A mixture of 4-amino-2-[1R-(3-ethoxy-4-methoxyphenyl)-3-oxobutyl]isoindoline-1,3-dione (0.34 g, 0.89 mmol) and 2,5-dimethoxytetrahydrofuran (0.12 g, 0.93 mmol) in glacial acetic acid (5 mL) was refluxed for 1 hr. The mixture was dissolved in ethyl acetate (50 mL) and washed with saturated sodium bicarbonate, water, brine, dried and concentrated. The residue was purified by chromatography (silica gel, methylene chloride:ethyl acetate 95:5) to give 2-[1R-(3-ethoxy-4-methoxyphenyl)-3-oxobutyl]-4-pyrrolylisoindoline-1,3-dione (0.23 g, 60%) as a yellow solid; mp 90-92° C.; $^1$H NMR ($CDCl_3$) δ 7.73-7.56 (m, 3H), 7.15-7.08 (m, 4H), 6.81 (d, J=8.8 Hz, 1H), 6.39-6.38 (m, 2H), 5.77-5.71 (dd, J=5.4 and 9.8 Hz, 1H), 4.10 (q, J=6.9 Hz, 2H), 4.05-3.94 (dd, J=9.8 and 18.1 Hz, 1H), 3.82 (s, 3H), 3.31-3.22 (dd, J=5.4 and 18.1 Hz, 1H), 2.16 (s, 3H) 1.45 (t, J=6.9 Hz, 3H); $^{13}$C NMR ($CDCl_3$) δ 205.28, 167.27, 166.13, 149.08, 148.24, 138.39, 135.11, 133.99, 131.38, 129.03, 122.05, 121.28, 120.75, 120.28, 112.66, 111.26, 110.66, 64.37, 55.89, 50.15, 44.69, 30.14, 14.69; Anal. Calcd. For $C_{25}H_{24}N_2O_5$: C, 69.43; H, 5.59; N, 6.48. Found: C, 69.49; H, 5.65; N, 6.33.

Example 38

2-(Dimethylamino)-N-{2-[1R-(3-ethoxy-4-methoxyphenyl)-3-oxobutyl]-1,3-dioxoisoindolin-4-yl}acetamide Hydrochloride A mixture of 4-amino-2-[1R-(3-ethoxy-4-methoxyphenyl)-3-oxobutyl]isoindoline-1,3-dione (0.9 g, 2.34 mmol) and chloroacetyl chloride (0.29 g, 2.58 mmol) in tetrahydrofuran (20 mL) was heated to reflux for 10 minutes to give crude 2-chloro-N-{2-[1R-(3-ethoxy-4-methoxyphenyl)-3-oxobutyl]-1,3-dioxoisoindolin-4-yl}acetamide, which was stirred with N,N-dimethylamine (2.0 M in methanol, 3.5 mL) in tetrahydrofuran (15 mL) at room temperature for 16 hours. The mixture was concentrated in vacuo to an oil. The oil was purified by chromatography (silica gel, methylene chloride: ethyl acetate 75:25) to give a white solid. To the solid in ethyl acetate (10 mL) was added 1N hydrochloric acid in ether (4 mL). The slurry was filtered and washed with ether to give 2-(dimethylamino)-N-{2-[1R-(3-ethoxy-4-methoxyphenyl)-3-oxobutyl]-1,3-dioxoisoindolin-4-yl}acetamide hydrochloride as a white solid (0.45 g, %); mp 118-120° C.; $^1$H NMR (DMSO-$d_6$) δ 10.60 (s, 1H), 10.29 (s, 1H), 8.16 (d, J=8.2 Hz, 1H), 7.84 (t, J=7.6 Hz, 1H), 7.67 (d, J=7.2 Hz, 1H), 6.97 (s, 1H), 6.88 (s, 2H), 5.62-5.56 (dd, J=5.9 and 8.8 Hz, 1H), 4.27 (s, 2H), 3.98 (q, J=7.0 Hz, 2H), 3.77-3.66 (m, 1H), 3.70 (s, 3H), 3.51-3.41 (dd, J=6.0 and 18.1 Hz, 1H), 2.88 (s, 6H), 2.11 (s, 3H), 1.30 (t, J=6.9 Hz, 3H); $^{13}$C NMR (DMSO-$d_6$) δ 205.81, 167.18, 167.12, 164.35, 148.49, 147.76, 135.83, 134.11, 131.78, 131.47, 128.05, 119.64, 119.42, 119.26, 112.17, 111.76, 63.76, 57.88, 55.48, 48.90, 44.25, 43.27, 29.88, 14.70; Anal. Calcd. For $C_{26}H_{30}N_3O_6Cl$+0.27$H_2O$: C, 59.01; H, 6.05; N, 8.26; Cl, 6.97. Found: C, 59.06; H, 6.09; N, 8.14; Cl, 6.97.

Example 39

Tablets, each containing 50 mg of 2-[1-(3-ethoxy-4-methoxyphenyl)-2-methylsulfonylethyl]-4,5-diaminoisoindoline-1,3-dione, can be prepared in the following manner:

| Constituents (for 1000 tablets) | |
|---|---|
| 2-[1-(3-ethoxy-4-methoxyphenyl)-2-methylsulfonylethyl]-4,5-diamino-isoindoline-1,3-dione | 50.0 g |
| lactose | 50.7 g |
| wheat starch | 7.5 g |
| polyethylene glycol 6000 | 5.0 g |
| talc | 5.0 g |
| magnesium stearate | 1.8 g |
| demineralized water | q.s. |

The solid ingredients are first forced through a sieve of 0.6 mm mesh width. The active ingredient, lactose, talc, magnesium stearate and half of the starch then are mixed. The other half of the starch is suspended in 40 mL of water and this suspension is added to a boiling solution of the polyethylene glycol in 100 mL of water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

Example 40

Tablets, each containing 100 mg of 7-[1-(3-ethoxy-4-methoxyphenyl)-2-methylsulfonylethyl]-3-pyrrolino[3,4-e]benzimidazole-6,8-dione, can be prepared in the following manner:

| Constituents (for 1000 tablets) | |
|---|---|
| 7-[1-(3-ethoxy-4-methoxyphenyl)-2-methylsulfonylethyl]-3-pyrrolino[3,4-e]benz-imidazole-6,8-dione | 100.0 g |
| lactose | 100.0 g |
| wheat starch | 47.0 g |
| magnesium stearate | 3.0 g |

All the solid ingredients are first forced through a sieve of 0.6 mm mesh width. The active ingredient, lactose, magnesium stearate and half of the starch then are mixed. The other half of the starch is suspended in 40 mL of water and this suspension is added to 100 mL of boiling water. The resulting paste is added to the pulverulent substances and the mixture is granulated, if necessary with the addition of water. The granulate is dried overnight at 35° C., forced through a sieve of 1.2 mm mesh width and compressed to form tablets of approximately 6 mm diameter which are concave on both sides.

Example 41

Tablets for chewing, each containing 75 mg of 2-[1-(3-ethoxy-4-methoxyphenyl)-2-methylsulfonylethyl]-3-pyrrolino[3,4-f]quinoxaline-1,3-dione, can be prepared in the following manner:

| Composition (for 1000 tablets) | |
|---|---|
| 2-[1-(3-ethoxy-4-methoxyphenyl)-2-methylsulfonylethyl]-3-pyrrolino[3,4-f]quinoxaline-1,3-dione | 75.0 g |
| mannitol | 230.0 g |
| lactose | 150.0 g |
| talc | 21.0 g |
| glycine | 12.5 g |
| stearie acid | 10.0 g |
| saccharin | 1.5 g |
| 5% gelatin solution | q.s. |

All the solid ingredients are first forced through a sieve of 0.25 mm mesh width. The mannitol and the lactose are mixed, granulated with the addition of gelatin solution, forced through a sieve of 2 mm mesh width, dried at 50° C. and again forced through a sieve of 1.7 mm mesh width. 3-(3-Ethoxy-4-methoxyphenyl)-N-hydroxy-3-phthalimidopropionamide, the glycine and the saccharin are carefully mixed, the mannitol, the lactose granulate, the stearic acid and the talc are added and the whole is mixed thoroughly and compressed to form tablets of approximately 10 mm diameter which are concave on both sides and have a breaking groove on the upper side.

Example 42

Tablets, each containing 10 mg N-{2-[1-(3-ethoxy-4-methoxyphenyl)-3-oxobutyl]-1,3-dioxoisoindolin-4-yl}acetamide, can be prepared in the following manner:

| Composition (for 1000 tablets) | |
|---|---|
| N-{2-[1-(3-ethoxy-4-methoxyphenyl)-3-oxobutyl]-1,3-dioxoisoindolin-4-yl}acetamide | 10.0 g |
| lactose | 328.5 g |
| corn starch | 17.5 g |
| polyethylene glycol 6000 | 5.0 g |
| talc | 25.0 g |
| magnesium stearate | 4.0 g |
| demineralized water | q.s. |

The solid ingredients are first forced through a sieve of 0.6 mm mesh width. Then the active imide ingredient, lactose, talc, magnesium stearate and half of the starch are intimately mixed. The other half of the starch is suspended in 65 mL of water and this suspension is added to a boiling solution of the polyethylene glycol in 260 mL of water. The resulting paste is added to the pulverulent substances, and the whole is mixed and granulated, if necessary with the addition of water. The granulate is dried overnight at 35° C., forced through a sieve of 1.2 mm mesh width and compressed to form tablets of approximately 10 mm diameter which are concave on both sides and have a breaking notch on the upper side.

Example 43

Gelatin dry-filled capsules, each containing 100 mg of N-{2-[1R-(3-ethoxy-4-methoxyphenyl)-3-oxobutyl]-1,3-dioxoisoindolin-4-yl}acetamide, can be prepared in the following manner:

| Composition (for 1000 capsules) | |
|---|---|
| N-{2-[1R-(3-ethoxy-4-methoxyphenyl)-3-oxobutyl]-1,3-dioxoisoindolin-4-yl}-acetamide | 100.0 g |
| microcrystalline cellulose | 30.0 g |
| sodium lauryl sulfate | 2.0 g |
| magnesium stearate | 8.0 g |

The sodium lauryl sulfate is sieved into the N-{2-[1R-(3-ethoxy-4-methoxyphenyl)-3-oxobutyl]-1,3-dioxoisoindolin-4-yl}acetamide through a sieve of 0.2 mm mesh width and the two components are intimately mixed for 10 minutes. The microcrystalline cellulose is then added through a sieve of 0.9 mm mesh width and the whole is again intimately mixed for 10 minutes. Finally, the magnesium stearate is added through a sieve of 0.8 mm width and, after mixing for a further 3 minutes, the mixture is introduced in portions of 140 mg each into size 0 (elongated) gelatin dry-fill capsules.

Example 44

A 0.2% injection or infusion solution can be prepared, for example, in the following manner:

| | |
|---|---|
| 2-(dimethylamino)-N-{2-[1-(3-ethoxy-4-methoxyphenyl)-3-oxobutyl]-1,3-dioxoisoindolin-4-yl}-acetamide hydrochloride | 5.0 g |
| sodium chloride | 22.5 g |
| phosphate buffer pH 7.4 | 300.0 g |
| demineralized water | to 2500.0 mL |

2-(Dimethylamino)-N-{2-[1-(3-ethoxy-4-methoxyphenyl)-3-oxobutyl]-1,3-dioxoisoindolin-4-yl}acetamide hydrochloride is dissolved in 1000 mL of water and filtered through a microfilter. The buffer solution is added and the whole is made up to 2500 mL with water. To prepare dosage unit forms, portions of 1.0 or 2.5 mL each are introduced into glass ampoules (each containing respectively 2.0 or 5.0 mg of imide).

Example 45

Cyclopentyl-N-{2-[1-(3-ethoxy-4-methoxyphenyl)-2-(methylsulfonyl)ethyl]-1,3-dioxoisoindolin-4-yl}carboxamide A mixture of 2-[1-(3-ethoxy-4-methoxyphenyl)-2-(methylsulfonyl)ethyl]-4-aminoisoindoline-1,3-dione (0.85 g, 2.0 mmol) and cyclopentanecarbonyl chloride (0.8 mL, 6.6 mmol) was heated at 100° C. for 30 min. The mixture was cooled to room temperature. Methanol (10 mL) was added to the mixture. The mixture was stirred at 0° C. for 1 h. The resulting suspension was filtered to yield a solid. This solid was stirred in ether (10 mL) for 1 h. The suspension was filtered and washed with ether to give cyclopentyl-N-2-[1-(3-ethoxy-4-methoxyphenyl)-2-(methylsulfonyl)ethyl]-1,3-dioxoisoindolin-4-yl}carboxamide as a white solid (400 mg, 38% yield): mp, 134-136° C.; $^1$H NMR ($CDCl_3$) δ 1.49 (t, J=6.9 Hz, 3H, $CH_3$), 1.57-2.06 (m, 8H, C5$H_8$), 2.76-2.83 (m, 1H, CH), 2.87 (s, 3H, $CH_3$), 3.75 (dd, J=4.6, 14.4 Hz, 1H, CHH), 3.87 (s, 3H, $CH_3$), 4.12 (q, J=7.0 Hz, 2H, $CH_2$), 4.56 (dd, J=10.3, 14.4 Hz, 1H, CHH), 5.88 (dd, J=4.5, 10.3 Hz, 1H, NCH), 6.84-6.87 (m, 1H, Ar), 7.10-7.14 (m, 2H, Ar), 7.48 (d, J=7.2 Hz, 1H, Ar), 7.66 (t, J=7.5 Hz, 1H, Ar), 8.79 (d, J=8.4 Hz, 1H, Ar), 9.54 (s, 1H, NH); $^{13}$C NMR ($CDCl_3$) δ14.61, 25.81, 30.19, 30.23, 41.57, 47.14, 48.6, 554.62, 55.88, 64.47, 111.42, 112.41, 115.08, 117.92, 120.29, 124.98, 129.28, 130.98, 136.02, 137.89, 148.58, 149.71, 167.53, 169.48, 175.45; Anal Calcd for $C_{26}H_{30}N_2O_7S$+0.1$H_2O$: C, 60.47; H, 5.89; N, 5.42; $H_2O$, 0.35. Found: C, 60.22; H, 5.67; N, 5.44; $H_2O$, 0.24.

Example 46

3-(Dimethylamino)-N-{2-[1-(3-ethoxy-4-methoxyphenyl)-2-(methylsulfonyl)ethyl]-1,3-dioxoisoindolin-4-yl}propanamide A mixture of 2-[1'-(3-ethoxy-4-methoxyphenyl)-2-(methylsulfonyl)ethyl]-4-aminoisoindoline-1,3-dione (0.80 g, 1.9 mmol) and 2-bromopropionyl chloride (0.8 mL, 7.9 mmol) was healed at 100° C. for 30 min. The mixture was cooled to room temperature. Methanol (10 mL) was added to the mixture. The solvent was removed in vacuo to give an oil. The oil was stirred in ether (10 mL) for 1 day. The resulting suspension was filtered and the solid washed with ether to give 3-bromo-N-{2-[1-(3-ethoxy-4-methoxyphenyl)-2-(methylsulfonyl)ethyl]-1,3-dioxoisoindolin-4-yl}propanamide as a yellow solid (0.84 g, 80% yield). A portion of the isolated bromide (620 mg, 1.2 mmol) and dimethylamine (2 mL, 2M in methanol, 4 mmol) was stirred at room temperature for 3 h. The resulting suspension was filtered and washed with methanol to yield the crude product as a yellow solid. The solid was purified by column chromatography to give 3-(dimethylamino)-N-{2-[1-(3-ethoxy-4-methoxyphenyl)-2-(methylsulfonyl)ethyl]-1,3-dioxoisoindolin-4-yl}propanamide as a white solid (180 mg, 30% yield): mp, 163-165° C.; $^1$H NMR ($CDCl_3$) δ 1.47 (t, J=6.9 Hz, 3H, $CH_3$), 2.38 (s, 6H, $CH_3$), 2.59 (t, J=5.7 Hz, 2H, $CH_2$), 2.70 (t, J=5.9 Hz, 2H, $CH_2$), 2.82 (s, 3H, $CH_3$), 3.78-3.85 (m, 1H, CHH), 3.86 (s, 3H, $CH_3$), 4.10 (q, J=7.0 Hz, 2H, $CH_2$), 4.49 (dd, J=9.8, 14.6 Hz, 1H, CHH), 5.86 (dd, J=4.9, 9.7 Hz, 1H, NCH), 6.82-6.85 (m, 1H, Ar), 7.10-7.13 (m, 2H, Ar), 7.48 (d, J=7.2 Hz, 1H, Ar), 7.63 (t, J=7.5 Hz, 1H, Ar), 8.82 (d, J=8.4 Hz, 1H, Ar), 11.36 (s, 1H, NH); $^{13}$C NMR ($CDCl_3$) δ 14.62, 34.85, 41.49, 44.65, 48.74, 54.31, 55.01, 55.88, 64.44, 111.43, 112.52, 115.99, 117.93, 120.39, 120.08, 129.52, 131.42, 135.59, 137.33, 148.55, 149.67, 168.00, 168.16, 171.86; Anal Calcd for $C_{25}H_{31}N_3O_7S$: C, 58.01; H, 6.04; N, 8.12. Found: C, 57.75; H, 5.86; N, 7.91.

Example 47

2-(Dimethylamino)-N-{2-[1-(3-ethoxy-4-methoxyphenyl)-2-(methylsulfonyl)ethyl]-1,3-dioxoisoindolin-4-yl}propanamide, hydrogen chloride Step 1: A solution of 4-amino-2-[1-(3-ethoxy-4-methoxyphenyl)-2-(methylsulfonyl)ethyl]isoindoline-1,3-dione (500 mg, 1.20 mmol) and 2-bromopropionyl bromide (0.140 mL, 1.34 mmol) in methylene chloride (10 mL) was stirred at room temperature overnight. An additional 0.1 mL of 2-bromopropionyl bromide (1 mol) was added and the mixture stirred overnight. To the mixture was added brine (4 mL), Sodium bicarbonate (sat, 10 mL) and methylene chloride (15 mL). The organic layer was separated, was washed with brine (10 mL), and dried over magnesium sulfate. The solvent was removed in vacuo to give a yellow oil. The oil was slurried in ether (10 mL). The resulting suspension was filtered and the solid washed with ether to give 2-bromo-N-{2-[1-(3-ethoxy-4-methoxyphenyl)-2-(methylsulfonyl)ethyl]-1,3-dioxoisoindolin-4-yl}propanamide as a white solid (500 mg, 76% yield): $^1$H NMR ($CDCl_3$) δ 1.46 (t, J=6.9 Hz, 3H, $CH_3$), 1.97 (d, J=6.9 Hz, 3H, $CH_3$), 2.86 (s, 3H, $CH_3$), 3.75 (dd, J=4.5, 14.4 Hz, 1H, CHH), 3.85 (s, 3H, $CH_3$), 4.49-4.59 (m, 2H, CHH, CH), 4.09 (q, J=6.9 Hz, 2H, $CH_2$), 5.87 (dd, J=4.4, 10.3 Hz, 1H, NCH), 6.82-6.85 (m, 1H, Ar), 7.09-7.13 (m, 2H, Ar), 7.53 (d, J=7.3 Hz, 1H, Ar), 7.68 (t, J=7.5 Hz, 1H, Ar), 8.73 (d, J=8.4 Hz, 1H, Ar), 10.19 (s, 1H, NH); $^{13}$C NMR ($CDCl_3$) δ 14.61, 22.42, 41.54, 43.78, 48.67, 54.44, 55.87, 64.45, 111.39, 112.3, 116.10, 116.79, 120.35, 124.76, 129.14, 131.13, 136.02, 136.82, 148.55, 149.70, 167.28, 168.42, 169.11.

Step 2: To a suspension of 2-bromo-N-{2-[1-(3-ethoxy-4-methoxyphenyl)-2-(methylsulfonyl)ethyl]-1,3-dioxoisoindolin-4-yl}propanamide (500 mg, 0.9 mmol) in acetonitrile (5 mL) was added dimethylamine in methanol (1.5 mL, 2M, 3.0 mmol) at room temperature and the mixture was stirred for 2 days. The mixture was diluted with methylene chloride (50 mL) and sodium hydrogen carbonate (25 mL). The organic layer was separated, washed with brine (25 mL), and dried over magnesium sulfate. The solvent was removed in vacuo to give an oil. To a solution of the oil in ethyl acetate (20 mL) was added hydrogen chloride in ether (1.5 mL, 1N hydrogen chloride, 1.5 mmol). The resulting suspension was filtered and washed with ethyl acetate (10 mL) to give 2-(dimethylamino)-N-{2-[1-(3-ethoxy-4-methoxyphenyl)-2-(methylsulfonyl)ethyl]-1,3-dioxoisoindolin-4-yl}propanamide, hydrogen chloride as a white solid (290 mg, 58% yield): mp, 138-140° C.; $^1$H NMR (DMSO-$d_6$) δ 1.32 (t, J=6.9 Hz, 3H, $CH_3$), 1.56 (brs, 3H, $CH_3$), 2.83 (brs, 6H, $CH_3$), 3.01 (s, 3H, $CH_3$), 3.73 (s, 3H, $CH_3$), 4.02 (q, J=6.9 Hz, 2H, $CH_2$), 4.15 (dd, J=4.4, 14.2 Hz, 1H, CHH), 4.27 (s, 1H, CH), 4.34 (dd, J=10.6, 14.3 Hz, 1H, CHH), 5.78 (dd, J=4.3, 10.3 Hz, 1H, NCH), 6.91-6.99 (m, 2H, Ar), 7.72 (d, J=7.1 Hz, 1H<Ar), 7.87 (d, J=7.5 Hz, 1H, Ar), 8.14 (m, 1H, Ar), 10.4 (brs, 1H, HCl), 10.71 (s, 1H, NH); $^{13}$C NMR (DMSO-d6) δ 13.42, 14.67, 41.07, 41.47, 47.31, 52.98, 55.51, 52.74, 63.84, 111.75, 112.31, 119.70, 120.16, 128.92, 129.47, 131.80, 134.05, 135.87, 147.87, 148.91, 166.66, 166.86, 167.65, 168.53; Anal Calcd for $C_{25}H_{31}N_3O_7S$+1.1HCl+0.6$H_2O$: C, 52.82; H, 5.90; N, 7.39, Cl, 6.86, $H_2O$, 1.90. Found: C, 52.57; H, 5.77; N, 7.10; Cl, 6.90; $H_2O$, 1.47.

Example 48

N-{2-[(1R)-1-(3-ethoxy-4-methoxyphenyl)-2-(methylsulfonyl)ethyl]-1,3-dioxoisoindolin-4-yl}-2-(dimethylamino)acetamide hydrogen chloride A mixture of N-{2-[(1R)-1-(3-ethoxy-4-methoxyphenyl)-2-(methylsulfonyl)ethyl]-1,3-dioxoisoindolin-4-yl}-2-chloroacetamide (0.70 g, 1.41 mmol), and dimethylamine in tetrahydrofuran (2.4 mL, 2N, 4.8 mmol) in acetonitrile (15 mL) was stirred at room temperature overnight. The solvent was removed in vacuo to yield an oil. The oil was stirred in ethanol (5 mL). The suspension was filtered and washed with ethanol to give a white solid. To a solution of the solid in ethyl acetate (5 mL) was added hydrogen chloride in ether (1.5 mL, 1N). The resulting suspension was filtered and the solid was washed with ether to give N-{2-[(1R)-1-(3-ethoxy-4-methoxyphenyl)-2-(methylsulfonyl)ethyl]-1,3-dioxoisoindolin-4-yl}-2-(dimethylamino)acetamide hydrogen chloride as a yellow solid (480 mg, 63% yield); mp, 192-194° C.; $^1$H NMR (DMSO-d6) δ 1.33 (t, J=6.9 Hz, 3H, $CH_3$), 2.87 (s, 6H, $2CH_3$), 3.03 (s, 3H, $CH_3$), 3.74 (s, 3H, $CH_3$), 4.02 (q, J=7.0 Hz, 2H, $CH_2$), 4.16 (dd, J=4.2, 14.3 Hz, 1H, CHH), 4.25 (brs, 2H, $CH_2$), 4.34 (dd, J=10.8, 14.4 Hz, 1H, CHH), 5.79 (dd, J=4.2, 10.4 Hz, 1H, NCH), 6.92-6.99 (m, 2H, Ar), 7.08 (s, 1H, Ar), 7.69 (d, J=7.3 Hz, 1H, Ar), 7.88 (t, J=7.7 Hz, 1H, Ar), 8.21-8.27 (m, 1H, Ar), 10.29 (s, 1H, HCl), 10.64 (s, 1H, NH); $^{13}$C NMR (DMSO-d6) δ 14.65, 41.04, 43.36, 47.23, 52.86, 55.51, 58.09, 63.86, 111.79, 112.39, 119.22, 119.68, 127.78, 127.99, 129.42, 131.76, 134.25, 134.34, 135.95, 147.87, 148.92, 164.60, 166.79; Anal Calcd for $C_{24}H_{29}N_3O_7S$+1HCl: C, 53.38; H, 5.60; N, 7.78; Cl, 6.56. Found: C, 53.52; H, 5.70; N, 7.61; Cl, 6.44.

Example 49

N-(2-[(1S)-1-(3-ethoxy-4-methoxyphenyl)-2-(methylsulfonyl)ethyl]-1,3-dioxoisoindolin-4-yl)-2-(dimethylamino)acetamide hydrogen chloride A mixture of N-{2-[(1S)-1-(3-ethoxy-4-methoxyphenyl)-2-(methylsulfonyl)ethyl]-1,3-dioxoisoindolin-4-yl}-2-chloroacetamide (1.79 g, 3.61 mmol), and dimethylamine in tetrahydrofuran (6.1 mL, 2N, 12.2 mmol) in acetonitrile (17 mL) was stirred at room temperature overnight. The solvent was removed in vacuo to give an oil. The oil was stirred in ethanol (10 mL). The resulting suspension was filtered and the solid washed with ethanol to give a white solid. The solid was purified by column chromatography (Silica Gel, 1:3 ethyl acetate:methylene chloride) to give a white solid (900 mg, 50% yield). To this solid in ethyl acetate (10 mL) was added hydrogen chloride in ether (2.6 mL, 1N). After 5 min, ether (10 mL) was added to this solution to give a suspension. The suspension was filtered and the solid washed with ether to give N-{2-[(1S)-1-(3-ethoxy-4-methoxyphenyl)-2-(methylsulfonyl)ethyl]-1,3-dioxoisoindolin-4-yl}-2-(dimethylamino)acetamide hydrogen chloride as a yellow solid (830 mg, 86% yield); mp, 202-204° C.; $^1$H NMR (DMSO-d6) δ 1.33 (t, J=6.9 Hz, 3H, $CH_3$), 2.87 (s, 6H, $2CH_3$), 3.03 (s, 3H, $CH_3$), 3.74 (s, 3H, $CH_3$), 4.02 (q, J=7.0 Hz, 2H, $CH_2$), 4.16 (dd, J=4.2, 14.3 Hz, 1H, CHH), 4.25 (brs, 2H, $CH_2$), 4.34 (dd, J=10.8, 14.4 Hz, 1H, CHH), 5.79 (dd, J=4.2, 10.4 Hz, 1H, NCH), 6.92-6.99 (m, 2H, Ar), 7.08 (s, 1H, Ar), 7.69 (d, J=7.3 Hz, 1H, Ar), 7.88 (t, J=7.7 Hz, 1H, Ar), 8.21-8.27 (m, 1H, Ar), 10.29 (s, 1H, HCl), 10.64 (s, 1H, NH); $^{13}$C NMR (DMSO-d6) δ 14.65, 41.04, 43.36, 47.23, 52.86, 55.51, 58.09, 63.86, 111.79, 112.39, 119.22, 119.68, 127.78, 127.99, 129.42, 131.76, 134.25, 134.34, 135.95, 147.87, 148.92, 164.60, 166.79; Anal Calcd for $C_{24}H_{29}N_3O_7S$+1HCl+0.6$H_2O$: C, 52.33; H, 5.71; N, 7.63; Cl, 6.44; $H_2O$, 1.96. Found: C, 52.46; H, 5.63; N, 7.46; Cl, 6.43; $H_2O$, 2.16.

Example 50

4-{3-[(Dimethylamino)methyl]pyrrolyl}-2-[1-(3-ethoxy-4-methoxyphenyl)-2-(methylsulfonyl)ethyl] isoindoline-1,3-dione, hydrogen chloride A mixture of 1-{2-[1-(3-ethoxy-4-methoxyphenyl)-2-(methylsulfonyl)ethyl]-1,3-dioxoisoindolin-4-yl}pyrrole-3-carbaldehyde (0.840 g, 1.69 mmol), dimethylamine in tetrahydrofuran (2.6 mL, 2N, 5.2 mmol), and molecular sieves in methylene chloride (10 mL) was stirred at room temperature overnight. The mixture was cooled to 0° C. To the mixture was added methanol (10 mL), and sodium borohydride (32 mg, 0.84 mmol). After 1.5 h, the suspension was filtered thru a pad of magnesium sulfate. The magnesium sulfate pad was washed with methylene chloride (50 mL). The filtrate was washed with ammonium chloride (aq) (sat, 50 mL) and sodium hydrogen carbonate (sat, 50 mL). The solvent was removed in vacuo to give an oil. The oil was diluted with ethyl acetate (50 mL) and hydrogen chloride (100 mL, 1N). The organic layer was separated and was extracted with 1 N hydrogen chloride (2×100 mL). The combined aqueous layers was washed with ethyl acetate (30 mL), and then extracted with methylene chloride (3×50 mL). The combined methylene chloride layers were concentrated to give a solid. The solid was slurried in iso-propanol (15 mL). The suspension was filtered and the solid washed with ethanol and then dried to yield 4-{3-[(dimethylamino)methyl]pyrrolyl}-2-[1-(3-ethoxy-4-methoxyphenyl)-2-(methylsulfonyl)ethyl]isoindoline-1,3-dione, hydrogen chloride as a white solid (370 mg, 39% yield); mp, 158-160° C.; $^1$H NMR ($CDCl_3$) δ 1.46 (t, J=6.9 Hz, 3H, $CH_3$), 2.78 (s, 3H, $CH_3$), 2.80 (s, 3H, $CH_3$), 2.89 (s, 3H, $CH_3$), 3.69 (dd, J=4.2, 14 Hz, 1H, CHH), 3.84 (s, 3H, $CH_3$), 4.04-4.12 (m, 4H, $CH_2$, $CH_2$), 4.59 (dd, J=11, 14 Hz, 1H, CHH), 5.89 (dd, J=4.2, 11 Hz, 1H, NCH), 6.50-6.52 (m, 1H, Ar), 6.83 (d, J=8 Hz, 1H, Ar), 7.08-7.14 (m, 3H, Ar), 7.47 (brs, 1H, Ar), 7.63-7.67 (m, 1H, Ar), 7.75-7.83 (m, 2H, Ar), 12.46 (brs, 1H, ClH); $^{13}$C NMR ($CDCl_3$) δ 14.63, 41.37, 41.42, 41.58, 48.67, 53.86, 54.16, 55.87, 64.48, 111.39, 112.20, 112.45, 112.58, 120.42, 121.59, 121.95, 123.10, 124.95, 128.97, 130.24, 133.68, 135.72, 137.37, 148.53, 149.72, 165.51, 166.69; Anal Calcd for $C_{27}H_{31}N_3O_6S$+1HCl+0.8$H_2O$: C, 56.25; H, 5.87; N, 7.29; Cl, 6.15; $H_2O$, 2.50. Found: C, 56.51; H, 5.78; N, 7.08; Cl, 6.05; $H_2O$, 2.63.

Example 51

Cyclopropyl-N-{2-[(1S)-1-(3-ethoxy-4-methoxyphenyl)-2-(methylsulfonyl)ethyl]-1,3-dioxoisoindolin-4-yl}-carboxamide A stirred mixture of 2-[(1S)-1-(3-ethoxy-4-methoxyphenyl)-2-(methylsulfonyl)ethyl]-4-aminoisoindoline-1,3-dione (1.3 g, 3.1 mmol) and cyclopropane carbonyl chloride (3 mL) was heated to reflux for 45 min. To the cooled mixture was added methanol (10 mL) at 0° C. and the mixture stirred for 30 min. The solvent was removed in vacuo to give an oil. The oil was stirred in ethanol (10 mL) for 2 h to give a suspension. The suspension was filtered and the solid washed with ethanol to give cyclopropyl-N-{2-[(1S)-1-(3-ethoxy-4-methoxyphenyl)-2-(methylsulfonyl)ethyl]-1,3-dioxoisoindolin-4-yl}carboxamide as a white solid (1.3 g, 86% yield); mp, 140-141° C.; $^1$H NMR ($CDCl_3$) δ 0.92-0.99 (m, 2H, 2CHH), 1.11-1.17 (m, 2H, 2CHH), 1.48 (t, J=6.9 Hz, 3H, $CH_3$), 1.61-1.71 (m, 1H, CH), 2.88 (s, 3H, $CH_3$), 3.75 (dd, J=4.4, 14.3 Hz, 1H, CHH), 3.86 (s, 3H, $CH_3$), 4.12 (q, J=7.1 Hz, 2H, $CH_2$), 4.57 (dd, J=10.4, 14.3 Hz, 1H, CHH), 5.89 (dd, J=4.4, 10.3 Hz, 1H, NCH), 6.84-6.88 (m, 1H, Ar), 7.11-7.15 (m, 2H, Ar), 7.48 (d, J=7.2 Hz, 1H, Ar), 7.65 (t, J=7.4 Hz, 1H, Ar), 8.76 (d, J=8.5 Hz, 1H, Ar), 9.69 (s, 1H, NH); $^{13}$C NMR ($CDCl_3$) δ 8.71, 14.62, 16.16, 41.58, 48.59, 54.60, 55.89, 64.50, 111.49, 112.44, 114.83, 117.91, 120.26, 124.99, 129.27, 130.99, 136.02, 137.77, 148.63, 149.76, 167.49, 169.52, 172.79; Anal Calcd for $C_{24}H_{26}N_2O_7S$: C, 59.25; H, 5.39; N, 5.76. Found: C, 58.92; H, 5.21; N, 5.56.

Example 52

2-[1-(3,4-dimethoxyphenyl)-2-(methylsulfonyl) ethyl]-4-pyrrolylisoindoline-1,3-dione A stirred mixture of 2-[1-(3,4-dimethoxyphenyl)-2-(methylsulfonyl)ethyl]-4-aminoisoindoline-1,3-dione (0.92 g, 2.3 mmol) and 2,5-dimethoxy tetrahydrofuran (0.30 mL, 2.3 mmol) in acetic acid (9 mL) was heated to reflux for 2 h. The solvent was removed in vacuo to give an oil. The oil was purified by column chromatography (Silica Gel, 1:4 ethyl acetate:methylene chloride) to give 2-[1-(3,4-dimethoxyphenyl)-2-(methylsulfonyl)ethyl]-4-pyrrolylisoindoline-1,3-dione as a yellow solid (0.64 g, 62% yield): mp, 116-118° C.; $^1$H NMR ($CDCl_3$) δ 2.87 (s, 3H, $CH_3$), 3.71 (dd, J=4, 14 Hz, 1H, CHH), 3.85 (s, 3H, $CH_3$), 3.88 (s, 3H, $CH_3$), 4.61 (dd, J=11, 14 Hz, 1H, CHH), 5.92 (dd, J=4, 11 Hz, 1H, NCH), 6.39 (t, J=2.0 Hz, 2H, Ar), 6.82 (d, J=8 Hz, 1H, Ar), 7.09-7.10 (m, 1H, Ar), 7.15-7.17 (m, 3H, Ar), 7.59-7.64 (m, 1H, Ar), 7.73-7.77 (m, 2H, Ar); $^{13}$C NMR ($CDCl_3$) δ 41.44, 48.73, 54.26, 55.83, 55.89, 110.75, 111.12, 120.55, 120.99, 121.07, 128.99, 129.31, 130.11, 133.71, 135.37, 138.61, 149.16, 149.37, 165.77, 166.82; Anal Calcd for $C_{23}H_{22}N_2O_6S$: C, 60.78; H, 4.88; N, 6.16. Found: C, 60.58; H, 5.01; N, 5.88.

Example 53

N-{2-[1-(3,4-dimethoxyphenyl)-2-(methylsulfonyl)ethyl]-1,3-dioxoisoindolin-4-yl}-2-(dimethylamino)acetamide Hydrogen chloride A mixture of N-{2-[1-(3,4-dimethoxyphenyl)-2-(methylsulfonyl)ethyl]-1,3-dioxoisoindolin-4-yl}-2-chloroacetamide (1.3 g, 2.7 mmol), and dimethylamine in tetrahydrofuran (4.5 mL, 2N, 9.0 mmol) in acetonitrile (20 mL) was stirred at room temperature overnight. The solvent was removed in vacuo to give an oil. The oil was stirred in ethanol (5 mL). The resulting suspension was filtered and the solid washed with ethanol to give a yellow solid. To a stirred solution of the solid in ethyl acetate (10 mL) was added hydrogen chloride in ether (3.0 mL, 1N). After 5 min, ether (10 mL) was added. The resulting suspension was filtered and washed with ether to yield N-{2-[1-(3,4-dimethoxyphenyl)-2-(methylsulfonyl)ethyl]-1,3-dioxoisoindolin-4-yl}-2-(dimethylamino)acetamide hydrogen chloride as a yellow solid (1.07 g, 74% yield); mp, 178-180° C.; $^1$H NMR (DMSO-d6) δ 2.69 (brs, 6H, 2$CH_3$), 3.02 (s, 3H, $CH_3$), 3.73 (s, 3H, $CH_3$), 3.77 (s, 3H, $CH_3$), 3.88 (brs, 2H, $CH_2$), 4.16 (dd, J=4.2, 14.3 Hz, 1H, CHH), 4.34 (dd, J=10.8, 14.4 Hz, 1H, CHH), 5.79 (dd, J=4.2, 10.4 Hz, 1H, NCH), 6.92-6.97 (m, 2H, Ar), 7.10 (d, J=1.4 Hz, 1H, Ar), 7.65 (d, J=7.2 Hz, 1H, Ar), 7.85 (t, J=7.7 Hz, 1H, Ar), 8.37-8.40 (m, 1H, Ar), 10.15 (s, 1H, HCl), 10.68 (s, 1H, NH); $^{13}$C NMR (DMSO-d6) δ 41.06, 44.18, 47.31, 52.95, 55.55, 55.59, 59.85, 111.26, 111.65, 119.16, 119.69, 127.00, 129.49, 121.64, 134.99, 136.09, 148.71, 148.76, 166.92, 167.34; Anal Calcd for $C_{23}H_{27}N_3O_7S$+1.25 HCl+0.4$H_2O$: C, 50.94; H, 5.40; N, 7.75; Cl, 8.17; $H_2O$, 1.33. Found: C, 51.30; H, 5.50; N, 7.37; Cl, 8.28; $H_2O$, 1.68.

Example 54

Cyclopropyl-N-{2-[1-(3,4-dimethoxyphenyl)-2-(methylsulfonyl)ethyl]-1,3-dioxoisoindolin-4-yl}carboxamide A stirred mixture of 2-[1-(3,4-dimethoxyphenyl)-2-(methylsulfonyl)ethyl]-4-aminoisoindoline-1,3-dione (0.68 g, 1.7 mmol) and cyclopropane carbonyl chloride (1.3 mL) was heated to reflux for 25 min. To the mixture was added ethanol (10 mL) at 0° C. and kept for 30 min. The solvent was removed in vacuo to give a oil. The oil was stirred in ether (20 mL) for 30 min to give a suspension. The suspension was filtered and the solid washed with ether to give a white solid. The solid was purified by column chromatography (Silica Gel, 10% ethyl acetate in methylene chloride) to give cyclopropyl-N-{2-[1-(3,4-dimethoxyphenyl)-2-(methylsulfonyl)ethyl]-1,3-dioxoisoindolin-4-yl}carboxamide as a white solid (330 mg, 42% yield); mp, 130-132° C.; $^1$H NMR ($CDCl_3$) δ 0.92-0.98 (m, 2H, 2CHH), 1.09-1.14 (m, 2H, 2CHH), 1.61-1.64 (m, 1H, CH), 2.88 (s, 3H, $CH_3$), 3.73 (dd, J=4.4, 14.3 Hz, 1H, CHH), 3.86 (s, 3H, $CH_3$), 3.90 (s, 3H, $CH_3$), 4.58 (dd, J=10.4, 14.3 Hz, 1H, CHH), 5.90 (dd, J=4.4, 10.3 Hz, 1H, NCH), 6.84 (d, J=8 Hz, 1H, Ar), 7.09-7.14 (m, 2H, Ar), 7.47 (d, J=7.2 Hz, 1H, Ar), 7.65 (t, J=7.6 Hz, 1H, Ar), 8.75 (d, J=8.4 Hz, 1H, Ar), 9.68 (s, 1H, NH); $^{13}$C NMR ($CDCl_3$) δ 6.75, 16.13, 41.54, 48.43, 54.36, 55.81, 55.94, 110.98, 111.11, 114.78, 117.88, 120.27, 124.93, 129.30, 130.94, 136.00, 137.68, 149.19, 149.35, 167.45, 169.48, 172.79; Anal Calcd for $C_{23}H_{24}N_2O_7S$: C, 58.46; H, 5.12; N, 5.93. Found: C, 58.10; H, 5.16; N, 5.78.

Example 55

Cyclopropyl-N-{2-[1-(3-ethoxy-4-methoxyphenyl)-2-(methylsulfonyl)ethyl]-3-oxoisoindolin-4-yl}carboxamide A stirred mixture of 7-amino-2-[1-(3-ethoxy-4-methoxyphenyl)-2-(methylsulfonyl)ethyl]isoindolin-1-one (1.0 g, 2.5 mmol) and cyclopropane carbonyl chloride (1 mL) was heated to reflux for 7 min. To the cooled mixture was added methanol (3 mL) at 0° C. and the mixture was stirred for 30 min. To the suspension was added ethanol (5 mL). The suspension was filtered and washed with ethanol to give cyclopropyl-N-{2-[1-(3-ethoxy-4-methoxyphenyl)-2-(methylsulfonyl)ethyl]-3-oxoisoindolin-4-yl}carboxamide as an off-white solid (1.0 g, 86% yield); mp, 115-117° C.; $^1$H NMR ($CDCl_3$) δ 0.86-0.93 (m, 2H, 2CHH), 1.07-1.14 (m, 2H, 2CHH), 1.46 (t, J=6.9 Hz, 3H, $CH_3$), 1.63-1.73 (m, 1H, CH), 2.95 (s, 3H, $CH_3$), 3.68 (dd, J=4.4, 14.3 Hz, 1H, CHH), 3.86 (s, 3H, $CH_3$), 4.07 (q, J=7.1 Hz, 2H, $CH_2$), 4.20 (d, J=16.7 Hz, 1H, CHH), 4.21 (dd, J=9.9, 14.3 Hz, 1H, CHH), 4.44 (d, J=16.7 Hz, 1H, CHH), 5.73 (dd, J=4.3, 9.9 Hz, 1H, NCH), 6.84-7.02 (m, 4H, Ar), 7.44 (t, J=7.8 Hz, 1H, Ar), 8.43 (d, J=8.3 Hz, 1H, Ar), 10.46 (s, 1H, NH); $^{13}$C NMR ($CDCl_3$) δ 8.24, 14.61, 16.10, 41.43, 47.81, 51.55, 55.75, 55.88, 64.56, 111.46, 112.09, 116.69, 116.99, 117.76, 119.17, 129.27, 133.54, 138.06, 141.22, 148.84, 149.67, 169.96, 172.59; Anal Calcd for $C_{24}H_{28}N_2O_6S$+0.9$H_2O$: C, 58.98; H, 6.15; N, 5.73; $H_2O$, 3.32. Found: C, 58.62; H, 5.99; N, 5.53; $H_2O$, 3.15.

Example 56

2-(Dimethylamino)-N-{2-[1-(3-ethoxy-4-methoxyphenyl)-2-(methylsulfonyl)ethyl]-3-oxoisoindolin-4-yl}acetamide hydrogen chloride A mixture of 7-amino-2-[1-(3-ethoxy-4-methoxyphenyl)-2-(methylsulfonyl)ethyl]isoindolin-1-one (1.0 g, 2 mmol), and dimethylamine in tetrahydrofuran (3.6 mL, 2N, 7.2 mmol) in acetonitrile (25 mL) was stirred at room temperature overnight. The solvent was removed in vacuo to give a solid. The solid was recrystallized from ethanol (10 mL) to give a white solid. To stirred solution of the solid in ethyl acetate (10 mL) was added hydrogen chloride in ether (2.5 mL, 1N). After 5 min, ether (10 mL) was added to give a suspension. The suspension was filtered and the solid washed with ether to give 2-(dimethylamino)-N-{2-[1-(3-ethoxy-4-methoxyphenyl)-2-(methylsulfonyl)ethyl]-3-oxoisoindolin-4-yl}acetamide hydrogen chloride as a yellow solid (780 mg, 74% yield); mp, 145-147° C.; $^1$H NMR (DMSO-d6) δ 1.32 (t, J=7 Hz, 3H, $CH_3$), 2.87 (brs, 6H, $2CH_3$), 3.03 (s, 3H, $CH_3$), 3.73 (s, 3H, $CH_3$), 3.92-4.05 (m, 3H, CHH, $CH_2$), 4.17 (d, J=17.9 Hz, 1H, CHH), 4.31-4.41 (m, 3H, $CH_2$, CHH), 4.68 (d, J=17.9 Hz, 1H, CHH), 5.88 (dd, J=3.5, 10.7 Hz, 1H, NCH), 6.91-6.98 (m, 2H, Ar), 7.02 (s, 1H, Ar), 7.31 (d, J=7.3 Hz, 1H, Ar), 7.59 (t, J=7.9 Hz, 1H, Ar), 8.15 (d, J=8.0 Hz, 1H, Ar), 10.17 (s, 1H, HCl), 10.53 (s, 1H, NH); $^{13}C$ NMR (DMSO-d6) δ 14.72, 40.99, 43.40, 46.20, 48.81, 53.69, 55.32, 58.11, 63.93, 111.98, 112.16, 118.19, 118.58, 119.16, 119.76, 130.01, 133.01, 135.29, 142.55, 148.07, 148.88, 163.88, 167.45; Anal Calcd for $C_{24}H_{31}N_3O_6S$+1.1HCl+1.5$H_2O$: C, 51.78; H, 6.35; N, 7.55; Cl, 7.00; $H_2O$, 4.85. Found: C, 51.58; H, 6.13; N, 7.39; Cl, 6.87; $H_2O$, 3.34.

Example 57

Cyclopropyl-N-{2-[(1S)-1-(3-ethoxy-4-methoxyphenyl)-2-(methylsulfonyl)ethyl]-3-oxoisoindolin-4-yl}carboxamide A stirred mixture of 7-amino-2-[(1S)-1-(3-ethoxy-4-methoxyphenyl)-2-(methylsulfonyl)ethyl]isoindolin-1-one (1.7 g, 4.2 mmol) and cyclopropane carbonyl chloride (0.46 mL, 5.1 mmol) in tetrahydrofuran (10 mL) was heated to reflux for 15 min. To the mixture was added methanol (4 mL) at room temperature and the mixture stirred for 10 min. The solvent was removed in vacuo to give an oil. The oil was recrystallized from ethanol (20 mL) to give cyclopropyl-N-{2-[(1S)-1-(3-ethoxy-4-methoxyphenyl)-2-(methylsulfonyl)ethyl]-3-oxoisoindolin-4-yl}carboxamide as a white solid (1.4 g, 71% yield); mp, 172-174° C.; $^1H$ NMR ($CDCl_3$) δ 0.86-0.93 (m, 2H, 2CHH), 1.07-1.14 (m, 2H, 2CHH), 1.46 (t, J=6.9 Hz, 3H, $CH_3$), 1.63-1.73 (m, 1H, CH), 2.95 (s, 3H, $CH_3$), 3.68 (dd, J=4.4, 14.3 Hz, 1H, CHH), 3.86 (s, 3H, $CH_3$), 4.07 (q, J=7.1 Hz, 2H, $CH_2$), 4.20 (d, J=16.7 Hz, 1H, CHH), 4.21 (dd, J=9.9, 14.3 Hz, 1H, CHH), 4.44 (d, J=16.7 Hz, 1H, CHH), 5.73 (dd, J=4.3, 9.9 Hz, 1H, NCH), 6.84-7.02 (m, 4H, Ar), 7.44 (t, J=7.8 Hz, 1H, Ar), 8.43 (d, J=8.3 Hz, 1H, Ar), 10.46 (s, 1H, NH); $^{13}C$ NMR ($CDCl_3$) δ 8.24, 14.61, 16.10, 41.43, 47.81, 51.55, 55.75, 55.88, 64.56, 111.46, 112.09, 116.69, 116.99, 117.76, 119.17, 129.27, 133.54, 138.06, 141.22, 148.84, 149.67, 169.96, 172.59; Anal Calcd for $C_{24}H_{28}N_2O_6S$: C, 61.00; H, 5.97; N, 5.93. Found: C, 60.87; H, 6.13; N, 6.12.

Example 58

Cyclopropyl-N-{2-[(1R)-1-(3-ethoxy-4-methoxyphenyl)-2-(methylsulfonyl)ethyl]-3-oxoisoindolin-4-yl}carboxamide A stirred mixture of 7-amino-2-[(1R)-1-(3-ethoxy-4-methoxyphenyl)-2-(methylsulfonyl)ethyl]isoindolin-1-one (0.91 g, 2.2 mmol) and cyclopropane carbonyl chloride (0.25 mL, 2.8 mmol) in tetrahydrofuran (10 mL) was heated to reflux for 15 min. The solvent was removed in vacuo to give a solid. The solid was recrystallized from ethanol (10 mL) to give cyclopropyl-N-{2-[(1R)-1-(3-ethoxy-4-methoxyphenyl)-2-(methylsulfonyl)ethyl]-3-oxoisoindolin-4-yl}carboxamide as an off-white solid (0.61 g, 56% yield); mp, 173-175° C.; $^1H$ NMR ($CDCl_3$) δ 0.86-0.93 (m, 2H, 2CHH), 1.07-1.14 (m, 2H, 2CHH), 1.46 (t, J=6.9 Hz, 3H, $CH_3$), 1.63-1.73 (m, 1H, CH), 2.95 (s, 3H, $CH_3$), 3.68 (dd, J=4.4, 14.3 Hz, 1H, CHH), 3.86 (s, 3H, $CH_3$), 4.07 (q, J=7.1 Hz, 2H, $CH_2$), 4.20 (d, J=16.7 Hz, 1H, CHH), 4.21 (dd, J=9.9, 14.3 Hz, 1H, CHH), 4.44 (d, J=16.7 Hz, 1H, CHH), 5.73 (dd, J=4.3, 9.9 Hz, 1H, NCH), 6.84-7.02 (m, 4H, Ar), 7.44 (t, J=7.8 Hz, 1H, Ar), 8.43 (d, J=8.3 Hz, 1H, Ar), 10.46 (s, 1H, NH); $^{13}C$ NMR ($CDCl_3$) δ 8.24, 14.61, 16.10, 41.43, 47.81, 51.55, 55.75, 55.88, 64.56, 111.46, 112.09, 116.69, 116.99, 117.76, 119.17, 129.27, 133.54, 138.06, 141.22, 148.84, 149.67, 169.96, 172.59; Anal Calcd for $C_{24}H_{28}N_2O_6S$: C, 61.00; H, 5.97; N, 5.93. Found: C, 60.73; H, 5.91; N, 5.69.

Example 59

(3R)-3-[7-(Acetylamino)-1-oxoisoindolin-2-yl]-3-(3-ethoxy-4-methoxyphenyl)-N,N-dimethylpropimamide A stirred mixture of (3R)-3-(7-amino-1-oxoisoindolin-2-yl)-3-(3-ethoxy-4-methoxyphenyl)-N,N-dimethylpropanamide (400 mg, 1 mmol) and acetyl chloride (0.1 mL, 1.4 mmol) in tetrahydrofuran (5 mL) was heated to reflux for 2 h. To the mixture was added 50% sodium hydrogen carbonate (40 mL) and ethyl acetate (50 mL). The organic layer was washed with sodium hydrogen carbonate (sat, 20 mL), brine (20 mL), and dried over magnesium sulfate. The solvent was removed in vacuo to give an oil. The oil was purified by column chromatography (Silica Gel, 1.5:1 ethyl acetate:methylene chloride) to give (3R)-3-[7-(acetylamino)-1-oxoisoindolin-2-yl]-3-(3-ethoxy-4-methoxyphenyl)-N,N-dimethylpropanamide as a white solid (0.25 g, 57% yield); mp, 88-90° C.; $^1H$ NMR ($CDCl_3$)~1.43 (t, J=6.9 Hz, 3H, $CH_3$), 2.22 (s, 3H, $CH_3$), 2.90 (s, 3H, $CH_3$), 3.04 (dd, J=5.5, 16 Hz, 1H, CHH), 3.09 (s, 3H, $CH_3$), 3.52 (dd, J=9.5, 15 Hz, 1H, CHH), 3.84 (s, 3H, $CH_3$), 4.07 (q, J=7.1 Hz, 2H, $CH_2$), 4.26 (d, J=17 Hz, 1H, CHH), 4.44 (d, J=17 Hz, 1H, CHH), 5.58 (dd, J=5.5, 9.4 Hz, 1H, NCH), 6.81-6.84 (m, 1H, Ar), 6.92-7.01 (m, 3H, Ar), 7.41 (t, J=7.8 Hz, 1H, Ar), 8.41 (d, J=8.3 Hz, 1H, Ar), 10.37 (s, 1H, NH); $^{13}C$ NMR ($CDCl_3$)~14.65, 24.84, 35.47, 36.16, 37.31, 48.71, 53.54, 55.85, 64.44, 111.35, 112.44, 116.83, 117.40, 117.97, 119.10, 131.72, 132.84, 137.65, 141.53, 148.46, 149.06, 168.98, 169.41, 169.57; Anal Calcd for $C_{24}H_{29}N_3O_5$+0.7$H_2O$: C, 63.76; H, 6.78; N, 9.29; $H_2O$, 2.79. Found: C, 63.89; H, 6.64; N, 9.14; $H_2O$, 2.70.

Example 60

(3R)-3-[7-(Cyclopropylcarbonylamino)-1-oxoisoindolin-2-yl]-3-(3-ethoxy-4-methoxyphenyl)-N,N-dimethylpropanamide A mixture of (3R)-3-(7-amino-1-oxoisoindolin-2-yl)-3-(3-ethoxy-4-methoxyphenyl)-N,N-dimethylpropanamide (450 mg, 1 mmol) and cyclopropane carbonyl chloride (0.13 mL, 1.4 mmol) in tetrahydrofuran (5 mL) was heated to reflux for 15 min. To the mixture was added 50% sodium hydrogen carbonate (40 mL) and ethyl acetate (50 mL). The organic layer was washed with sodium hydrogen carbonate (sat, 20 mL) and brine (20 mL), and dried over magnesium sulfate. The solvent was removed in vacuo to give an oil. The oil was purified by column chromatography (Silica Gel, 1:1 ethyl acetate:methylene chloride) to give (3R)-3-[7-(cyclopropylcarbonylamino)-1-oxoisoindolin-2-yl]-3-(3-ethoxy-4-methoxyphenyl)-N,N-dimethylpropanamide as a white solid (0.35 g, 67% yield); mp, 92-94° C.; $^1H$ NMR ($CDCl_3$)~0.82-0.89 (m, 2H, $CH_2$), 1.05-1.11 (m, 2H, $CH_2$), 1.43 (t, J=6.9 Hz, 3H, $CH_3$), 1.64-1.70 (m, 1H, CH), 2.90 (s, 3H, $CH_3$), 3.05 (dd, J=5.5, 16 Hz, 1H, CHH), 3.10 (s, 3H, $CH_3$), 3.52 (dd, J=9.5, 15 Hz, 1H, CHH), 3.84 (s, 3H, $CH_3$), 4.07 (q, J=7 Hz, 2H, $CH_2$), 4.26 (d, J=17 Hz, 1H, CHH), 4.44 (d, J=17 Hz, 1H, CHH), 5.60 (dd, J=5.7, 9.4 Hz, 1H, NCH), 6.82 (d, J=8.7 Hz, 1H, Ar), 6.93-6.99 (m, 2H, Ar), 7.39 (t, J=7.9 Hz, 1H, Ar), 8.39 (d, J=8.2 Hz, 1H, Ar), 10.59 (s, 1H, NH); $^{13}C$ NMR ($CDCl_3$) δ 8.04, 14.64, 16.03, 35.46, 36.19, 37.31, 48.72, 53.56, 55.85, 64.46, 111.41, 112.52, 116.56, 117.41, 117.82, 119.13, 131.79, 132.84, 137.84, 141.54, 148.48, 149.04, 169.50, 169.58, 172.51; Anal Calcd for $C_{26}H_{31}N_3O_5$+0.5$H_2O$: C, 65.81; H, 6.80; N, 8.85; $H_2O$, 1.90. Found: C, 65.83; H, 6.72; N, 8.72; $H_2O$, 1.94.

Example 61

3-{4-[2-(Dimethylamino)acetylamino]-1,3-dioxoisoindolin-2-yl}-3-(3-ethoxy-4-methoxyphenyl)-N,N-dimethylpropanamide hydrogen chloride Step 1: A solution of 3-[4-(2-chloroacetylamino)-1,3-dioxoisoindolin-2-yl]-3-(3-ethoxy-4-methoxyphenyl)propanoic acid (1.0 g, 2.2 mmol) and carbonyldiimidazole (367 mg, 2.26 mmol) in tetrahydrofuran (7 mL) was stirred at room temperature for 1 h. To the mixture was added dimethylamine in tetrahydrofuran (1.3 mL, 2 N, 2.6 mmol) and the mixture was stirred for 2 h. Water (60 mL) and methylene chloride (50 mL) were then added to mixture. The aqueous layer was separated and was extracted with ethyl acetate (50 mL). The combined organic layers was washed with brine/hydrogen chloride 1N (1:1, 50 mL), and dried over magnesium sulfate. The solvent was removed in vacuo to give 3-[4-(2-chloroacetylamino)-1,3-dioxoisoindolin-2-yl]-3-(3-ethoxy-4-methoxyphenyl)-N,N-dimethylpropanamide as a yellow solid (1.1 g, 100% yield), which was used in the next step without further purification.

Step 2: To a stirred solution of 3-[4-(2-chloroacetylamino)-1,3-dioxoisoindolin-2-yl]-3-(3-ethoxy-4-methoxyphenyl)-N,N-dimethylpropanamide (1.1 g, 2.3 mmol) in acetonitrile (15 mL) was added dimethylamine in tetrahydrofuran (3.3 mL, 2 N, 6.6 mmol) at room temperature and kept for overnight. The solvent was removed in vacuo to give a solid. The solid was diluted with methylene chloride (50 mL) and sodium hydrogen carbonate (25 mL). The separated organic layer was dried over magnesium sulfate. The solvent was removed in vacuo to give a solid. The solid was purified with chromatography to give 3-{4-[2-(dimethylamino)acetylamino]-1,3-dioxoisoindolin-2-yl}-3-(3-ethoxy-4-methoxyphenyl)-N,N-dimethylpropanamide as a white solid (640 mg, 57% yield). To a stirred solution of 3-{4-[2-(dimethylamino)acetylamino]-1,3-dioxoisoindolin-2-yl}-3-(3-ethoxy-4-methoxyphenyl)-N,N-dimethylpropanamide in ethyl acetate (4 mL) was added hydrogen chloride in ether (2 mL, 1N, 2 mmol) at room temperature. The resulting suspension was filtered and washed ethyl acetate to give 3-{4-[2-(dimethylamino)acetylamino]-1,3-dioxoisoindolin-2-yl}-3-(3-ethoxy-4-methoxyphenyl)-N,N-dimethylpropanamide hydrogen chloride as a white solid (580 mg, 84% yield): mp, 92-94° C.; $^1$H NMR (DMSO-d6) δ 1.30 (t, J=6.9 Hz, 3H, $CH_3$), 2.75 (s, 3H, $CH_3$), 2.87 (s, 6H, 2$CH_3$), 2.98 (s, 3H, $CH_3$), 3.21 (dd, J=5.7, 16.6 Hz, 1H, CHH), 3.61 (dd, J=9.3, 16.5 Hz, 1H, CHH), 3.72 (s, 3H, $CH_3$), 3.98 (q, J=6.9 Hz, 2H, $CH_2$), 4.26 (s, 2H, $CH_2$), 5.62 (dd, J=5.6, 9.1 Hz, 1H, NCH), 6.90-6.91 (m, 2H, Ar), 7.01 (s, 1H, Ar), 7.65 (d, J=7.2 Hz, 1H, Ar), 7.85 (t, J=7.7 Hz, 1H, Ar), 8.21 (d, J=8.2 Hz, 1H, Ar), 10.25 (brs, 1H, HCl), 10.56 (s, 1H, NH); $^{13}$C NMR (DMSO-d6) δ14.72, 26.37, 34.41, 34.81, 36.59, 43.34, 50.43, 55.52, 58.02, 63.78, 11.79, 112.38, 119.52, 127.79, 131.88, 131.94, 134.19, 135.79, 147.76, 148.47, 164.52, 167.25, 167.40, 169.16; Anal Calcd for $C_{26}H_{32}N_4O_6$+HCl+0.48$H_2O$: C, 57.65; H, 6.32; N, 10.34; Cl, 6.55; $H_2O$, 1.60. Found: C, 57.70; H, 6.28; N, 10.28, Cl, 6.81; $H_2O$, 1.61.

Example 62

(3R)-3-[7-(2-Chloroacetylamino)-1-oxoisoindolin-2-yl]-3-(3-ethoxy-4-methoxyphenyl)-N,N-dimethylpropanamide A mixture of (3R)-3-[7-(2-chloroacetylamino)-1-oxoisoindolin-2-yl]-3-(3-ethoxy-4-methoxyphenyl)-N,N-dimethylpropanamide (0.79 g, 1.7 mmol) and dimethylamine in tetrahydrofuran (2.5 mL, 2N, 5.0 mmol) in acetonitrile (15 mL) was stirred at room temperature overnight. The solvent was removed in vacuo to give an oil. The oil was dissolved in ethyl acetate (100 mL), washed with sodium hydrogen carbonate (2×20 mL, sat), brine (10 mL) and dried over magnesium sulfate. The solvent was removed in vacuo to give a solid. The solid was slurried in ether/hexanes (10 mL each) overnight to give a suspension. The suspension was filtered and the solid washed with hexanes to give (3R)-3-[7-(2-chloroacetylamino)-1-oxoisoindolin-2-yl]-3-(3-ethoxy-4-methoxyphenyl)-N,N-dimethylpropanamide as a white solid (622 mg, 77% yield); mp, 116-118° C.; $^1$H NMR ($CDCl_3$) δ 1.44 (t, J=7 Hz, 3H, $CH_3$), 2.43 (brs, 6H, 2$CH_3$), 2.89 (s, 3H, $CH_3$), 3.04 (dd, J=6.1, 15.3 Hz, 1H, CHH), 3.12 (s, 3H, $CH_3$), 3.13 (d, J=16 Hz, 1H, CHH), 3.19 (d, J=16 Hz, 1H, CHH), 3.44 (dd, J=9.1, 15 Hz, 1H, CHH), 3.85 (s, 3H, $CH_3$), 4.07 (q, J=7 Hz, 2H, $CH_2$), 4.17 (d, J=17 Hz, 1H, CHH), 4.43 (d, J=17 Hz, 1h, CHH), 5.67 (dd, J=6.2, 9 Hz, 1H, NCH), 6.82 (d, J=8.4 Hz, 1H, Ar), 6.91-7.02 (m, 3H, Ar), 7.43 (t, J=7.9 Hz, 1H, Ar), 8.52 (d, J=8.3 Hz, 1H, Ar), 11.38 (s, 1H, NH); $^{13}$C NMR ($CDCl_3$) δ 14.65, 35.41, 36.34, 37.41, 45.92, 48.27, 53.03, 55.85, 64.06, 64.38, 111.26, 112.66, 117.05, 117.76, 118.82, 119.10, 131.79, 132.59, 137.00, 141.76, 148.44, 148.94, 168.90, 169.66, 170.03; Anal Calcd for $C_{26}H_{34}N_4O_5$: C, 64.71; H, 7.10; N, 11.61. Found: C, 64.37; H, 6.96; N, 11.53.

Example 63

(3R)-3-{4-[2-(dimethylamino)acetylamino]-1,3-dioxoisoindolin-2-yl}-3-(3-ethoxy-4-methoxyphenyl)-N,N-dimethylpropanamide hydrogen chloride A mixture of (3R)-3-[4-(2-chloroacetylamino)-1,3-dioxoisoindolin-2-yl]-3-(3-ethoxy-4-methoxyphenyl)-N,N-dimethylpropanamide (8.10 g, 16.6 mmol) and dimethylamine in tetrahydrofuran (27 mL, 2N, 54 mmol) in acetonitrile (150 mL) was stirred at room temperature overnight. The solvent was removed in vacuo to give an oil. The oil was dissolved in ethyl acetate (150 mL), washed with sodium hydrogen carbonate (2×50 mL, sat), brine (50 mL), and dried over magnesium sulfate. The solvent was removed in vacuo to give a solid. The solid was purified by column chromatography (Silica Gel, 1.5% methanol in methylene chloride) to give (3R)-3-{4-[2-(dimethylamino)acetylamino]-1,3-dioxoisoindolin-2-yl}-3-(3-ethoxy-4-methoxyphenyl)-N,N-dimethylpropanamide as a white solid (6.3 g, 76% yield). To the solid in ethyl acetate (40 mL) was added hydrogen chloride in ether (20 mL, 1N). The suspension was filtered and washed with ether to give (3R)-3-{4-[2-(dimethylamino)acetylamino]-1,3-dioxoisoindolin-2-yl}-3-(3-ethoxy-4-methoxyphenyl)-N,N-dimethylpropanamide hydrogen chloride as a yellow solid (6.4 g, 72% yield); mp, 122-124° C.; $^1$H NMR (DMSO-d6) δ 1.33 (t, J=7 Hz, 3H, $CH_3$), 2.75 (s, 3H, $CH_3$), 2.89 (s, 6H, 2$CH_3$), 2.98 (s, 3H, $CH_3$), 3.22 (dd, J=5.4, 16.5 Hz, 1H, CHH), 3.60 (dd, J=9.2, 16.5 Hz, 1H, CHH), 3.71 (s, 3H, $CH_3$), 3.97 (q, J=7 Hz, 2H, $CH_2$), 4.30 (s, 2H, $CH_2$), 5.62 (dd, J=5.6, 8.7 Hz, 1H, NCH), 6.86-6.93 (m, 2H, Ar), 7.00 (s, 1H, Ar), 7.65 (t, J=7.1 Hz, 1H, Ar), 7.84 (t, J=7.5 Hz, 1H, Ar), 8.17 (d, J=7.9 Hz, 1H, Ar), 10.49 (s, 1H, ClH), 10.64 (s, 1H, NH); $^{13}$C NMR (DMSO-d6) δ 14.72, 34.41, 34.81, 36.59, 43.21, 50.43, 55.53, 57.77, 63.78, 111.79, 112.38, 119.32, 119.45, 119.58, 127.97, 131.90, 131.95, 134.12, 135.77, 147.76, 148.47, 164.28, 167.24, 167.33, 169.15; Anal Calcd for $C_{26}H_{32}N_4O_6$+HCl+1.1$H_2O$: C, 56.49; H, 6.42; N, 10.13; Cl, 6.41; $H_2O$, 3.58. Found: C, 56.33; H, 6.61; N, 9.95; $H_2O$, 3.51.

Example 64

3-(1,3-Dioxo-4-pyrrolylisoindolin-2-yl)-3-(3-ethoxy-4-methoxyphenyl)-N,N-dimethylpropanamide A mixture of 3-(1,3-dioxo-4-pyrrolylisoindolin-2-yl)-3-(3-ethoxy-4-methoxyphenyl)propanoic acid (1.29 g, 2.97 mmol), and carbonyldiimidazole (481 mg, 2.97 mmol) in tetrahydrofuran (13 mL) was stirred at room temperature for 2 h. To the mixture was added dimethylamine in tetrahydrofuran (1.7 mL, 2N, 3.4 mmol) and the mixture stirred for an additional 2 h. Water (70 mL) and methylene chloride (50 mL) was added to the mixture. The organic layer was separated, washed with brine (20 mL), and dried over magnesium sulfate. The solvent was removed in vacuo to give a brown solid. This solid was purified by column chromatography (silica gel, 1:5 ethyl acetate:methylene chloride+0.1% MeOH) to give 3-(1,3-dioxo-4-pyrrolylisoindolin-2-yl)-3-(3-ethoxy-4-methoxyphenyl)-N,N-dimethylpropanamide as a yellow solid (750 mg, 55% yield): mp, 105-107° C.; 1H NMR ($CDCl_3$) δ 1.43 (t, J=7 Hz, 3H, $CH_3$), 2.88 (s, 3H, $CH_3$), 3.00 (s, 3H, 2$CH_3$), 3.04 (dd, J=4.9, 16 Hz, 1H, CHH), 3.82 (s, 3H, $CH_3$), 3.91 (dd, J=10.2, 16.6 Hz, 1H, CHH), 4.09 (q, J=7 Hz, 2H, $CH_2$), 5.82 (dd, J=4.9, 10.2 Hz, 1H, NCH), 6.35 (t, J=2 Hz, 2H, Ar), 6.77-6.81 (m, 1H, Ar), 7.11-7.15 (m, 4H, Ar), 7.52-7.56 (m, 1H, Ar), 7.63-7.71 (m, 2H, Ar); $^{13}$C NMR ($CDCl_3$) δ 14.65, 34.71, 35.34, 37.02, 51.52, 55.83, 64.32, 110.48, 111.22, 112.76, 120.24, 120.66, 121.35, 122.02, 129.75, 132.00, 134.06, 134.94, 138.23, 148.15, 148.93, 166.19, 167.34, 169.58; Anal Calcd for $C_{26}H_{27}N_3O_5$+0.15$H_2O$: C, 67.30; H, 5.99; N, 8.85. Found: C, 67.16; H, 5.88; N, 8.92.

Example 65

2-[1-(3-Ethoxy-4-methoxyphenyl)-2-(methylsulfonyl)ethyl]-4-(imidazolylmethyl)isoindoline-1,3-dione A mixture of 4-(aminomethyl)-2-[1-(3-ethoxy-4-methoxyphenyl)-2-methylsulfonyl)isoindoline-1,3-dione (1.38 g, 3.20 mmol), glyoxal (40%, 0.46 g, 3.20 mmol) and formaldehyde (37%, 0.26 g, 3.20 mmol) in dilute $H_3PO_4$ (20 mL, pH=2) was heated to 80-90° C. Ammonium chloride (0.17 g) was added to the mixture and the mixture was maintained at 80-90° C. for 2 hours. The mixture was cooled to 15° C. and basified to pH 8 with $K_2CO_3$. The mixture was extracted with methylene chloride and the methylene chloride solution was washed with water (30 mL), brine (30 mL) and dried. The solvent was removed and the residue was purified by chromatography (silica gel, methylene chloride:methanol 97:3) to give 2-[1-(3-ethoxy-4-methoxyphenyl)-2-(methylsulfonyl)ethyl]-4-(imidazolylmethyl)isoindoline-1,3-dione (0.5 g, 32%) as a white solid. To a solution of the solid in ethyl acetate (5 mL) was added hydrogen chloride in ether (2 mL, 1N). The resulting suspension was filtered and washed with ether to give 2-[1-(3-ethoxy-4-methoxyphenyl)-2-(methylsulfonyl)ethyl]-4-(imidazolylmethyl)isoindoline-1,3-dione hydrochloride (0.26 g) as a white solid: mp 126-128° C.; 1H NMR (DMSO-$d_6$) δ 9.19 (s, 1H), 7.93-7.83 (m, 2H), 7.72 (s, 1H), 7.58 (d, J=7.2 Hz, 1H), 7.11 (d, J=1.2 Hz, 1H), 7.01-6.92 (m, 2H), 5.89 (s, 2H), 5.83-5.77 (dd, J=4.5, 10.1 Hz, 1H), 4.40-4.30 (dd, J=10.4, 14.3 Hz, 1H), 4.21-4.14 (dd, J=4.7, 14.4 Hz, 1H), 4.03 (q, J=6.9 Hz, 2H), 3.73 (s, 3H), 3.00 (s, 3H), 1.32 (t, J=6.9 Hz, 3H); $^{13}$C NMR (DMSO-$d_6$) δ 167.57, 166.97, 148.94, 147.86, 136.21, 135.41, 134.21, 133.46, 131.76, 129.37, 127.88, 123.59, 122.20, 120.56, 119.86, 112.43, 111.72, 63.82, 55.51, 52.98, 47.53, 47.03, 41.12, 14.67; Anal. Calcd. for $C_{24}H_{26}N_3O_6SCl$+0.53$H_2O$: C, 54.44; H, 5.15; N, 7.93; S, 6.06; Cl, 6.69. Found: C, 54.58; H, 5.11; N, 7.66; S, 6.23; Cl, 6.71.

Example 66

N-({2-[1-(3-Ethoxy-4-methoxyphenyl)-2-(methylsulfonyl)ethyl]-1,3-dioxoisoindolin-4-yl}methyl)acetamide A stirred mixture of 4-(aminomethyl)-2-[1-(3-ethoxy-4-methoxyphenyl)-2-(methylsulfonyl)ethyl]isoindoline-1,3-dione (0.92 g, 2.13 mmol) and acetic anhydride (10 mL) was heated at reflux for 40 min and then cooled to room temperature. Excess acetic anhydride was removed in vacuo. The residue was dissolved in ethyl acetate (50 mL) and washed with 2N hydrogen chloride (20 mL), water (20 mL), brine (20 mL), and dried over magnesium sulfate. The solvent was removed in vacuo and the residue was purified by chromatography (silica gel, methylene chloride:ethyl acetate 75:25) to give N-({2-[1-(3-ethoxy-4-methoxyphenyl)-2-(methylsulfonyl)ethyl]-1,3-dioxoisoindolin-4-yl}methyl)acetamide (0.56 g, 55%) as a white solid: mp 84-86° C.; 1H NMR ($CDCl_3$) δ 7.74-7.62 (m, 3H), 7.13-7.09 (m, 2H), 6.85-6.82 (m, 1H), 6.74-6.69 (m, 1H), 5.92-5.86 (dd, J=4.5, 10.1 Hz, 1H), 4.73 (d, J=6.3 Hz, 2H), 4.59-4.49 (dd, J=10.5, 14.2 Hz, 1H), 4.12 (q, J=6.8 Hz, 2H), 3.84 (s, 3H), 3.81-3.74 (m, 1H), 2.84 (s, 3H), 1.96 (s, 3H), 1.46 (t, J=6.9 Hz, 3H); $^{13}$C NMR ($CDCl_3$) δ 170.15, 168.58, 167.77, 149.64, 148.54, 138.05, 135.38, 134.39, 132.07, 129.32, 128.21, 122.73, 120.40, 112.41, 111.37, 64.45, 55.88, 54.61, 48.65, 41.55, 39.42, 23.08, 14.62; Anal. Calcd. for $C_{23}H_{26}N_2O_7S$: C, 58.22; H, 5.52; N, 5.90; S, 6.76. Found: C, 57.87; H, 5.52; N, 5.65; S, 6.66.

Example 67

2-Chloro-N-({2-[1-(3-ethoxy-4-methoxyphenyl)-2-(methylsulfonyl)ethyl]-1,3-dioxoisoindolin-4-yl}methyl)acetamide Triethylamine (0.52 g, 5.11 mmol) was added to a stirred suspension of 4-(aminomethyl)-2-[1-(3-ethoxy-4-methoxyphenyl)-2-(methylsulfonyl)ethyl]isoindoline-1,3-dione hydrochloride (1.0 g, 2.13 mmol). The clear solution was cooled in an ice bath to 5° C. Chloroacetyl chloride (0.30 g, 2.56 mmol) was added keeping the temperature between 5-9° C. The mixture was stirred at 5° C. for 30 min and then warmed to room temperature for 2 hours. The mixture was washed with water (2×30 mL), brine (30 mL) and dried over magnesium sulfate. The solvent was removed in vacuo and the residue was purified by chromatography (silica gel, methylene chloride:ethyl acetate 7:3) to give 2-chloro-N-({2-[1-(3-ethoxy-4-methoxyphenyl)-2-(methylsulfonyl)ethyl]-1,3-dioxoisoindolin-4-yl}methyl)acetamide (1.0 g, 92%): 1H NMR ($CDCl_3$) δ 7.84-7.65 (m, 4H), 7.14-7.12 (m, 2H), 6.86 (d, J=8.9 Hz, 1H), 5.94-5.88 (dd, J=4.6, 10.3 Hz, 1H), 4.79 (d, J=6.5 Hz, 2H), 4.61-4.51 (dd, J=10.4, 14.4 Hz, 1H), 4.10 (q, J=7.2 Hz, 2H), 4.02 (s, 2H), 3.85 (s, 3H), 3.80-3.72 (dd, J=4.6, 14.4 Hz, 1H), 2.86 (s, 3H), 1.47 (t, J=7.0 Hz, 3H).

Example 68

2-(Dimethylamino)-N-({2-[1-(3-ethoxy-4-methoxyphenyl)-2-(methylsulfonyl)ethyl]-1,3-dioxoisoindolin-4-yl}methyl)acetamide hydrochloride Dimethylamine/methanol (2.0 M, 2.95 mL) was added to a stirred solution of 2-chloro-N-({2-[1-(3-ethoxy-4-methoxyphenyl)-2-(methylsulfonyl)ethyl]-1,3-dioxoisoindolin-4-yl}methyl)acetamide (1.0 g, 1.96 mmol) in tetrahydrofuran and the mixture was stirred at room temperature for 24 hours. The tetrahydrofuran was removed in vacuo and the residue was dissolved in methylene chloride (60 mL). The methylene chloride solution was washed with water (30 mL), brine (30 mL) and dried over magnesium sulfate. The solvent was removed in vacuo and the residue was purified by chromatography (silica gel, methylene chloride:methanol 97.5:2.5) to give 2-(dimethylamino)-N-({2-[1-(3-ethoxy-4-methoxyphenyl)-2-(methylsulfonyl)ethyl]-1,3-dioxoisoindolin-4-yl}methyl)acetamide (0.6 g, 59%). To as stirred solution of the amine in ethyl acetate (10 mL) was added 1N hydrogen chloride in ether (4 mL). The resulting suspension was filtered and washed with ether to give 2-(dimethylamino)-N-({2-[1-(3-ethoxy-4-methoxyphenyl)-2-(methylsulfonyl) ethyl]1,3-dioxoisoindolin-4-yl}methyl)acetamide hydrochloride (0.55 g) as a white solid: mp 103-105° C.; $^1$H NMR (DMSO-$d_6$) δ 10.06 (s, 1H), 9.37 (m, 1H), 7.83-7.73 (m, 3H), 7.10 (s, 1H), 6.97-6.92 (m, 2H), 5.82-5.76 (dd, J=4.1, 10.2 Hz, 1H), 4.81 (d, J=5.6 Hz, 2H), 4.38-4.32 (dd, J=10.3, 14.1 Hz, 1H), 4.19-4.12 (dd, J=4.4, 14.4 Hz, 1H), 4.05-3.08 (m, 4H), 3.73 (s, 3H0, 3.02 (s, 3H), 2.82 (s, 6H0, 1.32 (t, J=6.9 Hz, 3H); $^{13}$C NMR (DMSO-$d_6$) δ 167.60, 167.20, 164.79, 148.88, 147.85, 137.84, 134.69, 133.36, 131.51, 129.59, 127.09, 122.14, 119.79, 112.41, 111.76, 63.84, 57.17, 55.49, 52.98, 47.29, 43.13, 41.09, 37.82, 14.67; Anal. Calcd. for $C_{26}H_{32}N_3O_7SCl$+0.56$H_2O$: C, 53.23; H, 5.92; N, 7.45, S, 5.68; Cl, 6.28. Found: C, 53.22; H, 5.87; N, 7.37; S, 5.64; Cl, 6.52.

Example 69

4-[Bis(methylsulfonyl)amino]-2-[1-(3-ethoxy-4-methoxyphenyl)-2-(methylsulfonyl)ethyl]isoindoline-1,3-dione Methanesulfonyl chloride (0.3 g, 2.62 mmol) was added to a stirred suspension of 4-amino-2-[1-(3-ethoxy-4-methoxyphenyl)-2-(methylsulfonyl)-ethyl]isoindoline-1,3-dione (0.55 g, 1.31 mmol) and triethylamine (0.4 g, 3.93 mmol) in methylene chloride (60 mL) and the resulting mixture stirred for 24 hours. The mixture was then washed with sat. Sodium bicarbonate (25 mL), 1N hydrogen chloride (25 mL), $H_2O$ (25 mL), brine (25 mL) and dried over magnesium sulfate. The solvent was removed in vacuo. The residue was slurried in methanol:tetrahydrofuran (2:1) to give after isolation by filtration 4-[bis(methylsulfonyl)amino]-2-[1-(3-ethoxy-4-methoxyphenyl)-2-(methylsulfonyl)ethyl]isoindoline-1,3-dione (0.53 g, 70%) as a white solid: mp 277-279° C.; $^1$H NMR (DMSO-$d_6$) δ 8.05-7.95 (m, 3H), 7.11-6.92 (m, 3H), 5.78-5.74 (dd, J=5.5, 9.1 Hz, 1H), 4.31-4.22 (m, 2H), 3.99 (q, J=6.9 Hz, 2H), 3.73 (s, 3H), 3.55 (s, 6H), 2.95 (s, 3H), 1.31 (t, J=7.0 Hz, 3H); $^{13}$C NMR (DMSO-$d_6$) δ 166.11, 165.35, 148.96, 147.88, 138.63, 136.05, 132.60, 129.64, 129.31, 129.27, 125.26, 119.89, 112.33, 111.76, 63.73, 55.46, 53.38, 47.92, 43.50, 43.44, 41.15, 14.61; Anal. Calcd. for $C_{22}H_{26}N_2O_{10}S_3$: C, 45.95; H, 4.56; N, 4.87; S, 16.74. Found: C, 45.90; H, 4.40; N, 4.75; S, 16.55.

Example 70

2-[1-(3-Ethoxy-4-methoxyphenyl)-2-(methylsulfonyl)ethyl]-4-[(methylsulfonyl)amino]isoindoline-1,3-dione A mixture of 4-[bis(methylsulfonyl)amino]-2-[1-(3-ethoxy-4-methoxyphenyl)-2-(methylsulfonyl)ethyl]isoindoline-1,3-dione (0.8 g, 1.39 mmol) and 2N NaOH (1.59 mL, 3.18 mmol) in $CH_3CN$ (120 mL) was stirred at room temperature for 8 hours. The mixture was neutralized with 6N hydrogen chloride (0.6 mL) and then concentrated. The residue was dissolved in methylene chloride (90 mL), washed with water (30 mL), brine (30 mL) and dried over magnesium sulfate. The solvent was removed in vacuo and the resulting solid was slurried in ethanol (50 mL) to give after isolation by filtration 2-[1-(3-ethoxy-4-methoxyphenyl)-2-(methylsulfonyl)ethyl]-4-[(methylsulfonyl)amino]isoindoline-1,3-dione (0.6 g, 86%) as a white solid: mp 191-193° C.; $^1$H NMR (DMSO-$d_6$) δ 9.31 (s, 1H), 7.85-7.74 (m, 2H), 7.61 (d, J=6.6 Hz, 1H), 7.08 (s, 1H), 7.00-6.91 (m, 2H), 5.80-5.74 (m, 1H), 4.38-4.28 (dd, J=10.5, 14.3 Hz, 1H), 4.19-4.11 (dd, J=4.5, 14.3 Hz, 1H), 4.03 (q, J=6.9 Hz, 2H), 3.73 (s, 3H), 3.27 (s, 3H), 3.00 (s, 3H0, 1.32 (t, J=6.9 Hz, 3H); $^{13}$C NMR (DMSO-$d_6$) δ 167.43, 166.71. 148.92, 147.87, 136.26, 135.73, 131.91, 129.40, 125.01, 119.79, 118.39, 117.59, 112.41, 111.76, 63.83, 55.48, 53.00, 47.35, 41.06, 40.63, 14.64; Anal. Calcd. for $C_{21}H_{24}N_2O_8S_3$+0.05 disulfonamide: C, 50.56; H, 4.86; N, 5.60; S, 13.12. Found: C, 50.25; H, 4.81; N, 5.60; S, 13.12.

Example 71

N-{2-[1-(3-Ethoxy-4-methoxyphenyl)-3-hydroxypentyl]-1,3-dioxoisoindolin-4-yl}acetamide A stirred mixture of 5-amino-5-(3-ethoxy-4-methoxyphenyl)pentan-3-ol hydrochloride (1.15 g, 3.97 mmol), 3-acetamidophthalic anhydride (0.82 g, 3.97 mmol) and triethylamine (0.4 g, 3.97 mmol) in DMF (20 mL) was heated at 80-90° C. for 6 hours. The mixture was then concentrated in vacuo. The residue was dissolved in ethyl acetate (80 mL), washed with water (30 mL), brine (30 mL) and dried over magnesium sulfate. The solvent was removed in vacuo and the residue was purified by chromatography (Silica gel, methylene chloride:ethyl acetate 8:2) to give N-{2-[1-(3-ethoxy-4-methoxyphenyl)-3-hydroxypentyl]-1,3-dioxoisoindolin-4-yl}acetamide (1.35 g, 77%); $^1$H NMR ($CDCl_3$) δ 9.52 (s, 1H), 8.71 (d, J=8.4 Hz, 1H), 7.63 (t, J=7.6 Hz, 1H), 7.48 (d, J=7.3 Hz, 1H), 7.09-7.07 (m, 2H), 6.83-6.80 (m, 1H), 5.61-5.55 (J=3.9, 11.9 Hz, 1H), 4.11 (q, J=6.9 Hz, 2H), 3.84 (s, 3H), 3.47 (m, 1H), 2.97-2.86 (m, 1H), 2.25 (s, 3H), 2.06-1.95 (m, 1H), 1.78 (b, 1H), 1.62-1.52 (m, 2H), 1.45 (t, J=7.0 Hz, 3H), 0.95 (t, J=7.3 Hz, 3H); $^{13}$C NMR ($CDCl_3$) δ 170.39, 169.23, 168.11, 148.94, 148.14, 137.32, 135.83, 131.81, 131.19, 124.72, 120.30, 117.94, 115.31, 112.87, 111.09, 70.01, 64.36, 55.86, 51.29, 37.92, 30.46, 24.92, 14.73, 9.90.

Example 72

N-{2-[1-(3-Ethoxy-4-methoxyphenyl)-3-oxopentyl]1,3-dioxoisoindolin-4-yl}acetamide A mixture of N-{2-[1-(3-ethoxy-4-methoxyphenyl)-3-hydroxypentyl]-1,3-dioxoisoindolin-4-yl}acetamide (1.35 g, 3.06 mmol), pyridinium chlorochromate (1.32 g, 6.12 mmol) and celite (0.6 g) in methylene chloride (35 mL) was stirred for 5 hours. The mixture was filtered through celite and the filtrate was washed with water (30 mL), brine (30 mL) and dried over magnesium sulfate. Solvent was removed in vacuo and the residue was purified by chromatography (Silica gel, methylene chloride:ethyl acetate 9:1) to give N-{2-[1-(3-ethoxy-4-methoxyphenyl)-3-oxopentyl]-1,3-dioxoisoindolin-4-yl}acetamide (1.08 g, 81%) as a white solid: mp 137-139° C.; $^1$H NMR ($CDCl_3$) δ 9.53 (s, 1H), 8.71 (d, J=8.4 Hz, 1H), 7.62 (t, J=7.6 Hz, 1H), 7.45 (d, J=7.3 Hz, 1H), 7.07-7.04 (m, 2H), 6.83 (d, J=8.8 Hz, 1H), 5.76-5.70 (dd, J=5.2, 10.1 Hz, 1H), 4.12 (q, J=6.9 Hz, 2H), 4.02-3.90 (dd, J=10.1, 17.9 Hz, 1H), 3.83 (s, 3H), 3.26-3.17 (dd, J=5.2, 17.9 Hz, 1H), 2.49 (q, J=7.3 Hz, 2H), 2.26 (s, 3H), 1.46 (t, J=6.9 Hz, 3H), 1.02 (t, J=7.3 Hz, 3H); $^{13}$C NMR ($CDCl_3$) δ 208.03, 170.02, 169.15, 167.86, 149.12, 148.33, 137.34, 135.76, 131.39, 131.22, 124.64, 120.00, 117.87, 115.29, 112.50, 111.27, 64.38, 55.89, 49.94, 43.51, 36.10, 24.92, 14.71, 7.52; Anal. Calcd. for $C_{24}H_{26}N_2O_6$: C, 65.74; H, 5.98: N, 6.39. Found: C, 65.74; H, 6.34; N, 6.38.

Example 73

2-[(1R)-1-(3-Ethoxy-4-methoxyphenyl)-3-hydroxybutyl]-4-(pyrrolylmethyl)isoindoline-1,3-dione A stirred mixture of (4R)-amino-4-(3-ethoxy-4-methoxyophenyl)butan-2-ol hydrochloride (1.14 g, 4.14 mmol), 3-(pyrrolylmethyl)phthalic anhydride (0.94 g, 4.14 mmol) and triethylamine (0.42 g, 4.14 mmol) in DMF (25 mL) was heated at 80-90° C. for 17 hours. The mixture was concentrated in vacuo, the residue was dissolved in ethyl acetate (80 mL), washed with water (30 mL), brine (30 mL) and dried over magnesium sulfate. The solvent was removed in vacuo and the residue was purified by chromatography (Silica gel, methylene chloride:ethyl acetate 9:1) to give 2-[(1R)-1-(3-ethoxy-4-methoxyphenyl)-3-hydrooxybutyl]-4-(pyrrolylmethyl)isoindoline-1,3-dione (1.27 g, 68%): $^1$H NMR ($CDCl_3$) δ 7.68 (d, J=7.3 Hz, 1H), 7.55 (t, J=7.7 Hz, 1H), 7.12-7.08 (m, 2H), 6.95 (d, J=7.9 Hz, 1H), 6.83 (d, J=8.0 Hz, 1H), 6.73-6.72 (m, 2H), 6.23-6.21 (m, 2H), 5.61-5.55 (dd, 1H), 4.13 (q, J=7.1 Hz, 2H), 3.84 (s, 3H), 3.78 (m, 1H), 2.94-2.83 (m, 1H), 2.16-2.08 (m, 1H), 1.76 (s, 1H), 1.46 (t, J=6.9 Hz, 3H), 1.29 (d, J=6.2 Hz, 3H); $^{13}$C NMR ($CDCl_3$) δ 168.86, 168.35, 148.94, 148.11, 138.35, 134.51, 132.43, 132.01, 131.77, 127.04, 122.37, 121.44, 120.55, 113.00, 111.09, 109.11, 64.98, 64.35, 55.87, 51.43, 48.52, 40.03, 23.68, 14.73.

Example 74

2-[(1R)-1-(3-Ethoxy-4-methoxyphenyl)-3-oxobutyl]-4-(pyrrolylmethyl)isoindoline-1,3-dione A mixture of 2-[(1R)-1-(3-ethoxy-4-methoxyphenyl)-3-hydroxybutyl]-4-(pyrrolylmethyl)isoindoline-1,3-dione (1.26 g, 2.81 mmol), pyridinium chlorochromate (1.21 g, 5.62 mmol), and celite (0.6 g) in methylene chloride (35 mL) was stirred at room temperature for 4 hours. The mixture was filtered through celite and the filtrate was washed with water (30 mL), brine (30 mL). The organic layer of the filtrate was dried over magnesium sulfate. The solvent was removed in vacuo and the residue was purified by chromatography (Silica gel, Hexane:ethyl acetate 6:4) to give 2-[(1R)-1-(3-ethoxy-4-methoxyphenyl)-3-oxobutyl]-4-(pyrrolylmethyl)isoindoline-1,3-dione (0.83 g, 66%) as a white solid: mp 143-145° C.; $^1$H NMR ($CDCl_3$) δ 7.66 (d, J=7.3 Hz, 1H), 7.53 (t, J=7.7 Hz, 1H), 7.10-7.06 (m, 2H), 6.93 (d, J=7.7 Hz, 1H), 6.82 (d, J=8.0 Hz, 1H), 6.73-6.71 (m, 2H), 6.22-6.21 (m, 2H), 5.78-5.72 (dd, J=5.4, 9.8 Hz, 1H), 3.32-3.23 (dd, J=5.4, 18.0 Hz, 1H), 2.18 (s, 3H), 1.46 (t, J=6.9 Hz, 3H); $^{13}$C NMR ($CDCl_3$) δ 205.31, 168.53, 167.83, 149.11, 148.33, 138.31, 134.43, 132.37, 132.04, 131.55, 127.05, 122.34, 121.46, 120.14, 112.59, 111.29, 109.08, 64.39, 55.91, 50.01, 48.53, 44.88, 30.17, 14.72; Anal. Calcd. for $C_{26}H_{26}N_2O_5$; C, 69.94; H, 5.87; N, 6.27. Found: C, 70.01; H, 6.01; N, 6.08.

Example 75

N-{2-[1-(3-Cyclopentyloxy-4-methoxyphenyl)-3-hydroxybutyl]-1,3-dioxoisoindolin-4-yl}acetamide A stirred mixture of 4-amino-4-(3-cyclopentyloxy-4-methoxyphenyl)butan-2-ol hydrochloride (1.20 g, 3.80 mmol), 3-acetamidophthalic anhydride (0.78 g, 3.80 mmol) and triethylamine (0.38 g, 3.80 mmol) in DMF (15 mL) was heated at 80-90° C. for 7 hours. The mixture was allowed to cool to room temperature and poured into water (80 mL). The resulting mixture was extracted with EtOAC (3×30 mL). The combined ethyl acetate extracts were washed with water (30 mL), brine (30 mL) and dried over magnesium sulfate. The solvent was removed in vacuo and the residue was purified by chromatography (Silica gel, methylene chloride:EtOAC 8:2) to give N-{2-1-(3-cyclopentyloxy-4-methoxyphenyl)-3-hydroxybutyl]-1,3-dioxoisoindolin-4-yl}acetamide (1.3 g, 73%) as a white solid: $^1$H NMR ($CDCl_3$) δ 9.53 (s, 1H), 8.71 (d, J=8.4 Hz, 1H), 7.63 (t, J=7.7 Hz, 1H), 7.48 (d, J=7.3 Hz, 1H), 7.08-7.03 (m, 2H), 6.82 (d, J=8.2 Hz, 1H), 5.57-5.51 (dd, J=4.2, 11.6 Hz, 1H), 4.78 (m, 1H), 3.81 (s, 3H), 3.77-3.74 (m, 1H), 2.91-2.81 (m, 1H), 2.25 (s, 3H), 2.13-1.60 (m, 10H), 1.29 (d, J=6.1 Hz, 3H); $^{13}$C NMR ($CDCl_3$) δ 170.38, 169.21, 168.06, 149.70, 147.50, 137.33, 135.84, 131.54, 131.20, 124.71, 120.28, 117.93, 115.31. 115.07, 111.55, 80.45, 64.89, 55.97, 51.35, 39.92, 32.73, 24.91, 24.04, 23.76, 21.02.

Example 76

N-{2-[1-(3-Cyclopentyloxy-4-methoxyphenyl)-3-oxobutyl]-1,3-dioxoisoindolin-4-yl}acetamide A mixture of N-{2-[1-(3-cyclopentyloxy-4-methoxyphenyl)-3-hydroxybutyl]-1,3-dioxoisoindolin-4-yl}acetamide (1.28 g, 2.74 mmol), pyridinium chlorochromate (1.18 g, 5.48 mmol) and celite (0.6 g) in methylene chloride (35 mL) was stirred at room temperature for 5 hours. The mixture was filtered through celite and the filtrate was washed with water (30 mL), brine (30 mL) and dried over magnesium sulfate. The solvent was removed in vacuo and the residue was purified by chromatography (Silica gel, methylene chloride:ethyl acetate 9:1) to give N-{2-[1-(3-cyclopentyloxy-4-methoxyphenyl)-3-oxobutyl]-1,3-dioxoisoindolin-4-yl}acetamide (1.09 g, 85%) as a white solid: mp 145-147° C.; $^1$H NMR ($CDCl_3$) δ 9.53 (s, 1H), 8.70 (d, J=8.4 Hz, 1H), 7.62 (t, J=7.6 Hz, 1H), 7.46 (d, J=7.3 Hz, 1H), 7.07-7.01 (m, 2H), 6.81 (d, J=8.2 Hz, 1H), 5.73-5.67 (dd, J=5.1, 9.8 Hz, 1H), 4.77 (m, 1H), 4.04-3.93 (dd, J=10.0, 18.1 Hz, 1H), 3.80 (s, 3H), 3.28-3.19 (dd, J=5.1, 18.0 Hz, 1H), 2.26 (s, 3H), 2.18 (s, 3H), 1.97-1.61 (m, 8H); $^{13}$C NMR ($CDCl_3$) δ 205.22, 170.03, 169.15, 167.82, 149.83, 147.70, 137.33, 135.77, 131.23, 124.63, 119.88, 117.87, 115.28, 114.57, 111.72, 80.46, 55.99, 49.94, 44.82, 32.75, 30.14, 24.92, 24.05; Anal. Calcd. for $C_{26}H_{28}N_2O_6$; C, 67.23; H, 6.08; N, 6.03. Found: C, 66.96; H, 6.06; N, 5.89.

Example 77

2-[1-(3-Cyclopentyloxy-4-methoxyphenyl)-3-oxobutyl]-4-pyrrolylisoindoline-1,3-dione A mixture of 2-[1-(3-cyclopentyloxy-4-methoxyphenyl)-3-oxobutyl]-4-aminoisoindoline-1,3-dione (0.41 g, 0.97 mmol), 2,5-dimethoxytetrahydrofuran (0.14 g, 1.07 mmol) and acetic acid (2 mL) in 1,2-dichloroethane (10 mL) was refluxed for 1 hour. The mixture was diluted with methylene chloride (25 mL) and washed with water (2×20 mL), brine (20 mL) and dried. Solvent was removed and the residue was purified by chromatography (Silica gel, Hexane:ethyl acetate 6:4) to give 2-[1-(3-cyclopentyloxy-4-methoxyphenyl)-3-oxobutyl]-4-pyrrolylisoindoline-1,3-dione (0.41 g, 91%) as a white solid: mp 142-144° C.; $^1$H NMR ($CDCl_3$) δ 7.72-7.56 (m, 3H), 7.14-7.04 (m, 4H), 6.79 (d, J=8.2 Hz, 1H), 6.38 (m, 2H), 5.77-5.71 (dd, J=5.4, 9.8 Hz, 1H), 4.77 (m, 1H), 4.05-3.94 (dd, J=9.9, 18.9 Hz, 1H), 3.79 (s, 3H), 3.30-3.21 (dd, J=5.4, 18.0 Hz, 1H), 2.16 (s, 3H), 1.98-1.60 (m, 8H); $^{13}$C NMR ($CDCl_3$) δ 205.31, 167.21, 166.14, 149.75, 147.61, 138.35, 135.09, 133.98, 131.34, 129.91, 126.04, 121.31, 120.74, 120.20, 114.72, 111.68, 110.61, 80.38, 55.97, 50.18, 44.72, 32.74, 30.12, 24.03; Anal. Calcd. for $C_{28}H_{28}N_2O_5$; C, 71.17; H, 5.97; N, 5.93. Found: C, 71.09; H, 6.09; N, 5.80.

Example 78

2-[1-(3,4-Dimethoxyphenyl)-3-oxobutyl]-4-[bis(methylsulfonyl)amino]isoindoline-1,3-dione A mixture of 2-[1-(3,4-dimethoxyphenyl)-3-oxobutyl]-4-aminoisoindoline-1,3-dione (1.02 g, 2.77 mmol) and triethylamine (1.40 g, 13.85 mmol) in methylene chloride (40 mL) was cooled to 5° C. Methanesulfonyl chloride (1.27 g, 11.08 mmol) was added at 5-8° C. and the resulting mixture was stirred at room temperature for 2 hours. The mixture was washed with sat. Sodium bicarbonate (20 mL), 1N hydrogen chloride (20 mL), water (30 mL), brine (30 mL) and dried over magnesium sulfate. The solvent was removed in vacuo and the residue was purified by chromatography (Silica gel, methylene chloride:ethyl acetate 9:1) to give 2-[1-(3,4-dimethoxyphenyl)-3-oxobutyl]-4-[bis(methylsulfonyl) amino]isoindoline-1,3-dione (1.18 g, 81%) as a white solid: mp 194-196° C.; $^1$H NMR (DMSO-$d_6$) δ 8.02-7.93 (m, 3H), 6.99-6.90 (m, 3H), 5.65 (t, J=6.7 Hz, 1H), 3.75-3.65 (m, 1H), 3.71 (s, 6H), 3.56 (s, 6H), 3.53-3.46 (m, 1H), 2.11 (s, 3H); $^{13}$C NMR (DMSO-$d_6$) δ 205.79, 166.58, 165.78, 148.64, 148.32, 138.48, 135.86, 132.68, 131.50, 129.85, 129.15, 125.06, 119.35, 111.58, 110.91, 55.49, 55.39, 49.27, 44.52, 43.53, 43.49, 29.92; Anal. Calcd. for $C_{22}H_{24}N_2O_9S_2$: C, 50.37; H, 4.61; N, 5.34, S, 12.23. Found: C, 50.43, H, 4.77; N, 5.16; S, 12.22.

What is claimed is:

1. A method of reducing elevated levels of PDE IV in a mammal, which comprises administering thereto an effective amount of a compound of formula (I):

I

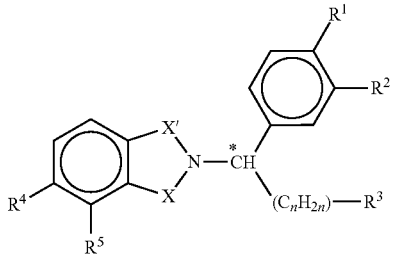

or an acid addition salt or a substantially chirally pure isomer thereof, wherein:

each of $R^1$ and $R^2$, independently of the other, is alkyl of 1 to 4 carbon atoms, alkoxy of 1 to 4 carbon atoms, cyano, cycloalkoxy of 3 to 18 carbon atoms, cycloalkyl of 3 to 18 carbon atoms, or cycloalkylmethoxy in which cycloalkyl has from 3 to 18 carbon atoms;

one of X and X' is ═C═O and the other of X and X' is ═C═O or ═$CH_2$;

$R^3$ is —$SO_2$—Y, —COZ, —CN, or hydroalkyl of 1 to 6 carbon atoms in which

Y is alkyl of 1 to 6 carbon atoms, phenyl, or benzyl;

Z is —$NR^{6''}R^{7''}$, alkyl of 1 to 6 carbon atoms, phenyl, or benzyl;

$R^{6''}$ is hydrogen, alkyl of 1 to 4 carbon atoms, cycloalkyl of 3 to 18 carbon atoms, phenyl, benzyl, or alkanoyl of 2 to 5 carbon atoms, each of which is unsubstituted or substituted with halo, amino, or alkylamino of 1 to 4 carbon atoms;

$R^{7''}$ is alkyl of 1 to 4 carbon atoms;

n is 1, 2, or 3;

one of $R^4$ and $R^5$ is hydrogen and the other of $R^4$ and $R^5$ is imidazolyl, pyrrolyl, oxadiazolyl, triazolyl, or

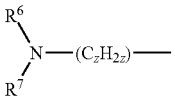

in which z is 0 or 1;

$R^6$, when taken independently of $R^7$, is selected from cycloalkanoyl whose cycloalkyl portion contains 3 to 6 carbon atoms, each of which is unsubstituted or substituted with halo, amino, monoalkylamino or dialkylamino in which each alkyl group contains 1 to 4 carbon atoms; and $R^7$ is hydrogen, alkyl of 1 to 4 carbon atoms, methylsulfonyl, or alkoxyalkylcarbonyl of 2 to 5 carbon atoms; or $R^6$ and $R^7$, taken together, are alkylidene of 1 or 2 carbon atoms substituted by amino, alkylamino, or dialkylamino, in which each alkyl group has from 1 to 4 carbon atoms, or, provided z is 1, —CH═CH—CH═CH—, or —CH═CH—N═CH—; and, the carbon atom designated * constitutes a center of chirality.

2. A method of treating an inflammatory disease or an autoimmune disease in a mammal, which comprises administering thereto an effective amount of a compound of formula (I):

I

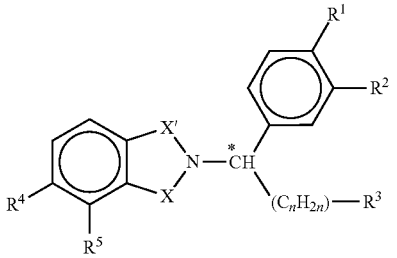

or an acid addition salt or a substantially chirally pure isomer thereof, wherein:

each of $R^1$ and $R^2$, independently of the other, is alkyl of 1 to 4 carbon atoms, alkoxy of 1 to 4 carbon atoms, cyano, cycloalkoxy of 3 to 18 carbon atoms, cycloalkyl of 3 to 18 carbon atoms, or cycloalkylmethoxy in which cycloalkyl has from 3 to 18 carbon atoms;

one of X and X' is ═C═O and the other of X and X' is ═C═O or $═CH_2$;

$R^3$ is $—SO_2—Y$, —COZ, —CN, or hydroalkyl of 1 to 6 carbon atoms in which

Y is alkyl of 1 to 6 carbon atoms, phenyl, or benzyl;

Z is $—NR^{6''}R^{7''}$, alkyl of 1 to 6 carbon atoms, phenyl, or benzyl;

$R^{6''}$ is hydrogen, alkyl of 1 to 4 carbon atoms, cycloalkyl of 3 to 18 carbon atoms, phenyl, benzyl, or alkanoyl of 2 to 5 carbon atoms, each of which is unsubstituted or substituted with halo, amino, or alkylamino of 1 to 4 carbon atoms;

$R^{7''}$ is alkyl of 1 to 4 carbon atoms;

n is 1, 2, or 3;

one of $R^4$ and $R^5$ is hydrogen and the other of $R^4$ and $R^5$ is imidazolyl, pyrrolyl, oxadiazolyl, triazolyl, or

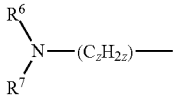

in which z is 0 or 1;

$R^6$, when taken independently of $R^7$, is selected from cycloalkanoyl whose cycloalkyl portion contains 3 to 6 carbon atoms, each of which is unsubstituted or substituted with halo, amino, monoalkylamino or dialkylamino in which each alkyl group contains 1 to 4 carbon atoms; and $R^7$ is hydrogen, alkyl of 1 to 4 carbon atoms, methylsulfonyl, or alkoxyalkylcarbonyl of 2 to 5 carbon atoms; or $R^6$ and $R^7$, taken together, are alkylidene of 1 or 2 carbon atoms substituted by amino, alkylamino, or dialkylamino, in which each alkyl group has from 1 to 4 carbon atoms, or, provided z is 1, —CH═CH—CH═CH—, or —CH═CH—N═CH—; and the carbon atom designated * constitutes a center of chirality.

3. A method of reducing elevated levels of PDE IV in a mammal, which comprises administering thereto an effective amount of a compound of formula:

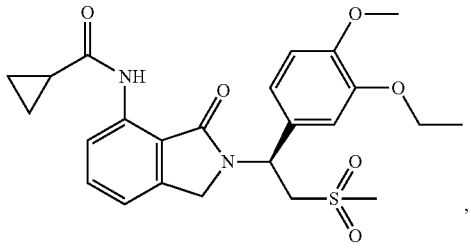

or an acid addition salt thereof.

4. A method of treating an inflammatory disease or an autoimmune disease in a mammal, which comprises administering thereto an effective amount of a compound of formula:

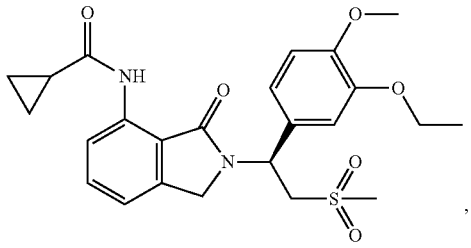

or an acid addition salt thereof.

5. The method of claim 2, wherein the inflammatory disease or autoimmune disease is an inflammatory respiratory condition.

6. The method of claim 2, wherein the inflammatory disease or autoimmune disease is asthma.

7. The method of claim 4, wherein the inflammatory disease or autoimmune disease is an inflammatory respiratory condition.

8. The method of claim 4, wherein the inflammatory disease or autoimmune disease is asthma.

*9. The method of claim 2, wherein the inflammatory disease or an autoimmune disease is psoriasis.*

*10. The method of claim 2, wherein the inflammatory disease or an autoimmune disease is rheumatoid arthritis.*

*11. The method of claim 2, wherein the inflammatory disease or an autoimmune disease is osteoarthritis.*

*12. The method of claim 2, wherein the inflammatory disease or an autoimmune disease is Crohn's disease.*

* * * * *